United States Patent [19]

Better

[11] Patent Number: 5,851,802
[45] Date of Patent: Dec. 22, 1998

[54] METHODS FOR RECOMBINANT MICROBIAL PRODUCTION OF FUSION PROTEINS AND BPI-DERIVED PEPTIDES

[75] Inventor: Marc D. Better, Los Angeles, Calif.

[73] Assignee: Xoma Corporation, Berkeley, Calif.

[21] Appl. No.: 621,803

[22] Filed: Mar. 22, 1996

[51] Int. Cl.[6] .................................................. C12M 15/62
[52] U.S. Cl. .................... 435/69.7; 435/69.8; 435/252.3; 435/252.33; 530/350; 536/23.4
[58] Field of Search ................................ 435/69.7, 69.8, 435/252.3, 252.33; 530/350; 536/23.4

[56] References Cited

U.S. PATENT DOCUMENTS

| | | | |
|---|---|---|---|
| 5,206,154 | 4/1993 | Lai et al. | 435/69.7 |
| 5,284,756 | 2/1994 | Grinna et al. | 435/69.4 |
| 5,416,202 | 5/1995 | Bernhard et al. | 536/23.2 |
| 5,627,153 | 5/1997 | Little, II et al. | 514/12 |

OTHER PUBLICATIONS

Qi et al. The region around residue 115 of the human bactericidal/permeability increasing protein is not involved in lipopysccharide binding or bactericidal activity: chemical synthesis and expression of a gene coding for the active domain and characte, 1994.
Callaway et al., "Modification of the C Terminus of Cecropin Is Essential for Broad–Spectrum Antimicrobial Activity," *Antimicrob. Agents & Chemo.*, 37(8):1614–1619 (1993).
Dykes et al., "Expression of aerial natriuretic factor as a cleavable fusion protein with chloramphenicol acetyltransferase in *Escheria coli*," *Eur. J. Biochem.*, 174:411–416 (1988).
Elsbach and Weiss, "Oxygen–Independent Bactericidal Systems of Polymorphonuclear Leukocytes," in Advances in Inflammation Research, ed. G. Weissmann, vol. 2, pp. 95–113 Raven Press (1981).
Elsbach and Weiss, "Oxygen–Independent Antimicrobial Systems of Phagocytes," in Inflammation: Basic Principles and Clinical Correlates, eds. Gallin et al., Chapter 30, Raven Press, Ltd. (1992).
Elsbach et al., "Separation and Purification of a Potent Bactericidal/Permeability–Increasing Protein and a Closely Associated Phospholipase $A_2$ from Rabbit Polymorphonuclear Leukocytes," *J. Biol. Chem.*, 254:11000–11009 (Nov. 10, 1979).
Gazzano–Santoro et al., "High–Affinity Binding of the Bactericidal/Permeability–Increasing Protein and a Recombinant Amino–Terminal Fragment to the Lipid A Region of Lipopolysaccharide," *Infect. Immun.*, 60:4754–4761 (Nov. 1992).
Gramm et al., "A Novel Approach for High Level Production of a Recombinant Human Parathryiod Hormone Fragment in *Escheria coli*," *Bio/Technology*, 12:1017 (Oct. 12, 1994).
Gray et al., "Cloning of the cDNA of a Human Neutrophil Bactericidal Protein," *J. Biol. Chem.*, 264:9505–9509 (Jun. 5, 1989).

In't Veld et al., "Effects of the Bactericidal/Permeability–Increasing Proein of Polymorphonuclear Leukocytes on Isolated Bacterial Cytoplasmic Membrane Vesicles," *Infection and Immunity* 56:1203–1208 (1988).
Kempe et al., "Multiple–copy genes: production and modification of monomeric peptides from large multimeric fusion proteins," *Gene*, 39:239–245 (1985).
Kuliopulos and Walsh, "Production, Purification, and Cleavage of Tandem Repeats of Recombinant Peptides," *J. Am. Chem. Soc.*, 116:4599–4607 (1994).
Lennick et al., "High–level expression of α–human atrial natriuretic peptide from multiple joined genes in *Escheria coli*," *Gene*, 61:103–112 (1987).
Mannion et al., "Separation of Sublethal and Lethal Effects of Polymorphonuclear Leukocytes on *Escherichia coli*," *J. Clin. Invest.* 86:631–641 (1990).
Mannion et al., "Separation of Sublethal and Lethal Effects of Bactericidal/Permeability Increasing Protein on *Escherichia coli*," *J. Clin. Invest.*, 85:853–860 (Mar. 1990).
Ooi et al., "A 25–kDa $NH_2$–terminal Fragment Carries All the Antibacterial Activities of the Human Neutrophil 60–kDa Bactericidal/Permeability–increasing Protein," *J. Bio. Chem.*, 262:14891–14894 (1987).
Ooi et al., "Endotoxin–neutralizing Properties of the 25 kD N–Terminal Fragment and a Newly Isolated 30 kD C–Terminal Fragment of the 55–60 kD Bactericidal/Permeability–Increasing Protein of Human Neutrophils," *J. Exp. Med.*, 174:649–655 (Sep. 1991).
Piers et al., "Recombinant DNA procedures for producing small antimicrobial cationic peptides in bacteria," *Gene*, 134:7–13 (1993).
Ray et al., "Production of Recombinant Salmon Calcitonin by In Vitro Amidation of an *Escheria coli* Produced Precursor Peptide," *Bio/ Technology*, 11:64 (Jan. 1993).
Schellenberger et al., "Peptide production by a combination of gene expression, chemical synthesis, and protease–catalyzed conversion," *Int. J. Peptide Protein Res.*, 41:326–332 (1993).
Shen, "Multiple joined genes prevent product degradation in *Escheria coli*," *Proc. Natl. Acad. Sci. USA*, 81:4627–4631 (Aug. 1984).
Weiss et al., "The Role of Lipopolysaccharides in the Action of the Bactericidal/Permeability–Increasing Neutrophil Protein on the Bacterial Envelope," *J. Immunol.* 132:3109–3115 (1984).
Weiss et al., "Resistance of Gram–negative Bacteria to Purified Bactericidal Leukocyte Proteins," *J. Clin. Invest.* 65:619–628 (1980).
Weiss and Olsson, "Cellular and Subcellular Localization of the Bactericidal/Permeability–Increasing Protein of Neutrophils," *Blood*, 69:652–659 (Feb. 1987).
Weissmann, vol. 2, pp. 95–113 Raven Press (1981).

*Primary Examiner*—Lorraine Spector
*Attorney, Agent, or Firm*—McAndrews, Held & Malloy, Ltd.

[57] ABSTRACT

The present invention relates to methods and materials for the recombinant microbial production of fusion proteins and peptides derived from or based on Domain I (amino acids 17–45), Domain II (amino acids 65–99) and Domain III (amino acids 142–169) of bactericidal/permeability-increasing protein (BPI).

15 Claims, 5 Drawing Sheets

METHODS FOR RECOMBINANT MICROBIAL PRODUCTION OF FUSION PROTEINS AND BPI-DERIVED PEPTIDES

BACKGROUND OF THE INVENTION

The present invention relates generally to methods for recombinant microbial production of fusion proteins and peptides derived from or based on Domain I (amino acids 17–45), Domain II (amino acids 65–99) and Domain III (amino acids 142–169) of bactericidal/permeability-increasing protein (BPI).

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. DNA and amino acid sequences are set out in SEQ ID NOS: 264 and 265 hereto.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N- terminal fragment of human BPI possesses the anti-bacterial efficacy of the naturally-derived 55 kD human BPI holoprotein. [Ooi et al., *J. Bio. Chem.*, 262: 14891–14894 (1987)]. In contrast to the N-terminal portion, the C-tenninal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms [Gazzano-Santoro et al., *Infect. Immun.* 60:4754–4761 (1992)]. In that publication, an expression vector was used as a source of DNA encoding a recombinant expression product (rBPI$_{23}$). The vector was constructed to encode the 31-residue signal sequence and the first 199 amino acids of the N-terminus of the mature human BPI, as set out in SEQ ID NOS: 264 and 265 taken from Gray et al., supra, except that valine at position 151 is specified by GTG rather than GTC and residue 185 is glutamic acid (specified by GAG) rather than lysine (specified by AAG). Recombinant holoprotein, also referred to as rBPI, has also been produced having the sequence set out in SEQ ID NOS: 264 and 265 taken from Gray et al., supra, with the exceptions noted for rBPI$_{23}$. An N-terminal fragment analog designated rBPI$_2$, or rBPI$_{21}$Δcys has been described in co-owned, copending U.S. Pat. No. 5,420,019 which is incorporated herein by reference. This analog comprises the first 193 amino acids of BPI holoprotein as set out in SEQ ID NOS: 264 and 265 but wherein the cysteine at residue number 132 is substituted with alanine, and with the exceptions noted for rBPI$_{23}$.

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). BPI is commonly thought to be non-toxic for other microorganisms, including yeast, and for higher eukaryotic cells. Elsbach and Weiss (1992), supra, reported that BPI exhibits anti-bacterial activity towards a broad range of gram-negative bacteria at concentrations as low as $10^{-8}$ to $10^{-9}$ M, but that 100- to 1,000-fold higher concentrations of BPI were non-toxic to all of the gram-positive bacterial species, yeasts, and higher eukaryotic cells tested at that time. It was also reported that BPI at a concentration of $10^{-6}$ M or 160 μg/mL had no toxic effect, when tested at a pH of either 7.0 or 5.5, on the gram-positive organisms *Staphylococcus aureus* (four strains), *Staphylococcus epidernidis*, *Streptococcus faecalis*, *Bacillus subtilis*, *Micrococcus lysodeikticus*, and *Listeria monocytogenes*. BPI at $10^{-6}$ M reportedly had no toxic effect on the fungi *Candida albicans* and *Candida parapsilosis* at pH 7.0 or 5.5, and was non-toxic to higher eukaryotic cells such as human, rabbit and sheep red blood cells and several human tumor cell lines. See also Elsbach and Weiss, *Advances in Inflammation Research*, ed. G. Weissmann, Vol. 2, pages 95–113 Raven Press (1981). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through hydrophobic and electrostatic interactions between the cationic BPI protein and negatively charged sites on the bacterial LPS. Bacterial LPS has been referred to as "endotoxin" because of the potent inflammatory response that is stimulated, i.e., the release of mediators by host inflammatory cells which may ultimately result in irreversible endotoxic shock. BPI binds to lipid A, reported to be the most toxic and most biologically active component of bacterial LPS.

In susceptible gram-negative bacteria, BPI binding is thought to disrupt LPS structure, leading to activation of bacterial enzymes that degrade phospholipids and peptidoglycans, altering the penneability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to bacterial LPS leads to organizational changes that probably result from binding to the anionic groups in the KDO region of LPS, which normally stabilize the outer membrane through binding of $Mg^{++}$ and $Ca^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [Weiss et al., *J. Clin. Invest.* 65: 619–628 (1980)]. This first stage of BPI action, permeabilization of the gram-negative outer envelope, is reversible upon dissociation of the BPI, a process requiring the presence of divalent cations and synthesis of new LPS [Weiss et al., *J. Immunol.* 132: 3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane [Mannion et al., *J. Clin. Invest.* 86: 631–641 (1990)]. Specific investigation of this possibility has shown that on a molar basis BPI is at least as inhibitory of cytoplasmic membrane vesicle function as polymyxin B [In't Veld et al., *Infection and Immunity* 56: 1203–1208 (1988)] but the exact mechanism as well as the relevance of such vesicles to studies of intact organisms has not yet been elucidated.

In addition to its direct bactericidal activity, BPI is also capable of neutralizing the endotoxic properties of living or dead bacteria and LPS released from the bacteria. Because of its gram-negative bactericidal properties and its ability to bind to and neutralize bacterial LPS, BPI can be utilized for the treatment of mammals suffering from diseases caused by gram-negative bacteria, including bacteremia, endotoxemia, and sepsis. These dual properties of BPI make BPI particularly useful and advantageous for such therapeutic administration.

BPI protein products, including BPI-derived peptides, are useful as adjunct therapy with conventional antibiotics as described in copending and co-assigned U.S. patent application Ser. No. 08/311,611 filed Sep. 22, 1994, now U.S. Pat. No. 5,523,288, and WO95/08344 (PCT/US94/11225). Specifically, concurrent administration, or co-treatment, of such BPI protein products and an antibiotic or combination of antibiotics may improve the therapeutic effectiveness of antibiotics in a variety of ways, including by increasing susceptibility of gram-negative bacteria to a reduced dosage of antibiotics, by effectively reversing resistance of gram-negative bacteria to antibiotics, by providing synergistic or potentiating effects beyond the individual or additive effects of the BPI protein product or antibiotic alone, or by neutralizing endotoxin released by bacteria killed by antibiotics. Concurrent administration of BPI protein products and antibiotics provide unexpectedly superior therapeutic effects in vivo than either agent provides when administered alone. In particular, concurrent administration of BPI protein product according to this improved method of treatment is effective even when the gram-negative bacteria involved are considered to be resistant to the bactericidal effects of BPI protein product alone and/or antibiotic alone. BPI protein products are therefore useful for prophylaxis or treatment of gram-negative bacterial infections, including for prophylaxis of patients at high risk of gram-negative bacterial infection, e.g., patients who will undergo abdominal or genitourinary surgery, or trauma victims.

BPI protein products, including BPI-derived peptides, have been shown recently to have direct and indirect bactericidal and growth inhibitory effects on some gram-positive organisms as described in copending U.S. patent application Ser. No. 08/372,783 filed Jan. 13, 1995, now U.S. Pat. No. 5,578,572 and WO95/19180 (PCT/US95/00656). In addition, BPI protein products unexpectedly were shown to have the ability to increase the antibiotic susceptibility of gram-positive bacteria, including the ability to reverse in many instances the antibiotic resistance of gram-positive bacteria. BPI protein products and antibiotics provided additive and synergistic bactericidal/growth inhibitory effects when administered concurrently. Such BPI protein products are therefore useful for treating gram-positive bacterial infections, including conditions associated therewith or resulting therefrom (for example, sepsis or bacteremia).

BPI protein products, including BPI-derived peptides, have also been shown recently to have fungicidal/fungistatic effects as described in copending and co-assigned U.S. patent application Ser. No. 08/372,105 filed Jan. 13, 1995, now U.S. Pat. No. 5,627,157, and WO95/19179 (PCT/US95/00498). Such BPI protein products may be administered alone or in conjunction with known anti-fungal agents. When made the subject of adjunctive therapy, the administration of BPI protein products may reduce the amount of anti-fungal agent needed for effective therapy, thus limiting potential toxic response and/or high cost of treatment. Administration of BPI protein products may also enhance the effect of such agents, accelerate the effect of such agents, or reverse resistance of fungi to such agents.

BPI has other important biological activities. For example, BPI protein products, including BPI-derived peptides, have been shown to have heparin binding and heparin neutralization activities in copending and co-assigned U.S. Pat. No. 5,348,942 issued Sep. 20, 1994 incorporated by reference herein. These heparin binding and neutralization activities are significant due to the importance of current clinical uses of heparin. Heparin is commonly administered in doses of up to 400 U/kg during surgical procedures such as cardiopulmonary bypass, cardiac catheterization and hemodialysis procedures in order to prevent blood coagulation during such procedures. When heparin is administered for anticoagulant effects during surgery, it is an important aspect of post-surgical therapy that the effects of heparin are promptly neutralized so that normal coagulation function can be restored. Currently, protamine is used to neutralize heparin. Protamines are a class of simple, arginine-rich, strongly basic, low molecular weight proteins. Administered alone, protamines (usually in the form of protamine sulfate) have anti-coagulant effects. When administered in the presence of heparin, a stable complex is formed and the anticoagulant activity of both drugs is lost. However, significant hypotensive and anaphylactoid effects of protamine have limited its clinical utility. Thus, due to its heparin binding and neutralization activities, BPI has potential utility as a substitute for protamine in heparin neutralization in a clinical context without the deleterious side-effects which have limited the usefulness of the protamines. The additional antibacterial and anti-endotoxin effects of BPI would also be useful and advantageous in post-surgical heparin neutralization compared with protamine.

Additionally, BPI protein products are useful in inhibiting angiogenesis due in part to its heparin binding and neutralization activities. In adults, angiogenic growth factors are released as a result of vascular trauma (wound healing), immune stimuli (autoimmune disease), inflammatory mediators (prostaglandins) or from tumor cells. These factors induce proliferation of endothelial cells (which is necessary for angiogenesis) via a heparin-dependent receptor binding mechanism. Angiogenesis is also associated with a number of other pathological conditions, including the growth, proliferation, and metastasis of various tumors; diabetic retinopathy, retrolental fibroplasia, neovascular glaucoma, psoriasis, angiofibromas, immune and non-immune inflammation including rheumatoid arthritis, capillary proliferation within atherosclerotic plaques, hemangiomas, endometriosis and Kaposi's sarcoma. Thus, it would be desirable to inhibit angiogenesis in these and other instances, and the heparin binding and neutralization activities of BPI are useful to that end.

Another utility of BPI protein products involves pathological conditions associated with chronic inflammation, which is usually accompanied by angiogenesis. One example of a human disease related to chronic inflammation is arthritis, which involves inflammation of peripheral joints. In rheumatoid arthritis, the inflammation is immune-driven, while in reactive arthritis, inflammation is associated with infection of the synovial tissue with pyogenic bacteria or other infectious agents. Many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease or an epiphenomenon, there is evidence that angiogenesis is necessary for the maintenance of synovitis in rheumatoid arthritis. BPI has been shown to provide effective therapy for arthritis and other inflammatory diseases.

Three separate functional domains within the recombinant 23 kD N-terminal BPI sequence were discovered by Little et al., *J. Biol. Chem.* 269: 1865 (1994) [see also copending and co-assigned WO94/20128 (PCT/US94/02401); WO94/20532 (PCT/US94/02465);and WO95/19372 (PCT/US94/10427)]. These functional domains of BPI designate a region of the amino acid sequence of BPI that contributes to the total biological activity of the protein and were essentially defined by the activities of proteolytic cleavage fragments, overlapping 15-mer peptides and other synthetic peptides. Domain I is defined as the amino acid sequence of BPI comprising from about amino acid 17 to about amino acid 45. Peptides derived from this domain were moderately active in both the inhibition of LPS-induced LAL activity and in heparin binding assays, and did not exhibit significant bactericidal activity. Domain II is defined as the amino acid sequence of BPI comprising from about amino acid 65 to about amino acid 99. Peptides derived from or based on this domain exhibited high LPS and heparin binding capacity and were bactericidal. Domain III is defined as the amino acid sequence of BPI comprising from about amino acid 142 to about amino acid 169. Peptides derived from or based on this domain exhibited high LPS and heparin binding activity and were bactericidal. The biological activities of BPI functional domain peptides may include LPS binding, LPS neutralization, heparin binding, heparin neutralization or antimicrobial activity.

Of interest to the present application are the disclosures of the following references which relate to recombinant fusion proteins and peptides.

Shen, *Proc. Nat'l. Acad. Sci. (USA)*, 281:4627 (1984) describes bacterial expression as insoluble inclusion bodies of a fusion protein encoding pro-insulin and β-galactosidase; the inclusion bodies were solubilized with formic acid prior to cleavage with cyanogen bromide.

Kempe et al., *Gene*, 39:239 (1985) describes expression as insoluble inclusion bodies in *E. coli* of a fusion protein encoding multiple units of neuropeptide substance P and β-galactosidase; the inclusion bodies were solubilized with formic acid prior to cleavage with cyanogen bromide.

Lennick et al., *Gene*, 61:103 (1987) describes expression as insoluble inclusion bodies in *E. coli* of a fusion protein encoding multiple units (8) of α-human atrial natriuretic peptide; the inclusion bodies were solubilized with urea prior endoproteinase cleavage.

Dykes et al., *Eur. J. Biochem.*, 174:411 (1988) describes soluble intracellular expression in *E. coli* of a fusion protein encoding β-human atrial natriuretic peptide and chloramphenicol acetyltransferase; the fusion protein was proteolytically cleaved or chemically cleaved with 2-(2-nitrophenylsulphenyl)-E-methyl-3'-bromoindolenine to release peptide.

Ray et al., *Bio/Technology*, 11:64 (1993) describes soluble intracellular expression in *E. coli* of a fusion protein encoding salmon calcitonin and glutathione-S-transferase; the fusion protein was cleaved with cyanogen bromide.

Schellenberger et al., *Int. J. Peptide Protein Res.*, 41:326 (1993) describes expression as insoluble inclusion bodies of a fusion protein encoding a substance P peptide (11a.a.) and β-galactosidase; the inclusion bodies were treated with chymotrypsin to cleave the fusion protein.

Hancock et al., WO94/04688 (PCT/CA93/00342) and Piers et al. (Hancock), Gene, 134:7 (1993) describe (a) expression as insoluble inclusion bodies in *E. coli* of a fusion protein encoding a defensin peptide designated human neutrophil peptide 1 (HNP-1) or a hybrid cecropin/mellitin (CEME) peptide and glutathione-5-transferase (GST); the inclusion bodies were: (i) extracted with 3 % octylpolyoxyethylene prior to urea solubilization and prior to factor $X_a$ protease for HNP1-GST fusion protein or (ii) solubilized with formic acid prior to cyanogen bromide cleavage for CEME-GST fusion protein; (b) expression in the extracellular supernatant of *S. aureus* of a fusion protein encoding CEME peptide and protein A; (c) proteolytic degradation of certain fusion proteins with some fusion protein purified; and (d) proteolytic degradation of other fusion proteins and inability to recover and purify the fusion protein.

Lai et al., U.S. Pat. No. 5,206,154 and Callaway, Lai et al. *Antimicrob. Agents & Chemo.*, 37:1614 (1993) describe expression as insoluble inclusion bodies of a fusion protein encoding a cecropin peptide and the protein encoded by the 5'-end of the L-ribulokinase gene; the inclusion bodies were solubilized with formic acid prior to cleavage with cyanogen bromide.

Gamm et al., *Bio/Technology*, 12:1017 (1994) describes expression as insoluble inclusion bodies in *E. coli* of a fusion protein encoding a human parathyroid hormone peptide and a bacteriophage T4-encoded gp55 protein; the inclusion bodies (6% wt/vol.) were treated with acid to hydrolyze the Asp-Pro cleavage site.

Kuliopulos et al., *J. Am. Chem. Soc.*, 116:4599 (1994) describes expression as insoluble inclusion bodies in *E. coli* of a fusion protein encoding multiple units of a yeast α-mating type peptide and a bacterial ketosteroid isomerase protein; the inclusion bodies were solubilized with guanidine prior to cyanogen bromide cleavage.

The above-references indicate that production of small peptides from bacteria has been problematic for a variety of reasons. Proteolysis of some peptides has been particularly problematic, even where the peptide is made as a part of a larger fusion protein. Such fusion proteins comprising a carrier protein/peptide may not be expressed by bacterial host cells or may be expressed but cleaved by bacterial proteases. In particular, difficulties in expressing cationic antimicrobial peptides in bacteria have been described by Hancock et al. WO94/04688 (PCT/CA93/00342) referenced above, due in their view to the susceptibility of such polycationic peptides to bacterial protease degradation.

There continues to exist a need in the art for new recombinant products and in particular, a need for methods for recombinant production of BPI-derived peptides useful as antimicrobial agents (including anti-bacterial and anti-fungal agents), as endotoxin binding and neutralizing agents, and as heparin binding and neutralizing agents, including agents for neutralizing the anticoagulant effects of administered heparin, for treatment of chronic inflammatory disease states, and for inhibition of normal or pathological angiogenesis.

SUMMARY OF THE INVENTION

The present invention provides methods and materials for recombinant microbial production of fusion proteins and peptides derived from or based on bactericidal/permeability-increasing protein (BPI). Preferred BPI peptides are derived from Domain I (amino acids 17–45), Domain II (amino acids 65–99) and Domain m (amino acids 142–169) of BPI, each peptide having an amino acid sequence that is the amino acid sequence of a BPI functional domain or a subsequence thereof and variants of the sequence or subsequence having at least one of the biological activities of BPI. Fusion proteins of the invention comprise at least one BPI peptide sequence, a carrier protein sequence, and at least one amino acid cleavage site sequence located between the BPI peptide and the carrier protein sequence. The invention provides a method for the microbial production of such fusion proteins encoding one or more BPI peptides. The recombinant BPI-derived peptides of the invention are released by cleavage at the cleavage site(s) in the fusion protein. Such peptides are efficiently and economically produced according to the invention.

Methods of the invention for recombinant microbial production of fusion proteins and BPI-derived peptides are based on the surprising discovery that such fusion proteins are expressed in large amounts intracellularly or secreted from microbial host cells, that antimicrobial BPI peptides are efficiently produced by microbial host cells and that the peptides are efficiently cleaved and released from the fusion proteins. It is particularly surprising that antibacterial BPI peptides according to the invention are effectively made in *E. coli*. Such BPI-derived peptides having one or more of the biological activities of BPI can be isolated and purified according to the invention. Thus, the invention provides functional recombinant BPI peptides. Biologically active recombinant BPI peptides of the invention released from the fusion proteins have one or more of the following activities: LPS binding, LPS neutralization, heparin binding, heparin neutralization or antimicrobial activity (including anti-bacterial, anti-fungal activity).

As such, recombinant BPI-derived peptides are useful as antimicrobial agents (including anti-bacterial and anti-fungal agents), as endotoxin binding and neutralizing agents, and as heparin binding and neutralizing agents including agents for neutralizing the anticoagulant effects of administered heparin, for treatment of chronic inflammatory disease states, and for inhibition of normal or pathological angiogenesis.

The invention provides recombinant DNA vector constructs suitable for introduction into a bacterial host in which the construct includes a coding sequence for a fusion protein having: (a) at least one cationic BPI peptide encoding DNA sequence; (b) a carrier protein encoding DNA sequence; and (c) an amino acid cleavage site encoding DNA sequence located between the sequences (a) and (b). According to the invention, a preferred vector construct is provided with a coding sequence for a fusion protein is 5'-(b)-(c)-(a)-3', that is, from 5' to 3', a carrier encoding sequence, followed by a cleavage site encoding sequence, and then a peptide encoding sequence. The invention further provides an encoded BPI peptide that is bactericidal, fungicidal, endotoxin binding, endotoxin neutralizing, heparin binding or heparin neutralizing. According to one aspect of the invention, an encoded BPI peptide is provided that comprises an amino acid sequence of SEQ ID NOS: 1–239. The invention also provides an encoded carrier protein that is a cationic carrier protein, for example, gelonin or the D subunit of human osteogenic protein. Constructs are also provided that additionally encode a bacterial secretory leader sequence at the amino-terminus of the fusion protein. An encoded amino acid cleavage site is provided in vector constructs, including codons encoding Asp-Pro, Met, Trp and Glu. Bacterial host cells transformed with vector constructs according to the invention are provided, including *E. Coli* host cells.

The invention provides methods for bacterial production of fusion proteins and BPI peptides by culturing transformed bacterial host cells transformed with a vector construct encoding the fusion protein that has BPI peptide -, carrier protein -, and amino acid cleavage site - encoding sequences, by optionally isolating the expressed fusion protein, by cleaving the expressed fusion protein to release the BPI peptide, and by isolating the BPI peptide. BPI peptide products of processes according to the invention are provided. Additionally, methods for bacterial production of fusion proteins are provided, which includes culturing a bacterial host cell transformed with a vector construct encoding the fusion protein, and isolating the expressed fusion protein. Fusion protein products of such processes are also provided.

DETAILED DESCRIPTION

Figure 1:
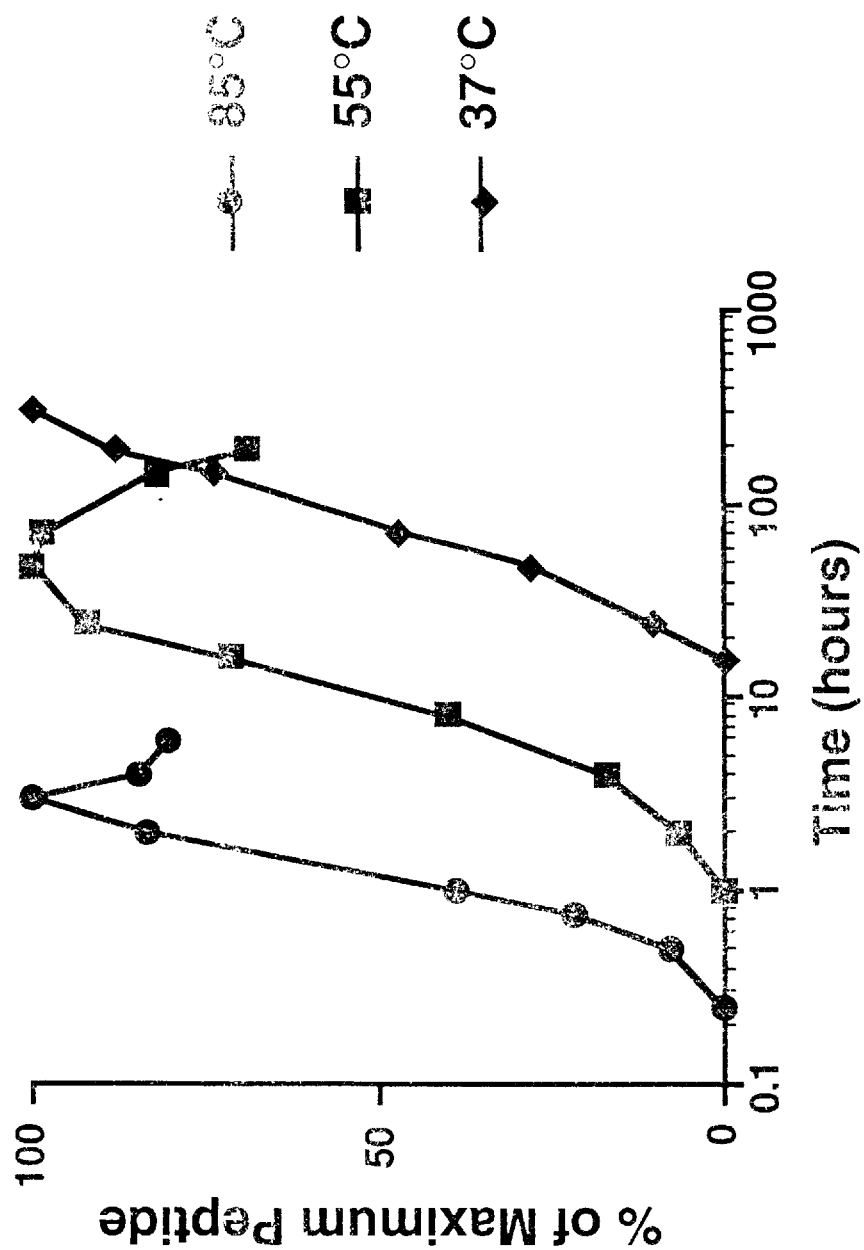
FIG. 1 shows the acid liability of the Asp-Pro peptide linker over time at various temperatures.

The present invention provides recombinant methods and compositions of fusion proteins and BPI peptides encoded by and released from such fusion proteins. Unexpectedly, such fusion proteins containing BPI-derived peptides with anti-microbial activity can be expressed in large amounts without significant proteolysis, and in some cases are actually secreted from microbial host cells. A variety of BPI-derived peptides, including those comprising the sequences listed in Table 4 (SEQ ID NOS: 1–239), may be produced by recombinant methods according to the invention. Such BPI-derived peptides having at least one or the activities of BPI (e.g., LPS binding, LPS neutralization, heparin binding, heparin neutralization or antimicrobial activity (including anti-bacterial, anti-fungal) may be useful as antimicrobial agents (including anti-bacterial and anti-fungal agents), as endotoxin binding and neutralizing agents, and as heparin binding and neutralizing agents including agents for neutralizing the anticoagulant effects of administered heparin, for treatment of chronic inflammatory disease states, and for inhibition of normal or pathological angiogenesis.

An advantage provided by present invention is the ability to produce efficiently and economically from bacterial host cells such BPI peptides. Additional advantages include the ability to obtain homogeneous peptide in large amounts via methods that are amenable to scale-up.

"BPI-derived peptide" or "BPI peptide" as used herein refers to a peptide derived from or based on bactericidal/permeability-increasing protein (BPI), including peptides derived from Domain I (amino acids 17–45), Domain II (amino acids 65–99) and Domain III (amino acids 142–169) of BPI, each peptide having an amino acid sequence that is the amino acid sequence of a BPI functional domain or a subsequence thereof and variants of the sequence or subsequence having at least one of the biological activities of BPI. As used herein, a "biological activity of BPI" refers to LPS binding, LPS neutralization, heparin binding, heparin neutralization or antimicrobial activity (including anti-bacterial and anti-fungal activity. As used herein, "cationic BPI peptide" refers to a BPI peptide with a pI>7.0, as exemplified by the peptides listed in Table 4 herein.

As used herein a "transformed bacterial host cell refers to a bacterial cell that contains recombinant genetic material or a bacterial cell that contains genetic material required for expression of a recombinant product. The genetic material may be introduced by any method known in the art including transformation, transduction, eletroporation and infection.

As used herein, a "vector construct" refers to plasmid DNA that contains recombinant genetic material which may encode a recombinant product(s) and may be capable of autonomous replication in bacteria.

"Carrier protein" as used herein refers to a protein that can be expressed in bacteria and used as a fusion partner to a linked peptide or protein. Preferred carrier proteins are those that can be expressed at high yield and when used as a fusion partner can confer high level-expression to a linked peptide or protein. A "cationic carrier protein" as used herein refers to a carrier protein having a pI (as calculated based on amino acid sequence or as measured in solution) greater than 7.0 and preferably greater than 8.0. Such preferred proteins include gelonin (pI 9.58) and the D subunit of human osteogenic protein (pI 8.18).

"Amino acid cleavage site" as used herein refers to an amino acid or amino acids that serve as a recognition site for a chemical or enzymatic reaction such that the peptide chain is cleaved at that site by the chemical agent or enzyme. Preferred amino acid cleavage sites are at aspartic acid—proline (Asp-Pro), methionine (Met), tryptophan (Trp) or glutamic acid (Glu). Particularly preferred is the Asp-Pro cleavage site which may be cleaved between Asp and Pro by acid hydrolysis.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as $rBPI_{50}$ and recombinant fragments of BPI. Co-owned, abandoned U.S. patent application Ser. No. 07/885,501 and a continuation-in-part thereof, U.S. patent application Ser. No. 08/072,063 filed May 19, 1993, now U.S. Pat. No. 5,439,807, and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 145 and 146) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Serial No. 08/212,132, filed Mar. 11, 1994, now U.S. Pat. No. 5,447,913, and corresponding PCT Application No. 95/03125, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, or dimeric forms of BPI variants. Examples of such hybrid fusion proteins and dimeric forms are described by Theofan et al. in co-owned, copending U.S. patent application Serial No. 07/885,911, and a continuation-in-part application thereof, U.S. patent application Serial No. 08/064,693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Another example of such a hybrid fusion protein is the recombinant expression product of DNA encoding amino acids 1 through 199 of BPI joined to DNA encoding amino acids 198 through 456 of LBP, designated BPI(1–199)-LBP (198–456) hybrid, is described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Serial No. 08/079,510, filed Jun. 17, 1993, the disclosures of all of which are incorporated herein by reference.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993, now U.S. Pat. No. 5,420,019, and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}\Delta$cys or rBPI$_{21}$. Other examples include dimeric forms of BPI analogs; e.g. co-owned and co-pending U.S. patent application Ser. No. 08/212,132 filed Mar. 11, 1994, now U.S. Pat. No. 5,447,913, and corresponding PCT Application No. 95/03125, the disclosures of which are incorporated herein by reference.

BPI protein products also include peptides derived from or based on BPI (BPI-derived peptides), such as those described in co-owned and copending U.S. patent application Ser. No. 08/621,259 entitled "Anti-Fungal Peptides" filed Mar. 21, 1996 WO96/08509; (PCT/US95/09262) and U.S. patent application Ser. No. 08/504,841 filed Jul. 20, 1995; WO95/19372 (PCT Application No. US94/10427) and U.S. patent application Ser. No. 08/306,473 filed Sep. 15, 1994; WO94/20532 (PCT Application No. US94/02465) and U.S. patent application Serial No. 08/209,762, filed Mar. 11, 1994; WO94/20128 (PCT Application No. US94/02401) and abandoned U.S. patent application Ser. No. 08/093,202 filed Jul. 15, 1993, the disclosures of all of which are incorporated herein by reference.

Other aspects and advantages of the present invention will be understood upon consideration of the following illustrative examples wherein Example 1 addresses construction of fusion protein expression vector constructs; Example 2 addresses expression of recombinant fusion proteins; Example 3 addresses isolation of inclusion bodies from cells expressing intracellular recombinant product; Example 4 addresses Isolation of secreted fusion protein and purification of recombinant peptide from bacterial host cell culture media; Example 5 addresses radial diffusion assays for antimicrobial activity analysis of recombinant peptides; and Example 6 addresses additional biological activity assays of recombinant peptides.

EXAMPLE 1

Construction of Fusion Protein Expression Vector Constructs

1. Bacterial Expression Vector Construct: pING3793

A bacterial expression vector which would encode a peptide fusion protein, was constructed. This vector contains a sequence for a gene encoding gelonin (see, amino acids 23 through 273 of SEQ ID NOS: 250 and 251) linked to a sequence encoding an SLT linker (see, amino acids 277 through 296 of SEQ ID NOS: 250 and 251) and a sequence encoding a peptide derived from BPI comprising amino acids corresponding to 85–99 and 148–162 of BPI (SEQ ID NO: 265). A unique BamHI site was incorporated into this vector at the junction of gelonin and peptide encoding DNA along with an encoded Asp-Pro dipeptide. For the experiments described herein, restriction and modification enzymes were purchased from New England Biolabs, Beverley, Mass. and GIBCO/BRL, Gathersberg, Md. This expression vector, pING3793, was constructed from a previously described gelonin containing vector designated pING3748 and described in U.S. Pat. No. 5,416,202 incorporated by reference in its entirety (see, e.g., Examples 10 and 2). Plasmid pING3748, which contains a gelonin gene linked to SLT, was cut with ScaI and XhoI. The vector fragment was ligated to annealed and extended oligonucleotides that encoded the BPI-derived peptide. The oligonucleotides encoding the BPI-derived peptide were:

5'-
GCTATCTGCGCATTGGATCCGATCAAAATCTCGGGTAAATGGAAGGC

CCAGAAACGCTTTCTGAAAAAGTCGAAAGTG-3'   SEQ ID NO: 240 and

5'-
GCGGGCTCTCGAGCTTTAAATCTTTTTATGAAACAGCTGGATCAGCCA

ACCCACTTTCGACTTTTTCAGAAAGCG-3   SEQ ID NO: 241

16 μg of each oligo were annealed in 10 mM TRIS, pH 8, 100 mM NaCl, 0.1 mM EDTA. Annealed oligos were extended with AmpliTaq® (Perkin Elmer, Norwalk, Conn.) in a 50 μL reaction containing standard PCR reagents in a Gene Amp® kit (Perkin Elmer, Norwalk, Conn.) according to the manufacturer's instructions) for 10 minutes at 72° C. The extended DNA fragment was purified on a Chroma-spin 30 column (Clonetech, Palo Alto, Calif.) and digested with FspI and XhoI. The purified DNA fragment was ligated to the pING3748 vector fragment. The ligated DNA was used to transform E. coli MC 1061. A candidate clone containing the DNA insert was identified by restriction analysis. The sequence of the fusion protein encoded by pING3793 is shown in SEQ ID NOS: 250 and 251.

2. Bacterial Expression Vector Construct: pING3795

An expression vector construct was prepared from pING3793 that contained a gelonin gene (see amino acids 23 through 273 of SEQ ID NOS: 250 and 251) linked to a BPI-derived peptide comprising amino acids 85–99 and 148–162 of BPI (SEQ ID NO: 265) but that lacked the SLT region described above. To accomplish this, DNA segments from three plasmids were cloned together. Plasmid pING3825 described in U.S. Pat. No. 5,416,202, incorporated by reference (see, e.g., Example 2), which encodes a recombinant gelonin, was digested with NcoI and HindIII. The vector fragment containing the 5'-end of this gelonin gene was purified. Plasmid pING3755 described in U.S. Pat. No. 5,416,202 (see, e.g., Example 10) incorporated by reference, was cut with EagI, treated with T4 polymerase to fill in the 5'-overhang, and digested with NcoI. The approximately 650 bp DNA fragment was purified. Plasmid 3793 was digested with FspI and HindIII, and the approximately 175 bp DNA fragment was purified. The three isolated DNA fragments were ligated to generate pING3795. The ligated DNA was used to transform $E.$ $coli$ MC 1061. A candidate clone containing the correct DNA insert was identified by restriction analysis and the DNA sequence of the candidate clone, pING3793, was verified by sequencing with Sequenase™ (US Biochemical, Cleveland, Ohio). A candidate clone containing the correct DNA insert was identified by restriction analysis. The sequence of the fusion protein encoded by pING3795 is shown in SEQ ID NOS: 252 and 253.

3. Bacterial Expression Vector Construct: pING3353

The DNA segment encoding a BPI-derived peptide comprising amino acids 85–99 and 148–162 of BPI (SEQ ID NO: 265) was cloned onto the 3'-end of a gene encoding subunit D of a human osteogenic protein ("Bone D") protein vector (see, amino acids 23 through 161 of SEQ ID NOS: 248 and 249) to prepare a vector construct encoding a peptide fusion protein. This vector construct, pING3353, was prepared as described below and the vector encodes a Bone D protein, a Asp-Pro dipeptide, a BPI-derived peptide segment, and contains the unique BamHI restriction site (See, SEQ ID NOS: 254 and 255).

The Bone D gene described above linked to a pel B leader sequence (see amino acids 1 through 161 of SEQ ID NOS: 248 and 249), as resident on plasmid pING3913, contains a BfaI restriction site at the 3'-end of the coding region. Plasmid pING3913 encodes a gene encoding subunit D of human osteogenic protein that is described in U.S. Pat. No. 5,284,756 incorporated by reference in its entirety (see Example 9; FIG. 6 and SEQ ID NO: 2). Digestion of pING3913 with BfaI followed by treatment of the 5'-overhang with mung bean nuclease generates a blunt end which encodes up to and including the last amino acid of the Bone D gene, which is amino acid 139 (histidine). pING3913 was cut with BfaI, treated with mung bean nuclease and then cut with EcoRI. The approximately 550 bp DNA fragment encoding Bone D was then purified. Plasmid pING3793 (see Section 1 above) was cut with FspI and HindIII and the DNA segment containing the BamHI site and encoding an Asp-Pro dipeptide and a BPI-derived peptide (approximately 175 bp) was purified. These two DNA fragments were cloned into an $E.$ $coli$ expression vector containing an Ara B expression system (e.g., pING3737/ATCC 69009; pING3746/ATCC 69008; pING3747/ATCC 69101; pING3754/ATCC 69102; pING3758/ATCC69103; pING3759/ATCC 69104; pING3336/ATCC69331; pING4644/ATCC 69332; pING4629/ATCC 69333); see U.S. Pat. No. 5,416,202) which had been digested with EcoRI and HindIII to generate pING3353. The ligated DNA was used to transform $E.$ $coli$ MC1061. A candidate clone containing the correct DNA insert was identified by restriction analysis. The DNA sequence at the junction of the Bone D gene and the peptide segment of pING3353 was verified by DNA sequencing with Sequenase™ (US Biochemical, Cleveland, Ohio).

4. Intermediate Vector Construct: pING3354

DNA encoding four BPI-derived peptides were cloned into a plasmid vector as fusions to the Bone D gene. Degenerate oligonucleotides were synthesized which could encode these peptides. These oligonucleotides were degenerate at two positions and could encode four possible peptides with amino acids F, A, S and V at the position corresponding to residue 153 in BPI.

The two oligos:

5'-GATCCGAAGTCTAAAGTGGGG[G/T][C/T]CCTGATCCAGCTGTTCCACA

AAAAGTAAAGC-3'     SEQ ID NO: 242 and

5'-TCGAGTCTTACTTTTTGTGAAGCAGCTGGATCAGG[G/A][C/A]CCCCAC

TTTAGACTTCG-3'     SEQ ID NO: 243 were synthesized and purified on a 10% acrylamide gel. Approximately 1 μg of each was annealed in 10 mM TRIS, pH 8, 100 mM NaCl, 0.1 mM EDTA. Plasmid pING3353 (see Section 3 above) was cut with EcoRI and BamHI, and the approximately 550 bp fragment containing the Bone D gene was purified. The plasmid pIC100, a derivative of pBR322, and which includes the leader sequence of the $E.$ $carotovora$ pel B gene, described in U.S. Pat. No. 5,416,202 (see, e.g., Example 10) incorporated by reference, was cut with EcoRI and XhoI and the vector fragment was purified. The annealed oligos were ligated to the digested pING3353 and pIC100 to generate four plasmids containing cloned peptide fusions. The ligated DNA was used to transform $E.$ $coli$ MC1061. Candidate clones containing a DNA insert were identified by restriction analysis. The plasinid encoding a peptide fusion protein with alanine at the position in the peptide corresponding to residue 153 in BPI was designated pING3354. The plasmid encoding a peptide fusion protein with serine at the position in the peptide corresponding to residue 153 of BPI was designated pING3355. The plasmid encoding a peptide fusion protein with valine at the position in the peptide corresponding to residue 153 in BPI was designated pING3356. The plasmid encoding a peptide fusion protein with phenylalanine at the position in the peptide corresponding to residue 153 in BPI was designated pING3357. Plasmid pING3354 was distinguished by restriction analysis by a unique ApaI site at the position of the encoded alanine. The DNA sequences of all four peptide-encoding plasmids were verified by DNA sequence determination with Sequenase™ (US Biochemical, Cleveland, Ohio). The sequence of the fusion protein encoded by plasmid pING3354 is shown in SEQ ID NOS: 256 and 257. The sequences of the fusion proteins encoded by pING3355, pING3356, and pING3357 are identical to the fusion protein shown in SEQ ID NO: 257 except that the residue corresponding to 153 in BPI is serine, valine and phenylalanine, respectively.

5. Bacterial Expression Vector Construct: pING3797

The DNA encoding the sequence of a BPI-derived antifungal peptide previously designated as XMP.36 from intermediate vector pING3354 was cloned onto the 3'-end of a gelonin gene. The resultant plasmid, pING3797, which encodes the Asp-Pro dipeptide between the gelonin and peptide gene segments was prepared as follows.

5'-ACTTGGGCCCCTACCTTGGATTTTGGGTCCTTTTTGTGGAACAGCTG-3' SEQ ID NO: 244
and
5'-TGG AAC GAT AAA TGC CCA TG-3' SEQ ID NO: 245

Plasinid pING3825, which encodes recombinant gelonin, was digested with NcoI and XhoI, and the vector fragment containing the 5'-end of the gelonin gene was purified. Plasmid pING3795 was digested with NcoI and BamHI, and the approximately 650 bp fragment containing the 3'-end of the gelonin gene as purified. Plasmid pING3354 was cut with BamHI and XhoI. These three DNA fragments were ligated together to generate pING3797 encoding the gelonin peptide fusion protein. The ligated DNA was used to transform E. coli MC 1061. Candidate clones containing the correct DNA inserts were identified by restriction analysis. The sequence of the fusion protein encoded by plasmid pING3797 is shown in SEQ ID NOS: 258 and 259.

6. Bacterial Expression Vector Construct: pING3796

The Bone D gene fused to the DNA encoding the BPI-derived antifungal peptide from intermediate vector pING3354 was cloned into a bacterial expression vector. Plasmid pING3354 was cut with EcoRI and XhoI and the approximately 610 bp DNA fragment encoding the entire Bone D and peptide sequences was purified. This DNA fragment was cloned into the vector fragment of pING3217 that had been cut with EcoRI and XhoI and purified. This vector fragment is identical to the vector fragment obtained from pING3737/ATCC 69009 (or alternatively, pING3746/ATCC 69008; pING3747/ATCC 69101; pING3754/ATCC 69102;; pING3758/ATCC69103; pING3759/ATCC 69104; pING3336/ATCC69331; pING4644/ATCC 69332; and pING4629/ATCC 69333) cut with EcoRI and XhoI. The ligated DNA was used to transform E. coli MC1061. Candidate clones containing the correct DNA inserts were identified by restriction analysis. The resultant plasmid was pING3796. The sequence of the fusion protein encoded by plasmid pING 3796 is shown in SEQ ID NOS: 260 and 261.

7. Bacterial Expression Vector Constructs Encoding Bone D Fusions And Repeat Units of a BPI-Derived Peptide: pING3359, pING3360, pING3361, and pING3362

Plasmid pING3796 encodes a single peptide segment linked to the 3'-end of Bone D with an encoded Asp-Pro dipeptide in between (see SEQ ID NOS: 260 and 261). Several similar expression vectors were constructed that contained repeat units of this peptide segment separated by Asp-Pro encoding segments.

To construct the repeat units, two oligonucleotide primers were synthesized and used to amplify the Bone D and peptide-encoding DNA sequences. The resulting PCR product was cut with ApaI, and a 48 bp peptide encoding unit was purified. This DNA fragment was self ligated under conditions where the repeat units containing 2, 3, 4, and 5 peptide-encoding segments were the predominant products. These ligation products were purified on an agarose gel and ligated into the unique ApaI site present in pING3354 at the position encoding the amino acid corresponding to residue 153 in BPI. Candidate clones containing 2–5 repeats units of the desired peptide segment were identified by restriction analysis, and their DNA sequences were verified directly with Sequenase™ (US Biochemicals, Cleveland, Ohio). The repeat containing segments were then cloned into a bacterial expression vector in a manner analogous to that described above for the construction of pING3796 from pING3354.

Specifically, two oligonucleotide primers were synthesized:

and pING3354 was amplified with these primers. The approximately 550 bp amplified DNA fragment was cut with ApaI, and the 48 bp DNA fragment was purified on an agarose gel. Approximately 1 μg of 48 bp fragment was ligated in a 30 μL reaction with 5 U T4 ligase. Three 10 μL aliquots were removed at 0.5, 3 and 15 minutes and added into 2 μL of 60 mM EDTA to stop the ligation reaction. The three samples were then mixed together, and the ligation products in the size range expected for 2 to 5 repeat units were purified on an agarose gel. Plasmid pING3354 was cut with ApaI, and the DNA was dephosphorylated with Calf intestinal alkaline phosphatase. The 48 bp DNA repeat units were ligated to the pING3354 vector and used to transform E. coli MC1061. The resultant clones were analyzed by restriction analysis. Clones containing 2, 3, 4 and 5 repeat units were identified, and the DNA sequence of the entire repeat insert was sequenced with Sequenase™. Each clone was digested with EcoRI and XhoI. These DNA fragments were ligated into the plasmid vector pING3217 that had been digested with EcoRI and XhoI. The resultant plasmids containing 2, 3, 4, and 5 repeat units of the peptide sequence were designated pING3359, pING3360, pING3361, and pING3362, respectively. The sequences of the fusion proteins encoded by pING3359 is shown in SEQ ID NOS: 262 and 263.

8. Alternative Preparation of Vector Constructs

The expression vectors encoding peptide fusion proteins as described above could be alternatively made by cutting pING3737/ATCC 69009 (or any of pING3746/ATCC 69008; pING3747/ATCC 69101; pING3754/ATCC 69102; pING3758/ATCC69103; pING3759/ATCC 69104; pING3336/ATCC6933 1; pING4644/ATCC 69332; pING4629/ATCC 69333) with EcoRI and XhoI and purifying the vector fragment, then preparing a synthetic DNA segment having a sequence encoding a pel B leader (see, e.g., amino acids 1–22 of SEQ ID NOS: 246 or 248) then preparing a synthetic DNA segment encoding a gelonin-peptide or Bone D-peptide fusion protein, for example, as shown in SEQ ID NOS: 250, 252, 254, 258 260 or 262 described herein.

EXAMPLE 2

Expression of Recombinant Fusion Proteins

1. Lab Scale Production Process

Expression of a recombinant product under control of the araB promoter was evaluated as follows. Expression vector constructs are transformed into E. Coli E104 (deposited as ATCC 69009; ATCC 69008; ATCC 69101; ATCC 69102;

ATCC69103; ATCC 69104; ATCC 69331; ATCC 69332; ATCC 69333, each containing a gelonin-encoding plasmid) and bacterial cultures were grown at 37° C. in TYE medium (15 g Tryptone, 10 g Yeast Extract, 5 g NaCl per liter) supplemented with 15 μg/mL of tetracycline to an $OD_{600} \approx 0.4$. L-arabinose from a 20% W/V solution was added to a final concentration of 0.1%. The bacterial culture was then incubated for up to 16 hours post-induction at 37° C. Secreted products were detected directly in the cell-free culture supernatant. Cells were separated by centrifugation, and culture supernatants were filtered with a 0.2 m Acrodisc filter (Gelman) and stored at 4° C. Recombinant product was detected in the culture supernatant by ELISA or analyzed on a polyacrylamide gel. Recombinant proteins that remain associated with the cellular fraction were evaluated directly by SDS-PAGE of resuspended cell pellets.

2. Scale Up Fermentation Process

A bacterial culture containing the product expression vector was inoculated into 100 mL of GMM culture medium described below and grown at 32° C. to approximately 200 Klett Units then inoculated into a 35 L fermenter. The final volume of the fermenter was approximately 10 liters or 20 titers containing minimal salts medium with glycerol as a carbon source (Glycerol Minimal Media, GMM). For a 10 L run, the fermenter vessel was autoclaved with 7.35L GMM final volume containing:

| | |
|---|---|
| $(NH_4)_2SO_4$ | 101 g |
| $KH_2PO_4$ | 13.2 g |
| $K_2HPO_4$ | 118.7 g |
| $MgSO_4.7H_2O$ | 2.3 g |
| $H_3PO_4$ (Conc.) | 24.8 mL |
| Antifoam | 0.8 mL |
| Biotin | 0.01 g |
| Yeast Extract | 38.8 g |
| Glycerol | 155 g | to which a filter sterilized solution in approximately 200 mL was added prior to bacterial inoculation:

| | |
|---|---|
| $CaCl_2.2H_2O$ (10% w/v) | 7.75 mL |
| Trace D solution* | 129 mL |
| Thiamin HCl (10% w/v) | 0.8 mL |
| Nicotinic Acid (1% w/v) | 15.5 mL |
| *Trace D solution (filtered): | |
| $FeCl_3.6H_2O$ | 6.480 g |
| $ZnSO_4.7H_2O$ | 1.680 g |
| $MnCl_2.4H_2O$ | 1.200 g |
| $Na_2MoO_4.2H_2O$ | 0.576 g |
| $CuSO_4.5H_2O$ | 0.240 g |
| $COCl_2.6H_2O$ | 0.240 g |
| $H_3BO_3$ | 0.720 g |
| $H_3PO_4$ (Conc.) | 96.0 mL |
| $H_2O$ (Batch Volume) | 2.000 L |

The inoculated fermenter was maintained at pH 6.0 and 32° C. with 10 L/min air and agitation at 1000 rpm. When nutrients became limiting (as judged by an increase in DO to roughly 100%), the culture was fed with additional nutrients until the culture reached an optical density ($OD_{600}$) of about 40–100 (DO is kept at approximately 20%). Specifically, the culture was fed with the first AI (After Inoculation) feed:

| 1st AI feed: | |
|---|---|
| Autoclaved ingredients: | |
| Glycerol | 1960 g |
| $MgSO_4.7H_2O$ | 29.4 g |
| Biotin | 0.026 g |
| $H_2O$ (Batch volume) | 2.800 L |
| Filtered ingredients: | |
| $CaCl_2.2H_2O$ (10% w/v) | 98.1 mL |
| Thiamine HCl (10% w/v) | 9.8 mL |
| Nicotinic Acid (1% w/v) | 19.7 mL |

The culture was induced by gradient induction at OD of approximately 40–100 with the second feed containing the inducing agent L-arabinose. Specifically, the second AI feed was:

| 2nd AI feed: | |
|---|---|
| Autoclaved ingredients: | |
| Glycerol | 420 g |
| $MgSO_4.7H_2O$ | 6.3 g |
| Biotin | 0.005 g |
| Arabinose | 50 g |
| $dl-H_2O$ (Batch volume) | 0.6 L |
| Filtered ingredients: | |
| $CaCl_2.2H_2O$ (10% w/v) | 21 mL |
| Thiamine HCl (10% w/v) | 2.1 mL |
| Nicotinic Acid (1% w/v) | 4.2 mL |

The culture was harvested 20 to 36 hours post induction.

The cells were separated from the culture supernatant with a 0.2 μm Microgon Hollow Fiber cartridge (10 ft.$^2$). The cell paste obtained was processed according to Example 3 below for the isolation of inclusion bodies from cells expressing an intracellular recombinant fusion protein product. Alternatively, for expressed and secreted products, the cell-free fermentation broth was concentrated and diafiltered with 10 mM sodium phosphate buffer pH 7.0 using a DC 10 with a S10Y10 Amicon cartridge. The concentrated culture medium containing the secreted recombinant product was in a volume of approximately 3 liters. The concentrated medium was processed according to Example 4 below for the isolation of recombinant fusion proteins and purification of recombinant peptides.

EXAMPLE 3

Isolation of Inclusion Bodies from Cells Expressing Intracellular Recombinant Product Experiments were conducted to express a fusion protein comprised of Bone D and a BPI-derived peptide linked by an Asp-Pro peptide bond. Cell paste from E. coli cultured as described in Example 2 for the expression of a fusion protein of Bone D with a BPI-derived peptide (e.g., pING3353) was suspended in 100 mM Tris-HCl pH 8.0, 5 mM EDTA (7 mL/g cell paste) and incubated on ice for 10 minutes. Lysozyme (10 mg/mL in 100 mM Tris-HCl pH 8.0, 5 mM EDTA) was added to give a final concentration of 10 mg lysozyme/g cell paste, and the sample was incubated on ice until lysis occurred (i.e., when the solution became very viscous). Lysis typically occurred within about 10 minutes. The mixture was sonicated with 3 or 4 ten second pulses at the highest setting using a Sonic U sonicator (B. Braun Biotech Inc., Allentown, Pa.). The inclusion bodies were pelleted by centrifugation at 22,000 g for 40 minutes. A series of washes with Triton X-100, then 60 mM HCl, and then water followed. First the inclusion body pellet was washed by resuspending in 100 mM Tris-HCl, pH 8.0, 5 mM EDTA, 1% Triton X-100, followed by centrifugation at 22,000 g for 40 minutes. The next washes were done additionally with 60 mM HCl and water. For each wash [at 4° C], the resuspension of the inclusion bodies was done with a Polytron® (Brinkmann Instruments, Westbury, N.Y.). The acid wash was done to remove lysozyme from the inclusion body pellet. No recombinant peptide was released (i.e., no appearance in either the supernatant or pellet after washing the inclusion body pellet with HCl) indicating that the acid wash conditions were mild enough such that cleavage of the Asp-Pro bond in the fusion protein did not occur. Washing the inclusion body pellet with water instead of acid did not remove lysozyme.

Samples were analyzed by SDS-PAGE using 10–20% Tricine gels (Novex, San Diego, Calif.). Samples were prepared by boiling in SDS loading buffer with reducing agent for 5 minutes. Samples were also analyzed by HPLC, using a Beckman instrument with Shimadzu auto injector and a Vydac C18 (#218TP54) column. Solvent A was 10 % acetonitrile/0.05 % TFA; solvent B was 90% acetonitrile/ 0.05% TFA. The column was run with an 18–40% B gradient over 20 minutes, at a flow rate of 1 mL/minute with peptide detection at 229 nm.

The fusion protein of Bone D and peptide was designed with an Asp-Pro peptide bond at the junction so the peptide might be liberated with acid treatment. Peptide bonds of aspartyl residues may be cleaved in dilute acid at rates at least 100 times greater than other peptide bonds and aspartyl-prolyl bonds are the most labile of the aspartyl peptide bonds. It was not known whether the inclusion bodies would need to be solubilized in order for this reaction to be effective on the fusion protein. Even if the acid was effective on the inclusion bodies without solubilization and the Asp-Pro bond of the fusion protein was cleaved, it was not known whether the free peptide and/or the Bone D protein would become soluble.

The acid hydrolysis of the inclusion body pellet was done with 30 mM or 60 mM HCl, but at a much higher temperature and for a longer period of time than the acid wash of inclusion bodies. Conditions of temperature and incubation time sufficient to cleave the Asp-Pro bond in the fusion protein to liberate free peptide were determined by experimentation as follows.

Several conditions were tested for achieving complete cleavage of the Asp-Pro bond. At 55° C. using 60 mM HCl, complete cleavage occurred by about 48 hours. This was evident from SDS-PAGE analysis; after 48 hours the fusion protein band had nearly disappeared as it was converted into Bone D and peptide. Samples were analyzed by SDS-PAGE and the gel results from the pellet after acid hydrolysis indicated that Bone D protein surprisingly remained insoluble after the 60 mM HCl treatment. This result was advantageous because it allowed isolation of the cleaved peptide from the acid supernatants. Specifically, SDS-PAGE analysis of the supernatants after acid hydrolysis revealed that the peptide was found soluble in the supernatant after cleavage from the insoluble fusion protein. If the inclusion body pellet was not washed with acid to remove lysozyme as described above, a 14 kD lysozyine band was observed in the inclusion body pellet by SDS-PAGE.

SDS-PAGE analysis revealed the time-dependent generation of peptide in the supernatant during acid hydrolysis. In an attempt to reduce the time required for complete hydrolysis of the Asp-Pro bond in the fusion protein, higher temperature was used. Peptide was liberated from the fusion protein over time at 85° C. using 60 mM HCl. The reaction was complete between 2 and 4 hours since the fusion protein was not present in the 4 hour sample analyzed by SDS-PAGE. The accumulation of peptide in the supernatant was observed over time, however, after 2 hours a slight decrease in the peptide concentration was observed presumably due to peptide hydrolysis and/or deamidation. Acid hydrolysis was also conducted at higher temperature but with a lower HCl concentration of 30 mM. Under these conditions at 85° C. the reaction was complete at 4 hours. Fusion protein was not present at 4 hours by SDS-PAGE analysis. By 6 hours, the peptide concentration began to decrease presumably due to peptide hydrolysis and/or deamidation.

Figure 2:
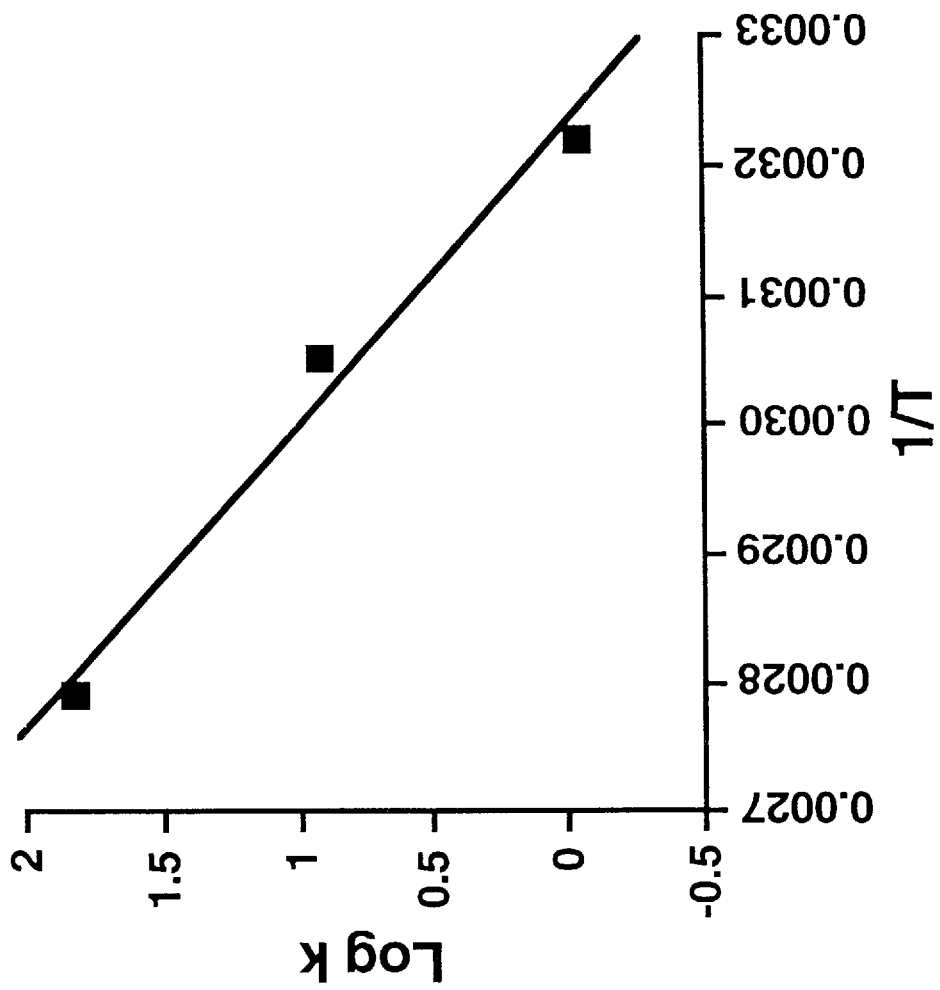
FIG. 2 shows an Arrhenius plot for the hydrolysis of fusion protein.

FIG. 1 shows the acid liability of the Asp-Pro peptide linker over time at various temperatures. FIG. 2 shows an Arrhenius plot for the hydrolysis of fusion protein, demonstrating that the rate of hydrolysis is proportional to the temperature.

Additional experiments were performed to investigate conditions for complete acid cleavage of fusion protein from inclusion bodies with 30 mM HCl at 85° C. but using various weight/volume concentrations of inclusion bodies. For scale-up processes, it was desirable to be able to use high weight/volume concentration of inclusion bodies, however, in the experiments described above and in previously published experiments with a very different recombinant fusion protein [REF], the highest weight/volume concentrations used for cleavage were 10% (i.e., 10 g wet/weight per 100 mL volume) and 6% (i.e., 6 g per 100 mL), respectively.

Figure 3:
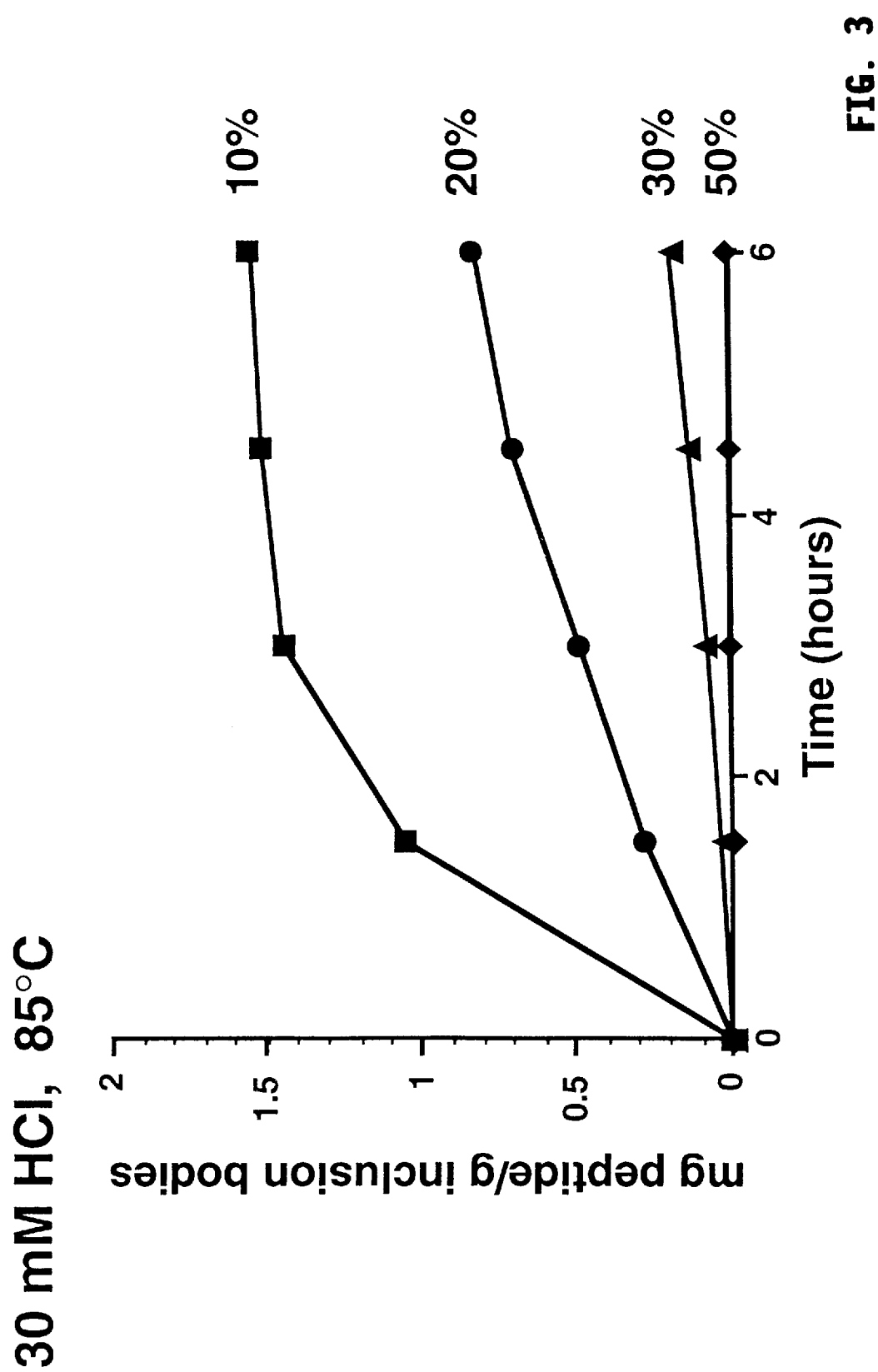
FIG. 3 shows acid cleavage rates of various acid-treated inclusion body suspensions.

The results shown in FIG. 3 demonstrate while maximal acid cleavage was achieved with a 10% weight/volume at 85° C. in 4–6 hours, when the weight/volume concentrations of inclusion bodies were increased to 20%, 30% and 50%, the reaction rate decreased significantly. In particular, at the 30% and 50% concentrations little or no peptide was released by acid hydrolysis of the inclusion bodies. When the pH of each of the acid-treated inclusion body suspensions was measured, it was discovered that the pH of the suspensions varied dramatically (pH 2.6, 3.7, 4.4 and 5.1 for acid-treated inclusion body suspensions of 10%, 20%, 30% and 50%, respectively.

Figure 4:
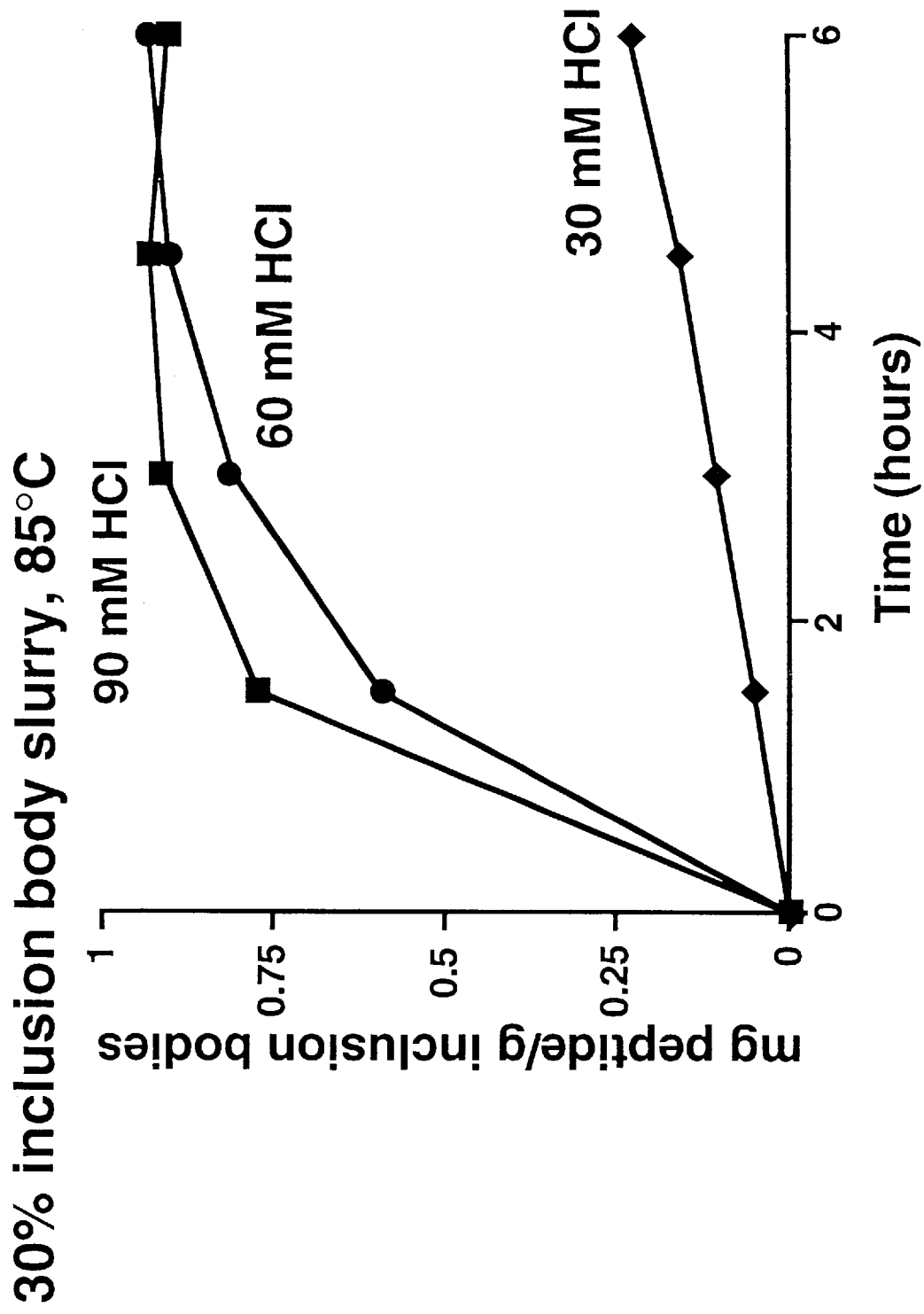
FIG. 4 shows maximal peptide release achieved with 60 mM and 90 mM HCl treated suspensions.

In order to test whether the variation in pH was the cause of the decreased release, and if so what pH range might be critical for achieving complete hydrolysis, additional experiments were performed using 30% inclusion body suspensions using 30 mM, 60 mM or 90 mM HCl. As shown in FIG. 4, maximal peptide release was achieved with the 60 mM and 90 mM HCl treated suspensions. The pH of the 30 mM, 60 mM and 90 mM treated suspension was 3.5, 2.4 and 1.5, respectively. The conclusion from these experiments was that obtaining and maintaining a low pH suspension of inclusion bodies was critical to achieving maximal peptide cleavage and release. Presently preferred conditions for acid hydrolysis include titration to pH 2.2 with concentrated HCl using suspensions that are greater than 10% in weight/ volume concentration, preferably 30%. Having discovered that achieving a constant pH of $\leq 2.6$ is important for efficient and complete acid hydrolysis for the release of peptide, high weight/volume concentrations (i.e., >10–50%) of inclusion bodies may be routinely and efficiently processed.

For the purification of recombinant peptides from *E. coli*, three column separation steps were utilized to achieve sufficiently low levels of impurities (e.g., protein, endotoxin, and DNA). After acid hydrolysis, the supernatant was neutralized. However, in initial experiments, a precipitate formed which included some of the peptide. This precipitation could be avoided by addition of >5 M urea.

For initial attempts to work out a process, 30 g of cell paste were utilized. SP sepharose was chosen for the first step. As a second column step, the hydrophobic interaction resin butyl sepharose was chosen. Gel filtration chromatography with Superdex 30 (Phannacia) was chosen as the last step. As shown in Table 1, the overall recovery was 10.7%, with most of the loss occurring at the SP Sepharose step. Mass spectrum analysis of the peptide isolated from this purification showed a mass (3735) consistent with the predicted mass (3735.7) indicating an intact amino and carboxyl terminus. The antimicrobial activities of the purified peptide were assayed as described in Example 5, and found to be active.

Based on results from additional experiments, a purification process with 30 g of cell paste was tested which incorporated an ultrafiltration step in 5M urea followed by a CM Spherodex column. As shown in Table 2, the recovery for this purification scheme was 31 %. Most of the loss occurred at the filtration step.

TABLE 1

| Sample | Volume (mL) | % Recovery by HPLC | % Recovery From Previous Step |
| --- | --- | --- | --- |
| Supernatant from HCl treatment | 202 | 100.0 | |
| SP Sepharose flow-through | 284 | 0.0 | |
| SP Sepharose eluate | 111 | 13.2 | 13.2 |
| SP Sepharose strip | 184 | 37.0 | |
| Butyl Sepharose flow-through | 377 | 0.0 | |
| Butyl Sepharose eluate | 31 | 11.9 | 89.9 |
| Butyl Sepharose strip | 0 | 0.0 | |
| Superdex 30 pool (final) | 20 | 10.7 | 89.8 |

TABLE 2

| Sample | Volume (mL) | % Recovery by HPLC | % Recovery From Previous Step |
| --- | --- | --- | --- |
| Supernatant from HCl treatment | 200 | 100.0 | |
| 100K flow through | 400 | 41.8 | 41.8 |
| CM Spherodex flow through | 440 | 0.0 | |
| CM Spherodex eluate | 67 | 33.1 | 79.2 |
| CM Spherodex strip | 33 | 0.0 | |
| Butyl Sepharose eluate | 37 | 29.6 | 89.5 |
| Superdex 30 pool (final) | 19.5 | 30.9 | 104.4 |

Figure 5:
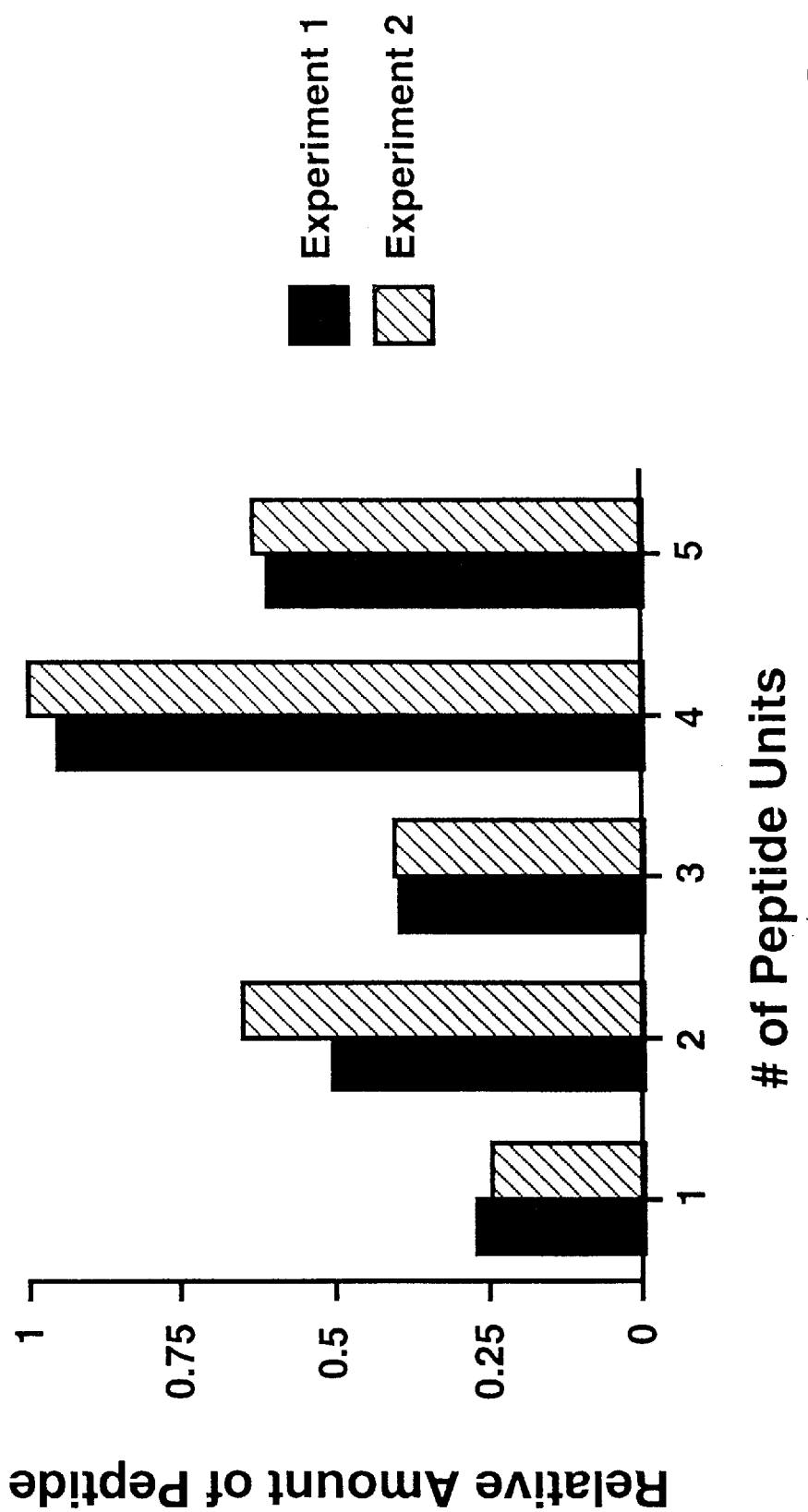
FIG. 5 shows the highest yield of product from pING3360 with four peptide repeat units.

Additional experiments were conducted to express a fusion protein comprising Bone D and multiple repeats of a BPI-derived peptide linked by Asp-Pro peptide bonds. For these experiments, five fermentation batches in a 35 liter vessel were grown, each producing a different fusion protein. Specifically, five fermentation batches were grown in a 35 L fermenter as described in Example 2 of E. coli E104 cells containing plasmids pING3796 (single peptide construct), pING3359 (2 peptide construct), pING3361 (3 peptide construct), pING3360 (4 peptide construct) and pING3362 (5 peptide construct), thus, increasing numbers of peptide units were produced in each batch. In an experiment, one grain of cell paste from each fermentation batch was lysed by lysozyme/EDTA followed by sonication as described above. The inclusion bodies were isolated by centrifugation and suspended in 30mM HCl for 3.5 hours at 85 ° C. Peptide in the supernatant was quantitated by HPLC. Duplicate aliquots from each fermentation were analyzed. Results as shown in FIG. 5 revealed that the product from pING3360 with four peptide repeat units had the highest yield.

Mechanical description of the c ells in the fermentation batches described above was investigated as an alternative to the procedure described in this Example 3, using iysozyme/EDTA followed by sonication. Mechanical methods for cell disruption are well suited for large scale applications, thus the use of a Microfluidizer® (Microfluidics International Corporation, Newton, Mass., model M-110Y) for large scale cell lysis was investigated. With this device, product is driven by air pressure through microchannels at high velocity. The process stream is split and then reunited allowing the cells to collide. The resulting shear and cavitation forces disrupt the cells. Greater than 95% lysis was achieved with a single pass. Process times were about 30 minutes for 10 liters of resuspended cell paste with a density of 10% suspended solids. Inclusion bodies were isolated by centrifugation at 11,000 g for 1 hour.

Complete hydrolysis of aspartyl prolyl bonds was achieved by suspending inclusion bodies obtained from each of the 5 fermentation batches in 30 mM HCl [10%, weight/volume] and incubating at 85° C. for 4–5 hours as described above. Alternatively, inclusion bodies could be resuspended in water followed by acid addition. Released peptide was soluble in the aqueous environment. The acid hydrolysate was neutralized by adding sodium citrate to buffer the solution and then NaOH to adjust the pH to 6.0. Using this mechanical description method, no precipitation was observed with neutralization after acid hydrolysis as was seen with the lysozyme/EDTA/sonication method. Numerous E. coli protein impurities in the acid hydrolysate were removed by subsequent purification steps.

Experiments were done to determine the optimal elution conditions for the two columns used in the purification process. For the CM Sepharose column, sample was loaded and the column was step eluted with increasing concentrations of NaCl in 10 mM citrate buffer at pH 3.0. Most of the peptide eluted at 40 mM NaCl with a small amount eluting at 80 mM NaCl. Therefore, the elution buffer for CM Sepharose was chosen as 10 mM citrate, 80 mM NaCl, pH 3.0. Elution conditions for the butyl sepharose column were determined by similar experiments. A butyl sepharose column loaded with peptide was step eluted with decreasing concentrations of ammonium sulfate in 10 mM sodium phosphate buffer at pH 7.0. Relatively pure peptide eluted at ammonium sulfate concentrations down to 1.1 M. Impurities began to elute with the peptide at 0.8 M ammonium sulfate. In these experiments, the optimal ammonium sulfate concentration for achieving pure peptide was between 0.8 M and 1.1 M.

When peptide was purified from 5 grams of inclusion bodies using these optimized elution conditions, SDS-PAGE analysis revealed that the pellet after acid hydrolysis contained predominantly Bone D and very little fusion protein indicating that the hydrolysis was nearly complete. Numerous protein impurities were present in the acid hydrolysate. A significant purification was achieved on the CM sepharose column and after butyl sepharose there were no protein impurity bands detected by SDS-PAGE.

Purity was also assessed by HPLC analysis using a Beckman instrument with Shimadzu auto injector and a C18 (Vydac, #218TP54) reverse phase column. Solvent A was 10 % acetonitrile/0.1% TFA; solvent B was 90% acetonitrile/

0.1% TFA. The C18 column was run with a 15%–35% B gradient over 20 minutes, with a 1 mL/minute flow rate. Peptide detection at 229 nm. The deamidated form of the peptide was present in the acid supernatant at levels of approximately 5% and was not removed by the purification process.

As shown in Table 3, recovery after the CM sepharose and butyl sepharose columns was 87.2% and 43.5%, respectively. Recombinant peptides isolated from *E. coli* by this method tested as described in Example 5 and found to be as active in a radial diffusion assay as the comparable synthetic peptides.

In an effort to further improve the purification process, a resin which could substitute for butyl sepharose was selected for additional experiments. A CM sepharose eluate was loaded onto a Source reverse phase resin (Pharmacia) column and then eluted with a gradient of increasing acetonitrile concentration. The peptide peak was isolated and the solvent removed by evaporation in a vacuum centrifuge. Sample was resuspended in buffer and evaluated for purity by SDS-PAGE and HPLC. Purity was comparable to that obtained with a butyl sepharose column with improved yield. The yield at this column step was 98%, which was a significant improvement over the butyl sepharose column.

TABLE 3

| Sample | Volume (mL) | % Recovey |
| --- | --- | --- |
| HCl supernatant | 45 | 100.0 |
| HCl supernatant neutralized | 45 | 92.9 |
| CM sepharose flow-through | 99 | 0.0 |
| CM sepharose eluate | 47 | 87.2 |
| CM sepharose strip | 36 | 0.9 |
| Butyl Sepharose flow-through | 140 | 3.7 |
| Butyl Sepharose eluate | 45 | 43.5 |
| Butyl sepharose strip | 26 | 2.7 |

EXAMPLE 4

Isolation of Secreted Fusion Protein and Purification of Recombinant Peptide from Bacterial Host Cell Culture Media

*E. coli* E 104 cells containing pING3797 encoding a peptide-gelonin fusion protein was grown in a fermenter as described in Example 2. The secreted fusion protein was isolated from the *E. coli* fermentation broth after cell growth. The fermentation broth was separated from the bacterial cells and the cell-free fermentation broth was concentrated and diafiltered with 10 MM sodium phosphate pH 7.0 using a DC10 with an S10Y10 Amicon cartridge as described in Example 2. The concentrated culture medium was in a volume of approximately 3 liters. Diafiltered material was loaded onto a column of CM Sepharose Fast Flow (Pharmacia, Uppsala, Sweden) equilibrated in 10 mM sodium phosphate, pH 7.0. The column was eluted in 10 mM sodium phosphate, 400 mM NaCl, pH 7.0 to isolate the fusion protein. The gelonin-peptide fusion protein was approximately 70% pure and was found to be active in a radial diffusion assay as described in Example 5.

Concentrated HCl was added to the CM Sepharose eluate to a final HCI concentration of 30 mM. The sample was incubated at 85° C. for 3 hours and then neutralized by adding 500 mM sodium citrate to a final concentration of 15 mM. A precipitate which formed was removed by centrifugation and the sample was further purified by HPLC on a C 18 column. The peptide was eluted with a 15–35% gradient of 90% acetonitrile/0.05% TFA over 20 minutes at a flow rate of 1 mL/minute. The peptide peak was isolated and its identity was confirmed by N-terminal sequence analysis. The antimicrobial activity of the purified peptide was determined by radial diffusion assay as described in Example 5 below.

EXAMPLE 5

Radial Diffusion Assays for Antimicrobial Activity Analysis of Recombinant Peptides A variety of BPI-derived peptides, including those comprising the sequences listed in Table 4 (SEQ ID NOS: 1–239) may be produced by recombinant methods of the invention and tested for antimicrobial activity (both anti-fungal and anti-bacterial activity) in radial diffusion assays. Experiments were initially performed to assess the antifungal activity of the recombinantly produced peptides in a radial diffusion assay. For these experiments, *Saccharomyces cerevisiae* PS6 or *Candida albicans* SLU-1 were added at $1\times10^6$ cells per mL into 8 mL of 1/100 X Sabouraud dextrose broth in 1% agarose plus 300 mM EDTA and 0.02% Tween 20. The mixture was poured into a plate and 3.5 mM wells were made by hole punches after solidification. Samples were diluted into saline, and 5 $\mu$L samples were added to each well. The samples were incubated at room temperature for three hours and then the plates were overlayed with 8 mL of 2X Sabouraud dextrose broth in 1% agarose plus 300 mM EDTA and 0.02% Tween 20. Areas of inhibition were calculated after a 24 hour incubation at 30° C. Peptide prepared as described in Example 3 was found to be active in this assay. Fusion protein prepared as described in Example 4 was also found to be active in this assay.

To assess the antibacterial activity of the recombinantly produced peptides, additional experiments are conducted with *E. coli* J5 or *E. coli* E104 cells in a radial diffusion assay. For these experiments, cultures of *E. coli* J5 were grown overnight in TYE broth (15 g tryptone, 10 g yeast extract, 5 g NaCl per liter) and then grown to mid logarithmic phase in TEA broth media (Simon et al., *Proc. Nat'l. Acad. Sci.* (*USA*), 51:877–883 (1964)). *E. coli* J5 cells at 2–3 $\times10^5$ cells/mL were added to molten 0.8% agarose containing nutrient broth. Serial dilutions of peptides were prepared in 0.15 M NaCl. Five $\mu$l of the diluted peptides, or as a control, saline alone, were added to 3 mm wells prepared in the hardened agarose (5 $\mu$l/well). The plates were sealed with parafilm to prevent drying and incubated at 37° C. for 24 hours. Zones of inhibition were measured and the net areas of inhibition determined by subtracting the area comprising the 3 mm well from the area encompassing the 3 mm well plus the inhibition zone. Recombinantly produced peptides are assayed for antibacterial activity and compared to the equivalent synthetic peptides. When the synthetic peptides XMP.13, XMP.284, XMP.353, XMP.366, XMP.406 and XMP.407 with sequences shown in Table 4 below were assayed for antibacterial activity peptide XMP.284 exhibited the most antibacterial activity followed by XMP.13, XMP.391, XMP.366, XMP.353, XMP.406 and XMP.407 as the least bactericidal. Synthetic peptides XMP.406 and XMP.407 have the same sequences as peptides prepared from the encoded fusion protein described in Example 1, Section 7 and Example 3. Recombinant peptide prepared from pING3353 (Examples 1 and 3) was found to be active in this assay.

TABLE 4

| Peptide (SEQ ID NO:) | Peptide Amino Acid Segment |
|---|---|
| XMP.1 (1) | 19–33 |
| XMP.2 (2) | 85–99 |
| XMP.3 (3) | 73–99 |
| XMP.4 (4) | 25–46 |
| XMP.5 (5) | 142–163 |
| XMP.6 (6) | 112–127 |
| XMP.7 (7) | (90–99) × 2 |
| XMP.8 (8) | 90–99 |
| XMP.9 (9) | 95–99, 90–99 |
| XMP.10 (10 & 11) | 94–99, 90–99, 90–99 and 95–99, 90–99, 90–99 |
| XMP.10a (10) | 94–99, 90–99, 90–99 |
| XMP.10b (11) | 95–99, 90–99, 90–99 |
| XMP.11 (12) | 148–151, 153–161 |
| XMP.12 (13) | 141–169 |
| XMP.13 (14) | 148–161 |
| XMP.14 (15) | 21–50 |
| XMP.15 (16) | 85–99, A @ 85 (I) |
| XMP.16 (17) | 85–99, A @ 86 (K) |
| XMP.17 (18) | 85–99, A @ 87 (L) |
| XMP.18 (19) | 85–99, A @ 88 (S) |
| XMP.19 (20) | 85–99, A @ 89 (G) |
| XMP.20 (21) | 85–99, A @ 90 (K) |
| XMP.21 (22) | 85–99, A @ 91 (W) |
| XMP.22 (23) | 85–99, A @ 92 (K) |
| XMP.23 (24) | 85–99, A @ 94 (Q) |
| XMP.24 (25) | 85–99, A @ 95 (K) |
| XMP.25 (26) | 85–99, A @ 96 (R) |
| XMP.26 (27) | 85–99, A @ 97 (F) |
| XMP.27 (28) | 85–99, A @ 98 (L) |
| XMP.28 (29) | 85–99, A @ 99 (K) |
| XMP.29 (30) | (148–161) × 2 |
| XMP.30 (31) | 90–99, 148–161 |
| XMP.31 (32) | 148–161, A @ 148 (K) |
| XMP.32 (33) | 148–161, A @ 149 (S) |
| XMP.33 (34) | 148–161, A @ 150 (K) |
| XMP.34 (35) | 148–161, A @ 151 (V) |
| XMP.35 (36) | 148–161, A @ 152 (G) |
| XMP.36 (37) | 148–161, A @ 153 (W) |
| XMP.37 (38) | 148–161, A @ 154 (L) |
| XMP.38 (39) | 148–161, A @ 155 (I) |
| XMP.39 (40) | 148–161, A @ 156 (Q) |
| XMP.40 (41) | 148–161, A @ 157 (L) |
| XMP.41 (42) | 148–161, A @ 158 (F) |
| XMP.42 (43) | 148–161, A @ 159 (H) |
| XMP.43 (44) | 148–161, A @ 160 (K) |
| XMP.44 (45) | 148–161, A @ 161 (K) |
| XMP.45 (46) | 148–161, A @ 161 (K) |
| XMP.46 (47) | (90–99) × 2, A @ 1st 94 (Q) & 95 (K) |
| XMP.47 (48) | (90–99) × 2, A @ 2d 94 (Q) & 95 (K) |
| XMP.48 (49) | (90–99) × 2, A @ both 94 (Q) & 95 (K) |
| XMP.49 (50) | 178–191 |
| XMP.50 (51) | 178–192 |
| XMP.51 (52) | 178–193 |
| XMP.52 (53) | 178–194 |
| XMP.53 (54) | 178–195 |
| XMP.54 (55) | 21–35 |
| XMP.55 (56) | 152–172 |
| XMP.56 (57) | 85–99, K @ 94 (Q) & Q @ 95 (K) |
| XMP.57 (58) | Cys 85–99 Cys |
| XMP.58 (59) | Cys-85–99 |
| XMP.59 (60) | 85–99, A @ 90 (K) & 92 (K) |
| XMP.60 (61) | 85–99, A @ 86 (K) & 99 (K) |
| XMP.61 (62) | 85–99, F @ 91 (W) |
| XMP.62 (63) | 119–148*^ |
| XMP.63 (64) | 85–99, 148–161 |
| XMP.64 (65) | 178–193* |
| XMP.65 Rd (66) | Cys-85–99-Cys |
| XMP.65 Ox (67) | Cys-85–99-Cys |
| XMP.68 (68) | 119–148, ALA @ 132 (C)*^ |
| XMP.69 (69) | [90–99, A @ 94 (Q) & 95 (K)] × 3 |
| XMP.73 (70) | 85–99, F @ 95 (K) |
| XMP.74 (71) | 148–161, 90–99 |
| XMP.75 (72) | IKKRAISFLGKKWQK (2-mixed) |
| XMP.77 (73) | 85–99, W @ 95 (K) |
| XMP.78 (74) | 100-118* |
| XMP.79 (75) | 85–99, K @ 94 (Q) |
| XMP.81 (76) | 85–99, F @ 94 (Q) |
| XMP.82 (77) | 148–161, W @ 158 (F) |
| XMP.85 (78) | 148–161, L @ 152 (G) |
| XMP.86 (79) | 148–161, L @ 156 (Q) |
| XMP.87 (80) | 148–161, L @ 159 (H) |
| XMP.88 (81) | 85–99, F @ 94 (Q) |
| XMP.91 (82) | 148–161, F @ 156 (Q) |
| XMP.92 (83) | 148–161, K @ 156 (Q) |
| XMP.94 (84) | 148–161, F @ 159 (H) |
| XMP.95 (85) | 148–161, F @ 152 (G) |
| XMP.96 (86) | 148–161, F @ 161 (K) |
| XMP.97 (87) | 148–161, K @ 152 (G) |
| XMP.99 (88) | [90–99, W @ 95 (K)] × 3 |
| XMP.100 (89) | 148–161, K @ 152 (G) & 156 (Q) |
| XMP.101 (90) | (148–161) × 2[K @ 152 (G) & 156 (Q), F @ 159 (H) & 161 (K)] |
| XMP.102 (91) | 90–99 (F @ 95 (K)) + 148–161 L @ 156 (Q) |
| XMP.103 (92) | 85–99, W @ 94 (Q) |
| XMP.104 (93) | 148–161, S @ 156 (Q) |
| XMP.106 (94) | 148–161, T @ 156 (Q) |
| XMP.107 (95) | 148–161, W @ 159 (H) |
| XMP.108 (96) | 148–161, W @ 161 (K) |
| XMP.113 (97) | 148–161, F @ 157 (L) |
| XMP.114 (98) | KWQLRSKGKIKIFKA |
| XMP.115 (99) | 170–177*^ |
| XMP.117 (100) | 49–59* |
| XMP.118 (101) | 60–77* |
| XMP.120 (102) | 85–99, K @ 97 (F) |
| XMP.124 (103) | 148–161, K @ 152 (G), W @ 158 (F) |
| XMP.125 (104) | 148–161, Y @ 156 (Q) |
| XMP.127 (105) | 148–161, F @ 153 (W) |
| XMP.135 (106) | 148–161, K @ 153 (W) |
| XMP.136 (107) | 85–99, E @ 95 (K) |
| XMP.137 (108) | C-148–161-C |
| XMP.138 (109) | 148–161, K @ 152 (G), F @ 153 (W) |
| XMP.139 (110) | 148–161, Y @ 153 (W) |
| XMP.141 (111) | 85–99, W @ 97 (F) |
| XMP 142 (112) | 148–161, W @ 157 (L) |
| XMP.147 (113) | 85–99 K @ 96 (R) |
| XMP.149 (114) | KWKVFKKIEK + 148–161 |
| XMP.150 (115) | KWAFAKKQKKRLKR QWLKKF |
| XMP.151 (116) | 94–99, 90–99, 90–99 |
| XMP.152 (117) | 95–99, 90–99, 90–99 |
| XMP.153 (118) | (90–99) × 3 |
| XMP.161 (119) | 148–161, K @ 152 (G) & A @ 153 (W) |
| XMP.162 (120) | 90–99, 148–161, W @ 95 (K) |
| XMP.163 (121) | (90–99) × 2, W @ both 95 (K) |
| XMP.166 (122) | 148–161, V @ 153 (W) |
| XMP.167 (123) | 90–97 |
| XMP.168 (124) | C-90–101-C |

TABLE 4-continued

| Peptide (SEQ ID NO:) | Peptide Amino Acid Segment |
| --- | --- |
| XMP.169 (125) | C-90–97-C |
| XMP.170 (126) | 90–101 |
| XMP.241 (127) | 148–161, L @ 156 (Q), W @ 158 (F) |
| XMP.245 (128) | 90–99, 148–161, F @ 95 (K), W @ 158 (F) |
| XMP.249 (129) | 148–161, G @ 153 (W) |
| XMP.250 (130) | 148–161, L @ 153 (W) |
| XMP.251 (131) | 148–161, I @ 153 (W) |
| XMP.262 (132) | 148–161, N @ 156 (Q) |
| XMP.263 (133) | 148–161, E @ 156 (Q) |
| XMP.264 (134) | 148–161, D @ 156 (Q) |
| XMP.265 (135) | 148–161, R @ 156 (Q) |
| XMP.266 (136) | 148–161, K @ 152 (G), V @ 153 (W) |
| XMP.267 (137) | 148–161, K @ 152 (G), A @ 154 (L) |
| XMP.268 (138) | 148–161, V @ 153 (W), A @ 154 (L) |
| XMP.269 (139) | 148–161, K @ 152 (G), V @ 153 (W), A @ 154 (L) |
| XMP.270 (140) | (148–161) + (148–161), L @ 1st 156 (Q) |
| XMP.271 (141) | (148–161) + (148–161), L @ 2nd 156 (Q) |
| XMP.272 (142) | (148–161) + (148–161), L @ both 156 (Q) |
| XMP.273 (143) | (148–161) + (148–161), F @ 1st 156 (Q) |
| XMP.274 (144) | (148–161) + (148–161), F @ 2nd 156 (Q) |
| XMP.275 (145) | (148–161) + (148–161), F @ both 156 (Q) |
| XMP.276 (146) | 90–99, 148–161, F @ 95 (K) & 156 (Q) |
| XMP.278 (147) | 85–99, A @ 94 (Q), W @ 95 (K) |
| XMP.280 (148) | 85–99, A @ 94 (Q), F @ 95 (K) |
| XMP.282 (149) | [90–99, F @ 94 (Q) & 95 (K)] × 2 |
| XMP.283 (150) | 148–161, K @ 152 (G), F @ 153 (W), K @ 156 (Q) |
| XMP.284 (151) | 149–161, K @ 152 (G) |
| XMP.285 (152) | 149–160, K @ 152 (G) |
| XMP.286 (153) | 150–161, K @ 152 (G) |
| XMP.287 (154) | 149–159, K @ 152 (G) |
| XMP.288 (155) | 150–160, K @ 152 (G) |
| XMP.289 (156) | 151–161, K @ 152 (G) |
| XMP.290 (157) | 149–158, K @ 152 (G) |
| XMP.291 (158) | 150–159, K @ 152 (G) |
| XMP.292 (159) | 151–160, K @ 152 (G) |
| XMP.293 (160) | 152–161, K @ 152 (G) |
| XMP.294 (161) | 149–157, K @ 152 (G) |
| XMP.295 (162) | 150–158, K @ 152 (G) |
| XMP.296 (163) | 151–159, K @ 152 (G) |
| XMP.297 (164) | 152–160 K @ 152 (G) |
| XMP.298 (165) | 153–161 |
| XMP.299 (166) | 149–156, K @ 152 (G) |
| XMP.300 (167) | 150–157, K @ 152 (G) |
| XMP.301 (168) | 151–158, K @ 152 (G) |
| XMP.302 (169) | 152–159, K @ 152 (G) |
| XMP.303 (170) | 153–160 |
| XMP.304 (171) | 154–161 |
| XMP.305 (172) | 149–155, K @ 152 (G) |
| XMP.306 (173) | 150–156, K @ 152 (G) |
| XMP.307 (174) | 151–157, K @ 152 (G) |
| XMP.308 (175) | 152–158, K @ 152 (G) |
| XMP.309 (176) | 153–159 |
| XMP.310 (177) | 154–160 |
| XMP.311 (178) | 155–161 |
| XMP.312 (179) | 149–154, K @ 152 (G) |
| XMP.313 (180) | 150–155, K @ 152 (G) |
| XMP.314 (181) | 151–156, K @ 152 (G) |
| XMP.315 (182) | 152–157, K @ 152 (G) |
| XMP.316 (183) | 153–158 |
| XMP.317 (184) | 154–159 |
| XMP.318 (185) | 155–160 |
| XMP.319 (186) | 156–161 |
| XMP.320 (187) | 153–157 |
| XMP.321 (188) | 153–157 - K |
| XMP.322 (189) | 153–157 - K - K |
| XMP.323 (190) | K - 153–157 - K |
| XMP.324 (191) | K - 153–157 - K - K |
| XMP.325 (192) | K - K - 153–157 |
| XMP.326 (193) | K - K - 153–157 - K |
| XMP.327 (194) | K - K - 153–157 - K - K |
| XMP.328 (195) | Pro - (85–99) + (148–162)* |
| XMP.330 (196) | 153–156 |
| XMP.331 (197) | † K - K - 153–157 - K - K |
| XMP.335 (198) | P - K - 153–157 - K - K |
| XMP.336 (199) | R - R - 153–157 - R - R |
| XMP.337 (200) | H - H - 153–157 - H - H |
| XMP.343 (201) | K - K - 153–157 - K - K, V @ 153 (W) |
| XMP.344 (202) | K - K - 153–157 - K - K, A @ 154 (L) |
| XMP.345 (203) | K - K - 153–157 - K - K, A @ 157 (L) |
| XMP.348 (204) | K - K - K - 153–157 - K - K |
| XMP.349 (205) | K - K - 153–157 - K - K - K |
| XMP.350 (206) | K - K - K - 153–157 - K - K - K |
| XMP.351 (207) | K - K - 153–158 - K - K |
| XMP.352 (208) | K - K - 153–161 |
| XMP.353 (209) | P - 153–161* |
| XMP.354 (210) | † P - 153–161* |
| XMP.355 (211) | P - 153–161 |
| XMP.356 (212) | † P - 153–161 |
| XMP.357 (213) | K - 153–160 - P |
| XMP.358 (214) | K - K - 153–160 - P |
| XMP.373 (215) | † 152–161, K @ 152 (G) |
| XMP.377 (216) | K - K - K - W - A - I - Q - L - K - K |
| XMP.378 (217) | P - W - A - I - Q - L - K - K |
| XMP.379 (218) | K - K - P - W - A - I - Q - L - K - K |
| XMP.380 (219) | K - K - Q - L - L - L - L - K - K |
| XMP.381 (220) | K - K - L - Q - L - L - L - K - K |
| XMP.382 (221) | K - K - L - L - Q - L - L - K - K |
| XMP.383 (222) | K - K - L - L - L - Q - L - K - K |
| XMP.384 (223) | K - K - L - L - L - L - Q - K - K |
| XMP.385 (224) | K - K - L - L - L - L - L - K - K |
| XMP.386 (225) | 152–161, K @ 152 (G), A @ 154 (L) |
| XMP.387 (226) | 152–161, P @ 152 (G), A @ 154 (L) |
| XMP.388 (227) | 152–161 |
| XMP.389 (228) | 151–161, K @ 151 (V) |
| XMP.390 (229) | 151–161, K @ 151 (V), P @ 152 (G) |
| XMP.391 (230) | 150–161 |
| XMP.392 (231) | 150–161, P @ 152 (G) |
| XMP.393 (232) | 148–161, P @ 152 (G) |

TABLE 4-continued

| Peptide (SEQ ID NO:) | Peptide Amino Acid Segment |
| --- | --- |
| XMP.399 (233) | 148–161, F @ 156 (Q), W @ 158 (F) |
| XMP.406 (234) | 147–161, P @ 147 (S), A @ 153 (W) |
| XMP.407 (235) | 147–162, P @ 147 (S), A @ 153 (W), D @ 162 (I) |
| XMP.409 (236) | S - K - 153–157 - K - K, A @ 154 (L) |
| XMP.412 (237) | L - K - K - K - W - A - I - Q |
| XMP.413 (238) | 90–96, 98–99, 90–99, A @ both 94 (Q) & 95 (K) |
| XMP.418 (239) | 148–150, 152–161, P @ 152 (G) |

EXAMPLE 6

Additional Biological Activity Assays of Recombinant Peptides

To assess the endotoxin binding and neutralizing activity of the recombinantly produced peptides, additional experiments are conducted using assays, including a RAW cell-based assay as described in co-owned and copending U.S. patent application Ser. No. 08/372,105 and WO95/19179 (PCT/US95/00498), incorporated by reference in its entirety (see, e.g., Example 7).

To assess the heparin binding and neutralizing activity of the recombinantly produced peptides, additional experiments are performed using assays, including a TCT clotting in co-owned assay, as described U.S. Pat. No. 5,348,942 and in co-owned and copending U.S. patent application Ser. No. 08/306,473 and WO95/19372 (PCT/US94/10427), incorporated by reference in their entirety.

It should be understood that the foregoing disclosure emphasizes certain specific embodiments of the invention and all modifications or alternatives equivalent thereto are within the spirit and scope of the invention as set forth in the appended claims. In particular, numerous modifications and variations in the practice of the invention are expected to occur to those skilled in the art upon consideration of the foregoing description on the presently preferred embodiments thereof. Consequently the only limitations which should be placed upon the scope of the present invention are those that appear in the appended claims.

What is claimed is:

1. A recombinant DNA vector construct suitable for introduction into a bacterial host comprising a coding sequence for a fusion protein having: (a) at least one cationic bactericidal/permeability-increasing (BPI) peptide encoding DNA sequence; (b) a carrier protein encoding DNA sequence; and (c) an amino acid cleavage site encoding DNA sequence located between the sequences (a) and (b), wherein the construct additionally encodes a bacterial secretory leader sequence at the amino-terminus of the fusion protein and wherein the encoded BPI peptide has anti-bacterial activity.

2. The vector construct of claim 1, wherein the coding sequence for the fusion protein is 5'-(b)-(c)-(a)-3'.

3. The vector construct of claim 1, wherein the anti-bacterial encoded BPI peptide also has anti-fungal activity.

4. The vector construct of claim 1, wherein the anti-bacterial encoded BPI peptide also has endotoxin-binding activity.

5. The vector construct of claim 1, wherein the anti-bacterial encoded BPI peptide also has heparin-binding activity.

6. The vector construct of claim 1, wherein the encoded carrier protein is a cationic carrier protein.

7. The vector construct of claim 1, wherein cationic carrier protein is selected from the group of gelonin and the D subunit of human osteogenic protein.

8. The vector construct of claim 1, wherein the encoded BPI peptide has an amino acid sequence given in any one of the sequences SEQ ID NOS. 1–239.

9. The vector construct of claim 1, wherein the encoded amino acid cleavage site is selected from the group of codons encoding Asp-Pro, Met, Trp and Glu.

10. A bacterial host cell transformed with the vector construct of claim 1.

11. An E. coli host cell according to claim 10.

12. A method for bacterial production of a cationic BPI peptide comprising the steps of:

(a) culturing a transformed bacterial host cell according to claim 10 under conditions allowing expression therein of the fusion protein;

(b) isolating the expressed fusion protein;

(c) cleaving the expressed fusion protein to release the cationic BPI peptide; and (d) isolating the cationic BPI peptide.

13. A method for bacterial production of a cationic BPI peptide comprising the steps of:

(a) culturing a transformed bacterial host cell according to claim 10 under conditions allowing expression therein of the fusion protein;

(b) cleaving the expressed fusion protein to release the cationic BPI peptide; and (c) isolating the cationic BPI peptide.

14. A method for bacterial production of a fusion protein comprising the steps of:

(a) culturing a transformed bacterial host cell according to claim 10 under conditions allowing expression therein of the fusion protein; and (b) isolating the expressed fusion protein.

15. The fusion protein product of the process of claim 14.

* * * * *

SEQUENCE LISTING ( 1 ) GENERAL INFORMATION:

( i i i ) NUMBER OF SEQUENCES: 265

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.1"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:1:

Gln Gln Gly Thr Ala Ala Leu Gln Lys Glu Leu Lys Arg Ile Lys
     1                 5                      10                15

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.2"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:2:

```
Ile  Lys  Ile  Ser  Gly  Lys  Trp  Lys  Ala  Gln  Lys  Arg  Phe  Leu  Lys
 1              5                        10                          15
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.3"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:3:

```
Asn  Val  Gly  Leu  Lys  Phe  Ser  Ile  Ser  Asn  Ala  Asn  Ile  Lys  Ile  Ser
 1              5                        10                          15
Gly  Lys  Trp  Lys  Ala  Gln  Lys  Arg  Phe  Leu  Lys
           20                        25
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.4"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:4:

```
Leu  Gln  Lys  Glu  Leu  Lys  Arg  Ile  Lys  Ile  Pro  Asp  Tyr  Ser  Asp  Ser
 1              5                        10                          15
Phe  Lys  Ile  Lys  His  Leu
                20
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( D ) TOPOLOGY: linear (i i) MOLECULE TYPE: peptide (i x) FEATURE:
    (A) NAME/KEY: misc_feature
    (D) OTHER INFORMATION: "XMP.5"

(i x) FEATURE:
    (A) NAME/KEY: Modified-site
    (B) LOCATION: C-Terminus
    (D) OTHER INFORMATION: /label=Amidation
        / note= "The C-Terminus is Amidated."

(x i) SEQUENCE DESCRIPTION: SEQ ID NO:5:

```
Val His Val His Ile Ser Lys Ser Lys Val Gly Trp Leu Ile Gln Leu
 1               5                  10                  15
Phe His Lys Lys Ile Glu
                 20
```

(2) INFORMATION FOR SEQ ID NO:6:

(i) SEQUENCE CHARACTERISTICS:
        (A) LENGTH: 17 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.6"

(i x) FEATURE:
        (A) NAME/KEY: Modified-site
        (B) LOCATION: C-Terminus
        (D) OTHER INFORMATION: /label=Amidation
            / note= "The C-Terminus is Amidated."

(x i) SEQUENCE DESCRIPTION: SEQ ID NO:6:

```
Ser Ile Ser Ala Asp Leu Lys Leu Gly Ser Asn Pro Thr Ser Gly Lys
 1               5                  10                  15
Pro
```

(2) INFORMATION FOR SEQ ID NO:7:

(i) SEQUENCE CHARACTERISTICS:
        (A) LENGTH: 20 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.7"

(i x) FEATURE:
        (A) NAME/KEY: Modified-site
        (B) LOCATION: C-Terminus
        (D) OTHER INFORMATION: /label=Amidation
            / note= "The C-Terminus is Amidated."

(x i) SEQUENCE DESCRIPTION: SEQ ID NO:7:

```
Lys Trp Lys Ala Gln Lys Arg Phe Leu Lys Lys Trp Lys Ala Gln Lys
 1               5                  10                  15
Arg Phe Leu Lys
             20
```

(2) INFORMATION FOR SEQ ID NO:8:

(i) SEQUENCE CHARACTERISTICS:
        (A) LENGTH: 10 amino acids (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "XMP.8"

(ix) FEATURE:
              (A) NAME/KEY: Modified-site
              (B) LOCATION: C-Terminus
              (D) OTHER INFORMATION: /label=Amidation
                      / note= "The C-Terminus is Amidated."

(xi) SEQUENCE DESCRIPTION: SEQ ID NO:8:

Lys  Trp  Lys  Ala  Gln  Lys  Arg  Phe  Leu  Lys
       1                  5                        10

(2) INFORMATION FOR SEQ ID NO:9:

(i) SEQUENCE CHARACTERISTICS:
              (A) LENGTH: 15 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "XMP.9"

(ix) FEATURE:
              (A) NAME/KEY: Modified-site
              (B) LOCATION: C-Terminus
              (D) OTHER INFORMATION: /label=Amidation
                      / note= "The C-Terminus is Amidated."

(xi) SEQUENCE DESCRIPTION: SEQ ID NO:9:

Lys  Arg  Phe  Leu  Lys  Lys  Trp  Lys  Ala  Gln  Lys  Arg  Phe  Leu  Lys
       1                  5                        10                       15

(2) INFORMATION FOR SEQ ID NO:10:

(i) SEQUENCE CHARACTERISTICS:
              (A) LENGTH: 25 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "XMP.10a"

(ix) FEATURE:
              (A) NAME/KEY: Modified-site
              (B) LOCATION: C-Terminus
              (D) OTHER INFORMATION: /label=Amidation
                      / note= "The C-Terminus is Amidated."

(xi) SEQUENCE DESCRIPTION: SEQ ID NO:10:

Lys  Arg  Phe  Leu  Lys  Lys  Trp  Lys  Ala  Gln  Lys  Arg  Phe  Leu  Lys  Lys
       1                  5                        10                       15

Trp  Lys  Ala  Gln  Lys  Arg  Phe  Leu  Lys
                       20                       25

(2) INFORMATION FOR SEQ ID NO:11:

(i) SEQUENCE CHARACTERISTICS:
              (A) LENGTH: 26 amino acids
              (B) TYPE: amino acid
              (D) TOPOLOGY: linear (i i) MOLECULE TYPE: peptide (i x) FEATURE:
 (A) NAME/KEY: misc_feature
 (D) OTHER INFORMATION: "XMP.10b"

(i x) FEATURE:
 (A) NAME/KEY: Modified-site
 (B) LOCATION: C-Terminus
 (D) OTHER INFORMATION: /label=Amidation
  / note= "The C-Terminus is Amidated."

(x i) SEQUENCE DESCRIPTION: SEQ ID NO:11:

```
Gln Lys Arg Phe Leu Lys Lys Trp Lys Ala Gln Lys Arg Phe Leu Lys
 1               5                  10                      15
Lys Trp Lys Ala Gln Lys Arg Phe Leu Lys
             20                  25
```

(2) INFORMATION FOR SEQ ID NO:12:

(i) SEQUENCE CHARACTERISTICS:
  (A) LENGTH: 13 amino acids
  (B) TYPE: amino acid
  (D) TOPOLOGY: linear (i i) MOLECULE TYPE: peptide (i x) FEATURE:
  (A) NAME/KEY: misc_feature
  (D) OTHER INFORMATION: "XMP.11"

(i x) FEATURE:
  (A) NAME/KEY: Modified-site
  (B) LOCATION: C-Terminus
  (D) OTHER INFORMATION: /label=Amidation
   / note= "The C-Terminus is Amidated."

(x i) SEQUENCE DESCRIPTION: SEQ ID NO:12:

```
Lys Ser Lys Val Trp Leu Ile Gln Leu Phe His Lys Lys
 1               5                  10
```

(2) INFORMATION FOR SEQ ID NO:13:

(i) SEQUENCE CHARACTERISTICS:
  (A) LENGTH: 29 amino acids
  (B) TYPE: amino acid
  (D) TOPOLOGY: linear (i i) MOLECULE TYPE: peptide (i x) FEATURE:
  (A) NAME/KEY: misc_feature
  (D) OTHER INFORMATION: "XMP.12"

(i x) FEATURE:
  (A) NAME/KEY: Modified-site
  (B) LOCATION: C-Terminus
  (D) OTHER INFORMATION: /label=Amidation
   / note= "The C-Terminus is Amidated."

(x i) SEQUENCE DESCRIPTION: SEQ ID NO:13:

```
Ser Val His Val His Ile Ser Lys Ser Lys Val Gly Trp Leu Ile Gln
 1               5                  10                      15
Leu Phe His Lys Lys Ile Glu Ser Ala Leu Arg Asn Lys
             20                  25
```

(2) INFORMATION FOR SEQ ID NO:14:

(i) SEQUENCE CHARACTERISTICS:
  (A) LENGTH: 14 amino acids
  (B) TYPE: amino acid (D) TOPOLOGY: linear (i i) MOLECULE TYPE: peptide (i x) FEATURE:
    (A) NAME/KEY: misc_feature
    (D) OTHER INFORMATION: "XMP.13"

(i x) FEATURE:
    (A) NAME/KEY: Modified-site
    (B) LOCATION: C-Terminus
    (D) OTHER INFORMATION: /label=Amidation
    / note= "The C-Terminus is Amidated."

(x i) SEQUENCE DESCRIPTION: SEQ ID NO:14:

Lys Ser Lys Val Gly Trp Leu Ile Gln Leu Phe His Lys Lys
 1           5                    10

(2) INFORMATION FOR SEQ ID NO:15:

(i) SEQUENCE CHARACTERISTICS:
    (A) LENGTH: 30 amino acids
    (B) TYPE: amino acid
    (D) TOPOLOGY: linear (i i) MOLECULE TYPE: peptide (i x) FEATURE:
    (A) NAME/KEY: misc_feature
    (D) OTHER INFORMATION: "XMP.14"

(i x) FEATURE:
    (A) NAME/KEY: Modified-site
    (B) LOCATION: C-Terminus
    (D) OTHER INFORMATION: /label=Amidation
    / note= "The C-Terminus is Amidated."

(x i) SEQUENCE DESCRIPTION: SEQ ID NO:15:

Gly Thr Ala Ala Leu Gln Lys Glu Leu Lys Arg Ile Lys Ile Pro Asp
 1           5                    10                        15
Tyr Ser Asp Ser Phe Lys Ile Lys His Leu Gly Lys Gly His
         20                  25                  30

(2) INFORMATION FOR SEQ ID NO:16:

(i) SEQUENCE CHARACTERISTICS:
    (A) LENGTH: 15 amino acids
    (B) TYPE: amino acid
    (D) TOPOLOGY: linear (i i) MOLECULE TYPE: peptide (i x) FEATURE:
    (A) NAME/KEY: misc_feature
    (D) OTHER INFORMATION: "XMP.15"

(i x) FEATURE:
    (A) NAME/KEY: Modified-site
    (B) LOCATION: C-Terminus
    (D) OTHER INFORMATION: /label=Amidation
    / note= "The C-Terminus is Amidated."

(x i) SEQUENCE DESCRIPTION: SEQ ID NO:16:

Ala Lys Ile Ser Gly Lys Trp Lys Ala Gln Lys Arg Phe Leu Lys
 1           5                    10                     15

(2) INFORMATION FOR SEQ ID NO:17:

(i) SEQUENCE CHARACTERISTICS:
    (A) LENGTH: 15 amino acids
    (B) TYPE: amino acid
    (D) TOPOLOGY: linear ( i i ) MOLECULE TYPE: peptide ( i x ) FEATURE:
    ( A ) NAME/KEY: misc_feature
    ( D ) OTHER INFORMATION: "XMP.16"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:17:

Ile Ala Ile Ser Gly Lys Trp Lys Ala Gln Lys Arg Phe Leu Lys
1               5                   10                  15

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.17"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:18:

Ile Lys Ala Ser Gly Lys Trp Lys Ala Gln Lys Arg Phe Leu Lys
1               5                   10                  15

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.18"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:19:

Ile Lys Ile Ala Gly Lys Trp Lys Ala Gln Lys Arg Phe Leu Lys
1               5                   10                  15

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.19"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:20:

Ile Lys Ile Ser Ala Lys Trp Lys Ala Gln Lys Arg Phe Leu Lys
1               5                   1 0                 1 5

( 2 ) INFORMATION FOR SEQ ID NO:21:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.20"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:21:

Ile Lys Ile Ser Gly Ala Trp Lys Ala Gln Lys Arg Phe Leu Lys
1               5                   1 0                 1 5

( 2 ) INFORMATION FOR SEQ ID NO:22:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.21"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:22:

Ile Lys Ile Ser Gly Lys Ala Lys Ala Gln Lys Arg Phe Leu Lys
1               5                   1 0                 1 5

( 2 ) INFORMATION FOR SEQ ID NO:23:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.22"

( i x ) FEATURE:
    ( A ) NAME/KEY: Modified-site
    ( B ) LOCATION: C-Terminus
    ( D ) OTHER INFORMATION: /label=Amidation / note= "The C-Terminus is Amidated."

( x i ) SEQUENCE DESCRIPTION: SEQ ID NO:23:

```
Ile  Lys  Ile  Ser  Gly  Lys  Trp  Ala  Ala  Gln  Lys  Arg  Phe  Leu  Lys
 1              5                        10                         15
```

( 2 ) INFORMATION FOR SEQ ID NO:24:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.23"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:24:

```
Ile  Lys  Ile  Ser  Gly  Lys  Trp  Lys  Ala  Ala  Lys  Arg  Phe  Leu  Lys
 1              5                        10                         15
```

( 2 ) INFORMATION FOR SEQ ID NO:25:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.24"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:25:

```
Ile  Lys  Ile  Ser  Gly  Lys  Trp  Lys  Ala  Gln  Ala  Arg  Phe  Leu  Lys
 1              5                        10                         15
```

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.25"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:26:

```
Ile  Lys  Ile  Ser  Gly  Lys  Trp  Lys  Ala  Gln  Lys  Ala  Phe  Leu  Lys
```

```
              1               5              1 0             1 5
```

( 2 ) INFORMATION FOR SEQ ID NO:27:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.26"

( i x ) FEATURE:
    ( A ) NAME/KEY: Modified-site
    ( B ) LOCATION: C-Terminus
    ( D ) OTHER INFORMATION: /label=Amidation
      / note= "The C-Terminus is Amidated."

( x i ) SEQUENCE DESCRIPTION: SEQ ID NO:27:

```
Ile  Lys  Ile  Ser  Gly  Lys  Trp  Lys  Ala  Gln  Lys  Arg  Ala  Leu  Lys
 1              5                        1 0                       1 5
```

( 2 ) INFORMATION FOR SEQ ID NO:28:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.27"

( i x ) FEATURE:
    ( A ) NAME/KEY: Modified-site
    ( B ) LOCATION: C-Terminus
    ( D ) OTHER INFORMATION: /label=Amidation
      / note= "The C-Terminus is Amidated."

( x i ) SEQUENCE DESCRIPTION: SEQ ID NO:28:

```
Ile  Lys  Ile  Ser  Gly  Lys  Trp  Lys  Ala  Gln  Lys  Arg  Phe  Ala  Lys
 1              5                        1 0                       1 5
```

( 2 ) INFORMATION FOR SEQ ID NO:29:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.28"

( i x ) FEATURE:
    ( A ) NAME/KEY: Modified-site
    ( B ) LOCATION: C-Terminus
    ( D ) OTHER INFORMATION: /label=Amidation
      / note= "The C-Terminus is Amidated."

( x i ) SEQUENCE DESCRIPTION: SEQ ID NO:29:

```
Ile  Lys  Ile  Ser  Gly  Lys  Trp  Lys  Ala  Gln  Lys  Arg  Phe  Leu  Ala
 1              5                        1 0                       1 5
```

( 2 ) INFORMATION FOR SEQ ID NO:30:

( i ) SEQUENCE CHARACTERISTICS:
( A ) LENGTH: 28 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.29"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:30:

Lys Ser Lys Val Gly Trp Leu Ile Gln Leu Phe His Lys Lys Lys Ser
1               5                   10                  15
Lys Val Gly Trp Leu Ile Gln Leu Phe His Lys Lys
            20                  25

( 2 ) INFORMATION FOR SEQ ID NO:31:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.30"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:31:

Lys Trp Lys Ala Gln Lys Arg Phe Leu Lys Lys Ser Lys Val Gly Trp
1               5                   10                  15
Leu Ile Gln Leu Phe His Lys Lys
            20

( 2 ) INFORMATION FOR SEQ ID NO:32:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.31"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:32:

Ala Ser Lys Val Gly Trp Leu Ile Gln Leu Phe His Lys Lys
1               5                   10

( 2 ) INFORMATION FOR SEQ ID NO:33:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.32"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:33:

Lys Ala Lys Val Gly Trp Leu Ile Gln Leu Phe His Lys Lys
 1             5                  10

( 2 ) INFORMATION FOR SEQ ID NO:34:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.33"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:34:

Lys Ser Ala Val Gly Trp Leu Ile Gln Leu Phe His Lys Lys
 1             5                  10

( 2 ) INFORMATION FOR SEQ ID NO:35:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.34"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:35:

Lys Ser Lys Ala Gly Trp Leu Ile Gln Leu Phe His Lys Lys
 1             5                  10

( 2 ) INFORMATION FOR SEQ ID NO:36:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.35"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:36:

```
Lys  Ser  Lys  Val  Ala  Trp  Leu  Ile  Gln  Leu  Phe  His  Lys  Lys
 1                   5                        10
```

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.36"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:37:

```
Lys  Ser  Lys  Val  Gly  Ala  Leu  Ile  Gln  Leu  Phe  His  Lys  Lys
 1                   5                        10
```

( 2 ) INFORMATION FOR SEQ ID NO:38:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.37"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:38:

```
Lys  Ser  Lys  Val  Gly  Trp  Ala  Ile  Gln  Leu  Phe  His  Lys  Lys
 1                   5                        10
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature ( D ) OTHER INFORMATION: "XMP.38"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:39:

Lys Ser Lys Val Gly Trp Leu Ala Gln Leu Phe His Lys Lys
1             5                    10

( 2 ) INFORMATION FOR SEQ ID NO:40:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.39"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:40:

Lys Ser Lys Val Gly Trp Leu Ile Ala Leu Phe His Lys Lys
1             5                    10

( 2 ) INFORMATION FOR SEQ ID NO:41:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.40"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:41:

Lys Ser Lys Val Gly Trp Leu Ile Gln Ala Phe His Lys Lys
1             5                    10

( 2 ) INFORMATION FOR SEQ ID NO:42:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.41"

( i x ) FEATURE:
        ( A ) NAME/KEY: Modified-site
        ( B ) LOCATION: C-Terminus (D) OTHER INFORMATION: /label=Amidation
/ note= "The C-Terminus is Amidated."

(x i) SEQUENCE DESCRIPTION: SEQ ID NO:42:

Lys Ser Lys Val Gly Trp Leu Ile Gln Leu Ala His Lys Lys
1               5                   10

(2) INFORMATION FOR SEQ ID NO:43:

(i) SEQUENCE CHARACTERISTICS:
(A) LENGTH: 14 amino acids
(B) TYPE: amino acid
(D) TOPOLOGY: linear (i i) MOLECULE TYPE: peptide (i x) FEATURE:
(A) NAME/KEY: misc_feature
(D) OTHER INFORMATION: "XMP.42"

(i x) FEATURE:
(A) NAME/KEY: Modified-site
(B) LOCATION: C-Terminus
(D) OTHER INFORMATION: /label=Amidation
/ note= "The C-Terminus is Amidated."

(x i) SEQUENCE DESCRIPTION: SEQ ID NO:43:

Lys Ser Lys Val Gly Trp Leu Ile Gln Leu Phe Ala Lys Lys
1               5                   10

(2) INFORMATION FOR SEQ ID NO:44:

(i) SEQUENCE CHARACTERISTICS:
(A) LENGTH: 14 amino acids
(B) TYPE: amino acid
(D) TOPOLOGY: linear (i i) MOLECULE TYPE: peptide (i x) FEATURE:
(A) NAME/KEY: misc_feature
(D) OTHER INFORMATION: "XMP.43"

(i x) FEATURE:
(A) NAME/KEY: Modified-site
(B) LOCATION: C-Terminus
(D) OTHER INFORMATION: /label=Amidation
/ note= "The C-Terminus is Amidated."

(x i) SEQUENCE DESCRIPTION: SEQ ID NO:44:

Lys Ser Lys Val Gly Trp Leu Ile Gln Leu Phe His Ala Lys
1               5                   10

(2) INFORMATION FOR SEQ ID NO:45:

(i) SEQUENCE CHARACTERISTICS:
(A) LENGTH: 14 amino acids
(B) TYPE: amino acid
(D) TOPOLOGY: linear (i i) MOLECULE TYPE: peptide (i x) FEATURE:
(A) NAME/KEY: misc_feature
(D) OTHER INFORMATION: "XMP.44"

(i x) FEATURE:
(A) NAME/KEY: Modified-site
(B) LOCATION: C-Terminus
(D) OTHER INFORMATION: /label=Amidation
/ note= "The C-Terminus is Amidated."

(x i) SEQUENCE DESCRIPTION: SEQ ID NO:45:

```
Lys  Ser  Lys  Val  Gly  Trp  Leu  Ile  Gln  Leu  Phe  His  Lys  Ala
 1              5                   10
```

( 2 ) INFORMATION FOR SEQ ID NO:46:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.45"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:46:

```
Ile  Lys  Ile  Ser  Gly  Lys  Trp  Lys  Ala  Ala  Ala  Arg  Phe  Leu  Lys
 1              5                   10                            15
```

( 2 ) INFORMATION FOR SEQ ID NO:47:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.46"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:47:

```
Lys  Trp  Lys  Ala  Ala  Ala  Arg  Phe  Leu  Lys  Lys  Trp  Lys  Ala  Gln  Lys
 1              5                   10                            15
Arg  Phe  Leu  Lys
              20
```

( 2 ) INFORMATION FOR SEQ ID NO:48:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.47"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:48:

```
Lys  Trp  Lys  Ala  Gln  Lys  Arg  Phe  Leu  Lys  Lys  Trp  Lys  Ala  Ala  Ala
 1              5                   10                            15
```

Arg Phe Leu Lys
                                    20

(2) INFORMATION FOR SEQ ID NO:49:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.48"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:49:

Lys Trp Lys Ala Ala Ala Arg Phe Leu Lys Lys Trp Lys Ala Ala Ala
 1             5                10                    15

Arg Phe Leu Lys
                    20

(2) INFORMATION FOR SEQ ID NO:50:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.49"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:50:

Val Thr Asn Ser Val Ser Ser Lys Leu Gln Pro Tyr Phe Gln
 1             5                10

(2) INFORMATION FOR SEQ ID NO:51:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.50"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:51:

Val Thr Asn Ser Val Ser Ser Lys Leu Gln Pro Tyr Phe Gln Thr ( 2 ) INFORMATION FOR SEQ ID NO:52:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.51"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:52:

Val Thr Asn Ser Val Ser Ser Lys Leu Gln Pro Tyr Phe Gln Thr Leu
 1                5                   10                15

( 2 ) INFORMATION FOR SEQ ID NO:53:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.52"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:53:

Val Thr Asn Ser Val Ser Ser Lys Leu Gln Pro Tyr Phe Gln Thr Leu
 1                5                   10                15

Pro ( 2 ) INFORMATION FOR SEQ ID NO:54:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.53"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:54:

Val Thr Asn Ser Val Ser Ser Lys Leu Gln Pro Tyr Phe Gln Thr Leu
 1                5                   10                15

Pro Val ( 2 ) INFORMATION FOR SEQ ID NO:55:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.54"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:55:

Gly Thr Ala Ala Leu Gln Lys Glu Leu Lys Arg Ile Lys Ile Pro
 1              5                 10              15

( 2 ) INFORMATION FOR SEQ ID NO:56:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.55"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:56:

Gly Trp Leu Ile Gln Leu Phe His Lys Lys Ile Glu Ser Ala Leu Arg
 1              5                 10              15

Asn Lys Met Asn Ser
           20

( 2 ) INFORMATION FOR SEQ ID NO:57:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.56"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:57:

Ile Lys Ile Ser Gly Lys Trp Lys Ala Lys Gln Arg Phe Leu Lys
 1              5                 10              15

( 2 ) INFORMATION FOR SEQ ID NO:58:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.57 reduced"

( i x ) FEATURE:
        ( A ) NAME/KEY: Modified-site
        ( B ) LOCATION: C-Terminus
        ( D ) OTHER INFORMATION: /label=Amidation
                / note= "The C-Terminus is Amidated."

( x i ) SEQUENCE DESCRIPTION: SEQ ID NO:58:

Cys Ile Lys Ile Ser Gly Lys Trp Lys Ala Gln Lys Arg Pro Leu Cys
 1              5                     10                 15

( 2 ) INFORMATION FOR SEQ ID NO:59:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.58 reduced"

( i x ) FEATURE:
        ( A ) NAME/KEY: Modified-site
        ( B ) LOCATION: C-Terminus
        ( D ) OTHER INFORMATION: /label=Amidation
                / note= "The C-Terminus is Amidated."

( x i ) SEQUENCE DESCRIPTION: SEQ ID NO:59:

Cys Ile Lys Ile Ser Gly Lys Trp Lys Ala Gln Lys Arg Phe Leu Lys
 1              5                     10                 15

( 2 ) INFORMATION FOR SEQ ID NO:60:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.59"

( i x ) FEATURE:
        ( A ) NAME/KEY: Modified-site
        ( B ) LOCATION: C-Terminus
        ( D ) OTHER INFORMATION: /label=Amidation
                / note= "The C-Terminus is Amidated."

( x i ) SEQUENCE DESCRIPTION: SEQ ID NO:60:

Ile Lys Ile Ser Gly Ala Trp Ala Ala Gln Lys Arg Phe Leu Lys
 1              5                    10                15

( 2 ) INFORMATION FOR SEQ ID NO:61:

( i ) SEQUENCE CHARACTERISTICS:
        ( A ) LENGTH: 15 amino acids
        ( B ) TYPE: amino acid ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.60"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:61:

Ile Ala Ile Ser Gly Lys Trp Lys Ala Gln Lys Arg Phe Leu Ala
1           5               10                  15

( 2 ) INFORMATION FOR SEQ ID NO:62:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.61"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:62:

Ile Lys Ile Ser Gly Lys Phe Lys Ala Gln Lys Arg Phe Leu Lys
1           5               10                  15

( 2 ) INFORMATION FOR SEQ ID NO:63:

( i ) SEQUENCE CHARACTERISTICS:
  ( A ) LENGTH: 30 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.62 reduced"

( x i ) SEQUENCE DESCRIPTION: SEQ ID NO:63:

Leu Gly Ser Asn Pro Thr Ser Gly Lys Pro Thr Ile Thr Cys Ser Ser
1               5                   10                  15

Cys Ser Ser His Ile Asn Ser Val His Val His Ile Ser Lys
            20              25                  30

( 2 ) INFORMATION FOR SEQ ID NO:64:

( i ) SEQUENCE CHARACTERISTICS:
  ( A ) LENGTH: 29 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.63"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:64:

Ile Lys Ile Ser Gly Lys Trp Lys Ala Gln Lys Arg Phe Leu Lys Lys
 1               5                  10                      15

Ser Lys Val Gly Trp Leu Ile Gln Leu Phe His Lys Lys
              20                  25

( 2 ) INFORMATION FOR SEQ ID NO:65:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.64"

( x i ) SEQUENCE DESCRIPTION: SEQ ID NO:65:

Val Thr Asn Ser Val Ser Ser Lys Leu Gln Pro Tyr Phe Gln Thr Leu
 1               5                  10                      15

( 2 ) INFORMATION FOR SEQ ID NO:66:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.65 reduced"

( i x ) FEATURE:
    ( A ) NAME/KEY: Modified-site
    ( B ) LOCATION: C-Terminus
    ( D ) OTHER INFORMATION: /label=Amidation
      / note= "The C-Terminus is Amidated."

( i x ) FEATURE:
    ( A ) NAME/KEY: Disulfide-bond
    ( B ) LOCATION: 1..17

( x i ) SEQUENCE DESCRIPTION: SEQ ID NO:66:

Cys Ile Lys Ile Ser Gly Lys Trp Lys Ala Gln Lys Arg Phe Leu Lys
 1               5                  10                      15

Cys ( 2 ) INFORMATION FOR SEQ ID NO:67:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.68 reduced"

( x i ) SEQUENCE DESCRIPTION: SEQ ID NO:67:

```
Leu  Gly  Ser  Asn  Pro  Thr  Ser  Gly  Lys  Pro  Thr  Ile  Thr  Ala  Ser  Ser
 1              5                        10                        15

Cys  Ser  Ser  His  Ile  Asn  Ser  Val  His  Val  His  Ile  Ser  Lys
                20                       25                       30
```

(2) INFORMATION FOR SEQ ID NO:68:

(i) SEQUENCE CHARACTERISTICS:
        (A) LENGTH: 30 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.69"

(i x) FEATURE:
        (A) NAME/KEY: Modified-site
        (B) LOCATION: C-Terminus
        (D) OTHER INFORMATION: /label=Amidation
            / note= "The C-Terminus is Amidated."

(x i) SEQUENCE DESCRIPTION: SEQ ID NO:68:

```
Lys  Trp  Lys  Ala  Ala  Ala  Arg  Phe  Leu  Lys  Lys  Trp  Lys  Ala  Ala  Ala
 1              5                        10                        15

Arg  Phe  Leu  Lys  Lys  Trp  Lys  Ala  Ala  Ala  Arg  Phe  Leu  Lys
                20                       25                       30
```

(2) INFORMATION FOR SEQ ID NO:69:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.73"

(i x) FEATURE:
        (A) NAME/KEY: Modified-site
        (B) LOCATION: C-Terminus
        (D) OTHER INFORMATION: /label=Amidation
            / note= "The C-Terminus is Amidated."

(x i) SEQUENCE DESCRIPTION: SEQ ID NO:69:

```
Ile  Lys  Ile  Ser  Gly  Lys  Trp  Lys  Ala  Gln  Phe  Arg  Phe  Leu  Lys
 1              5                        10                       15
```

(2) INFORMATION FOR SEQ ID NO:70:

(i) SEQUENCE CHARACTERISTICS:
        (A) LENGTH: 24 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.74"

(i x) FEATURE:
        (A) NAME/KEY: Modified-site
        (B) LOCATION: C-Terminus
        (D) OTHER INFORMATION: /label=Amidation
            / note= "The C-Terminus is Amidated."

(x i) SEQUENCE DESCRIPTION: SEQ ID NO:70:

```
  Lys  Ser  Lys  Val  Gly  Trp  Leu  Ile  Gln  Leu  Phe  His  Lys  Lys  Trp
   1              5                        10                       15

Lys  Ala  Gln  Lys  Arg  Phe  Leu  Lys
                 20
```

(2) INFORMATION FOR SEQ ID NO:71:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.75"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:71:

```
  Ile  Lys  Lys  Arg  Ala  Ile  Ser  Phe  Leu  Gly  Lys  Lys  Trp  Gln  Lys
   1              5                        10                       15
```

(2) INFORMATION FOR SEQ ID NO:72:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.77"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:72:

```
  Ile  Lys  Ile  Ser  Gly  Lys  Trp  Lys  Ala  Gln  Trp  Arg  Phe  Leu  Lys
   1              5                        10                       15
```

(2) INFORMATION FOR SEQ ID NO:73:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.78"

(xi) SEQUENCE DESCRIPTION: SEQ ID NO:73:

```
  Met  Ser  Gly  Asn  Phe  Asp  Leu  Ser  Ile  Glu  Gly  Met  Ser  Ile  Ser  Ala
   1              5                        10                       15

Asp  Leu  Lys
```

(2) INFORMATION FOR SEQ ID NO:74:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.79"

( i x ) FEATURE:
  ( A ) NAME/KEY: Modified-site
  ( B ) LOCATION: C-Terminus
  ( D ) OTHER INFORMATION: /label=Amidation
      / note= "The C-Terminus is Amidated."

( x i ) SEQUENCE DESCRIPTION: SEQ ID NO:74:

Ile Lys Ile Ser Gly Lys Trp Lys Ala Lys Lys Arg Phe Leu Lys
 1               5                  10                  15

( 2 ) INFORMATION FOR SEQ ID NO:75:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.81"

( i x ) FEATURE:
  ( A ) NAME/KEY: Modified-site
  ( B ) LOCATION: C-Terminus
  ( D ) OTHER INFORMATION: /label=Amidation
      / note= "The C-Terminus is Amidated."

( x i ) SEQUENCE DESCRIPTION: SEQ ID NO:75:

Ile Lys Ile Ser Gly Lys Trp Lys Ala Phe Lys Arg Phe Leu Lys
 1               5                  10                  15

( 2 ) INFORMATION FOR SEQ ID NO:76:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.82"

( i x ) FEATURE:
  ( A ) NAME/KEY: Modified-site
  ( B ) LOCATION: C-Terminus
  ( D ) OTHER INFORMATION: /label=Amidation
      / note= "The C-Terminus is Amidated."

( x i ) SEQUENCE DESCRIPTION: SEQ ID NO:76:

Lys Ser Lys Val Gly Trp Leu Ile Gln Leu Trp His Lys Lys
 1               5                  10

( 2 ) INFORMATION FOR SEQ ID NO:77:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.85"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:77:

```
Lys  Ser  Lys  Val  Leu  Trp  Leu  Ile  Gln  Leu  Phe  His  Lys  Lys
 1              5                        10
```

( 2 ) INFORMATION FOR SEQ ID NO:78:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.86"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:78:

```
Lys  Ser  Lys  Val  Gly  Trp  Leu  Ile  Leu  Leu  Phe  His  Lys  Lys
 1              5                        10
```

( 2 ) INFORMATION FOR SEQ ID NO:79:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.87"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:79:

```
Lys  Ser  Lys  Val  Gly  Trp  Leu  Ile  Gln  Leu  Phe  Leu  Lys  Lys
 1              5                        10
```

( 2 ) INFORMATION FOR SEQ ID NO:80:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature (D) OTHER INFORMATION: "XMP.88"

(ix) FEATURE:
    (A) NAME/KEY: Modified-site
    (B) LOCATION: C-Terminus
    (D) OTHER INFORMATION: /label=Amidation
        / note= "The C-Terminus is Amidated."

(xi) SEQUENCE DESCRIPTION: SEQ ID NO:80:

| Ile | Lys | Ile | Ser | Gly | Lys | Trp | Lys | Ala | Phe | Phe | Arg | Phe | Leu | Lys |
|---|---|---|---|---|---|---|---|---|---|---|---|---|---|---|
| 1 | | | | 5 | | | | | 10 | | | | | 15 |

(2) INFORMATION FOR SEQ ID NO:81:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.91"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:81:

| Lys | Ser | Lys | Val | Gly | Trp | Leu | Ile | Phe | Leu | Phe | His | Lys | Lys |
|---|---|---|---|---|---|---|---|---|---|---|---|---|---|
| 1 | | | | 5 | | | | | 10 | | | | |

(2) INFORMATION FOR SEQ ID NO:82:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.92"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:82:

| Lys | Ser | Lys | Val | Gly | Trp | Leu | Ile | Lys | Leu | Phe | His | Lys | Lys |
|---|---|---|---|---|---|---|---|---|---|---|---|---|---|
| 1 | | | | 5 | | | | | 10 | | | | |

(2) INFORMATION FOR SEQ ID NO:83:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.94"

(ix) FEATURE:
        (A) NAME/KEY: Modified-site
        (B) LOCATION: C-Terminus (D) OTHER INFORMATION: /label=Amidation
            / note= "The C-Terminus is Amidated."

(xi) SEQUENCE DESCRIPTION: SEQ ID NO:83:

Lys  Ser  Lys  Val  Gly  Trp  Leu  Ile  Gln  Leu  Phe  Phe  Lys  Lys
 1               5                    10

(2) INFORMATION FOR SEQ ID NO:84:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.95"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:84:

Lys  Ser  Lys  Val  Phe  Trp  Leu  Ile  Gln  Leu  Phe  His  Lys  Lys
 1               5                    10

(2) INFORMATION FOR SEQ ID NO:85:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.96"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:85:

Lys  Ser  Lys  Val  Gly  Trp  Leu  Ile  Gln  Leu  Phe  His  Lys  Phe
 1               5                    10

(2) INFORMATION FOR SEQ ID NO:86:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.97"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:86:

```
Lys  Ser  Lys  Val  Lys  Trp  Leu  Ile  Gln  Leu  Phe  His  Lys  Lys
 1              5                   10
```

( 2 ) INFORMATION FOR SEQ ID NO:87:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.99"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:87:

```
Lys  Trp  Lys  Ala  Gln  Trp  Arg  Phe  Leu  Lys  Lys  Trp  Lys  Ala  Gln  Trp
 1              5                   10                            15
Arg  Phe  Leu  Lys  Lys  Trp  Lys  Ala  Gln  Trp  Arg  Phe  Leu  Lys
           20                        25                        30
```

( 2 ) INFORMATION FOR SEQ ID NO:88:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.100"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:88:

```
Lys  Ser  Lys  Val  Lys  Trp  Leu  Ile  Lys  Leu  Phe  His  Lys  Lys
 1              5                   10
```

( 2 ) INFORMATION FOR SEQ ID NO:89:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.101"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:89:

```
Lys  Ser  Lys  Val  Lys  Trp  Leu  Ile  Lys  Leu  Phe  Phe  Lys  Phe  Lys  Ser
 1              5                   10                            15
```

Lys Val Lys Trp Leu Ile Lys Leu Phe Phe Lys Phe
            20                          25

(2) INFORMATION FOR SEQ ID NO:90:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.102"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:90:

Lys Trp Lys Ala Gln Phe Arg Phe Leu Lys Lys Ser Lys Val Gly Trp
 1               5                   10                  15

Leu Ile Leu Leu Phe His Lys Lys
             20

(2) INFORMATION FOR SEQ ID NO:91:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.103"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:91:

Ile Lys Ile Ser Gly Lys Trp Lys Ala Trp Lys Arg Phe Leu Lys Lys
 1               5                   10                  15

(2) INFORMATION FOR SEQ ID NO:92:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.104"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:92:

Lys Ser Lys Val Gly Trp Leu Ile Ser Leu Phe His Lys Lys ( 2 ) INFORMATION FOR SEQ ID NO:93:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.106"

( i x ) FEATURE:
        ( A ) NAME/KEY: Modified-site
        ( B ) LOCATION: C-Terminus
        ( D ) OTHER INFORMATION: /label=Amidation
                / note= "The C-Terminus is Amidated."

( x i ) SEQUENCE DESCRIPTION: SEQ ID NO:93:

Lys Ser Lys Val Gly Trp Leu Ile Thr Leu Phe His Lys Lys
1               5                       10

( 2 ) INFORMATION FOR SEQ ID NO:94:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.107"

( i x ) FEATURE:
        ( A ) NAME/KEY: Modified-site
        ( B ) LOCATION: C-Terminus
        ( D ) OTHER INFORMATION: /label=Amidation
                / note= "The C-Terminus is Amidated."

( x i ) SEQUENCE DESCRIPTION: SEQ ID NO:94:

Lys Ser Lys Val Gly Trp Leu Ile Gln Leu Phe Trp Lys Lys
1               5                       10

( 2 ) INFORMATION FOR SEQ ID NO:95:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.108"

( i x ) FEATURE:
        ( A ) NAME/KEY: Modified-site
        ( B ) LOCATION: C-Terminus
        ( D ) OTHER INFORMATION: /label=Amidation
                / note= "The C-Terminus is Amidated."

( x i ) SEQUENCE DESCRIPTION: SEQ ID NO:95:

Lys Ser Lys Val Gly Trp Leu Ile Gln Leu Phe His Lys Trp
1               5                       10

( 2 ) INFORMATION FOR SEQ ID NO:96:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.113"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:96:

Lys Ser Lys Val Gly Trp Leu Ile Gln Phe Phe His Lys Lys
 1          5                   10

( 2 ) INFORMATION FOR SEQ ID NO:97:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.114"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:97:

Lys Trp Gln Leu Arg Ser Lys Gly Lys Ile Lys Ile Phe Lys Ala
 1          5                 10            15

( 2 ) INFORMATION FOR SEQ ID NO:98:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.115 reduced"

( x i ) SEQUENCE DESCRIPTION: SEQ ID NO:98:

Met Asn Ser Gln Val Cys Glu Lys
 1             5

( 2 ) INFORMATION FOR SEQ ID NO:99:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.117"

( x i ) SEQUENCE DESCRIPTION: SEQ ID NO:99:

Gly His Tyr Ser Phe Tyr Ser Met Asp Ile Arg
 1               5                       1 0

( 2 ) INFORMATION FOR SEQ ID NO:100:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.118"

( x i ) SEQUENCE DESCRIPTION: SEQ ID NO:100:

Glu Phe Gln Leu Pro Ser Ser Gln Ile Ser Met Val Pro Asn Val Gly
 1               5                       1 0                      1 5

Leu Lys ( 2 ) INFORMATION FOR SEQ ID NO:101:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.120"

( i x ) FEATURE:
      ( A ) NAME/KEY: Modified-site
      ( B ) LOCATION: C-Terminus
      ( D ) OTHER INFORMATION: /label=Amidation
            / note= "The C-Terminus is Amidated."

( x i ) SEQUENCE DESCRIPTION: SEQ ID NO:101:

Ile Lys Ile Ser Gly Lys Trp Lys Ala Gln Lys Arg Lys Leu Lys
 1               5                       1 0                      1 5

( 2 ) INFORMATION FOR SEQ ID NO:102:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.124"

( i x ) FEATURE:
      ( A ) NAME/KEY: Modified-site
      ( B ) LOCATION: C-Terminus
      ( D ) OTHER INFORMATION: /label=Amidation
            / note= "The C-Terminus is Amidated."

( x i ) SEQUENCE DESCRIPTION: SEQ ID NO:102:

Lys Ser Lys Val Lys Trp Leu Ile Gln Leu Trp His Lys Lys
 1               5                       1 0

( 2 ) INFORMATION FOR SEQ ID NO:103:

( i ) SEQUENCE CHARACTERISTICS:

( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.125"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:103:

Lys Ser Lys Val Gly Trp Leu Ile Tyr Leu Phe His Lys Lys
 1               5                   10

( 2 ) INFORMATION FOR SEQ ID NO:104:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.127"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:104:

Lys Ser Lys Val Gly Phe Leu Ile Gln Leu Phe His Lys Lys
 1               5                   10

( 2 ) INFORMATION FOR SEQ ID NO:105:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.135"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:105:

Lys Ser Lys Val Gly Lys Leu Ile Gln Leu Pro His Lys Lys
 1               5                   10

( 2 ) INFORMATION FOR SEQ ID NO:106:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.136"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:106:

Ile Lys Ile Ser Gly Lys Trp Lys Ala Gln Glu Arg Phe Leu Lys
1               5                   10                  15

( 2 ) INFORMATION FOR SEQ ID NO:107:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.137 reduced"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:107:

Cys Lys Ser Lys Val Gly Trp Leu Ile Gln Leu Phe His Lys Lys Cys
1               5                   10                  15

( 2 ) INFORMATION FOR SEQ ID NO:108:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.138"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:108:

Lys Ser Lys Val Lys Phe Leu Ile Gln Leu Phe His Lys Lys
1               5                   10

( 2 ) INFORMATION FOR SEQ ID NO:109:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.139"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:109:

```
Lys  Ser  Lys  Val  Gly  Tyr  Leu  Ile  Gln  Leu  Phe  His  Lys  Lys
 1              5                        10
```

( 2 ) INFORMATION FOR SEQ ID NO:110:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.141"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:110:

```
Ile  Lys  Ile  Ser  Gly  Lys  Trp  Lys  Ala  Gln  Lys  Arg  Trp  Leu  Lys
 1              5                        10                       15
```

( 2 ) INFORMATION FOR SEQ ID NO:111:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.142"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:111:

```
Lys  Ser  Lys  Val  Gly  Trp  Leu  Ile  Gln  Trp  Phe  His  Lys  Lys
 1              5                        10
```

( 2 ) INFORMATION FOR SEQ ID NO:112:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.147"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:112:

Ile Lys Ile Ser Gly Lys Trp Lys Ala Glu Lys Lys Phe Leu Lys
1               5                   10                  15

( 2 ) INFORMATION FOR SEQ ID NO:113:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.149"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:113:

Lys Trp Lys Val Phe Lys Lys Ile Glu Lys Lys Ser Lys Val Gly Trp
1               5                   10                  15

Leu Ile Gln Leu Phe His Lys Lys
                20

( 2 ) INFORMATION FOR SEQ ID NO:114:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.150"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:114:

Lys Trp Ala Phe Ala Lys Lys Gln Lys Lys Arg Leu Lys Arg Gln Trp
1               5                   10                  15

Leu Lys Lys Phe
                20

( 2 ) INFORMATION FOR SEQ ID NO:115:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.151"

( i x ) FEATURE:
        ( A ) NAME/KEY: Modified-site
        ( B ) LOCATION: C-Terminus
        ( D ) OTHER INFORMATION: /label=Amidation / note= "The C-Terminus is Amidated."

( x i ) SEQUENCE DESCRIPTION: SEQ ID NO:115:

Gln Lys Arg Phe Leu Lys Lys Trp Lys Ala Gln Lys Arg Phe Leu Lys
1               5                   10                  15

Lys Trp Lys Ala Gln Lys Arg Phe Leu Lys
            20              25

( 2 ) INFORMATION FOR SEQ ID NO:116:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.152"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:116:

Lys Arg Phe Leu Lys Lys Trp Lys Ala Gln Lys Arg Phe Leu Lys Lys
1               5                   10                  15

Trp Lys Ala Gln Lys Arg Phe Leu Lys
            20              25

( 2 ) INFORMATION FOR SEQ ID NO:117:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.153"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:117:

Lys Trp Lys Ala Gln Lys Arg Phe Leu Lys Lys Trp Lys Ala Gln Lys
1               5                   10                  15

Arg Phe Leu Lys Lys Trp Lys Ala Gln Lys Arg Phe Leu Lys
            20                  25                  30

( 2 ) INFORMATION FOR SEQ ID NO:118:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.161"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:118:

Lys Ser Lys Val Lys Ala Leu Ile Gln Leu Phe His Lys Lys
1               5                   10

( 2 ) INFORMATION FOR SEQ ID NO:119:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.162"

( i x ) FEATURE:
    ( A ) NAME/KEY: Modified-site
    ( B ) LOCATION: C-Terminus
    ( D ) OTHER INFORMATION: /label=Amidation
      / note= "The C-Terminus is Amidated."

( x i ) SEQUENCE DESCRIPTION: SEQ ID NO:119:

Lys Trp Lys Ala Gln Trp Arg Phe Leu Lys Lys Ser Lys Val Gly Trp
1               5                   10                  15
Leu Ile Gln Leu Phe His Lys Lys
                20

( 2 ) INFORMATION FOR SEQ ID NO:120:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.163"

( i x ) FEATURE:
    ( A ) NAME/KEY: Modified-site
    ( B ) LOCATION: C-Terminus
    ( D ) OTHER INFORMATION: /label=Amidation
      / note= "The C-Terminus is Amidated."

( x i ) SEQUENCE DESCRIPTION: SEQ ID NO:120:

Lys Trp Lys Ala Gln Trp Arg Phe Leu Lys Lys Trp Lys Ala Gln Trp
1               5                   10                  15
Arg Phe Leu Lys
        20

( 2 ) INFORMATION FOR SEQ ID NO:121:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.166"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:121:

Lys Ser Lys Val Gly Val Leu Ile Gln Leu Phe His Lys Lys
 1              5                        10

( 2 ) INFORMATION FOR SEQ ID NO:122:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.167"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:122:

Lys Trp Lys Ala Gln Lys Arg Phe
 1              5

( 2 ) INFORMATION FOR SEQ ID NO:123:

( i ) SEQUENCE CHARACTERISTICS:
    ( A ) LENGTH: 14 amino acids
    ( B ) TYPE: amino acid
    ( D ) TOPOLOGY: circular ( i i ) MOLECULE TYPE: peptide ( i x ) FEATURE:
    ( A ) NAME/KEY: misc_feature
    ( D ) OTHER INFORMATION: "XMP.168 reduced"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:123:

Cys Lys Trp Lys Ala Gln Lys Arg Phe Leu Lys Met Ser Cys
 1              5                        10

( 2 ) INFORMATION FOR SEQ ID NO:124:

( i ) SEQUENCE CHARACTERISTICS:
    ( A ) LENGTH: 10 amino acids
    ( B ) TYPE: amino acid
    ( D ) TOPOLOGY: circular ( i i ) MOLECULE TYPE: peptide ( i x ) FEATURE:
    ( A ) NAME/KEY: misc_feature
    ( D ) OTHER INFORMATION: "XMP.169 reduced"

( i x ) FEATURE:
    ( A ) NAME/KEY: Modified-site
    ( B ) LOCATION: C-Terminus
    ( D ) OTHER INFORMATION: /label=Amidation / note= "The C-Terminus is Amidated."

( x i ) SEQUENCE DESCRIPTION: SEQ ID NO:124:

Cys Lys Trp Lys Ala Gln Lys Arg Phe Cys
1               5                   10

( 2 ) INFORMATION FOR SEQ ID NO:125:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.170"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:125:

Lys Trp Lys Ala Gln Lys Arg Phe Leu Lys Met Ser
1               5                   10

( 2 ) INFORMATION FOR SEQ ID NO:126:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.241"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:126:

Lys Ser Lys Val Gly Trp Leu Ile Leu Leu Trp His Lys Lys
1               5                   10

( 2 ) INFORMATION FOR SEQ ID NO:127:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.245"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:127:

Lys Trp Lys Ala Gln Phe Arg Phe Leu Lys Lys Ser Lys Val Gly Trp

```
          1               5                    10                      15
     Leu  Ile  Gln  Leu  Trp  His  Lys  Lys
                          20
```

(2) INFORMATION FOR SEQ ID NO:128:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.249"

(ix) FEATURE:
        (A) NAME/KEY: Modified-site
        (B) LOCATION: C-Terminus
        (D) OTHER INFORMATION: /label=Amidation
           / note= "The C-Terminus is Amidated."

(xi) SEQUENCE DESCRIPTION: SEQ ID NO:128:

```
     Lys  Ser  Lys  Val  Gly  Gly  Leu  Ile  Gln  Leu  Phe  His  Lys  Lys
      1               5                         10
```

(2) INFORMATION FOR SEQ ID NO:129:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.250"

(ix) FEATURE:
        (A) NAME/KEY: Modified-site
        (B) LOCATION: C-Terminus
        (D) OTHER INFORMATION: /label=Amidation
           / note= "The C-Terminus is Amidated."

(xi) SEQUENCE DESCRIPTION: SEQ ID NO:129:

```
     Lys  Ser  Lys  Val  Gly  Leu  Leu  Ile  Gln  Leu  Phe  His  Lys  Lys
      1               5                         10
```

(2) INFORMATION FOR SEQ ID NO:130:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.251"

(ix) FEATURE:
        (A) NAME/KEY: Modified-site
        (B) LOCATION: C-Terminus
        (D) OTHER INFORMATION: /label=Amidation
           / note= "The C-Terminus is Amidated."

(xi) SEQUENCE DESCRIPTION: SEQ ID NO:130:

```
     Lys  Ser  Lys  Val  Gly  Ile  Leu  Ile  Gln  Leu  Phe  His  Lys  Lys
      1               5                         10
```

( 2 ) INFORMATION FOR SEQ ID NO:131:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.262"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:131:

Lys Ser Lys Val Gly Trp Leu Ile Asn Leu Phe His Lys Lys
 1             5             10

( 2 ) INFORMATION FOR SEQ ID NO:132:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.263"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:132:

Lys Ser Lys Val Gly Trp Leu Ile Glu Leu Phe His Lys Lys
 1             5             10

( 2 ) INFORMATION FOR SEQ ID NO:133:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.264"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:133:

Lys Ser Lys Val Gly Trp Leu Ile Asp Leu Phe His Lys Lys
 1             5             10

( 2 ) INFORMATION FOR SEQ ID NO:134:

( i ) SEQUENCE CHARACTERISTICS:
        ( A ) LENGTH: 14 amino acids (B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.265"

(ix) FEATURE:
(A) NAME/KEY: Modified-site
(B) LOCATION: C-Terminus
(D) OTHER INFORMATION: /label=Amidation
/ note= "The C-Terminus is Amidated."

(xi) SEQUENCE DESCRIPTION: SEQ ID NO:134:

Lys Ser Lys Val Gly Trp Leu Ile Lys Leu Phe His Lys Lys
 1               5                   10

(2) INFORMATION FOR SEQ ID NO:135:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.266"

(ix) FEATURE:
(A) NAME/KEY: Modified-site
(B) LOCATION: C-Terminus
(D) OTHER INFORMATION: /label=Amidation
/ note= "The C-Terminus is Amidated."

(xi) SEQUENCE DESCRIPTION: SEQ ID NO:135:

Lys Ser Lys Val Lys Val Leu Ile Gln Leu Phe His Lys Lys
 1               5                   10

(2) INFORMATION FOR SEQ ID NO:136:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.267"

(ix) FEATURE:
(A) NAME/KEY: Modified-site
(B) LOCATION: C-Terminus
(D) OTHER INFORMATION: /label=Amidation
/ note= "The C-Terminus is Amidated."

(xi) SEQUENCE DESCRIPTION: SEQ ID NO:136:

Lys Ser Lys Val Lys Trp Ala Ile Gln Leu Phe His Lys Lys
 1               5                   10

(2) INFORMATION FOR SEQ ID NO:137:

(i) SEQUENCE CHARACTERISTICS:
(A) LENGTH: 14 amino acids
(B) TYPE: amino acid
(D) TOPOLOGY: linear (ii) MOLECULE TYPE: peptide ( i x ) FEATURE:
  ( A ) NAME/KEY: misc_feature
  ( D ) OTHER INFORMATION: "XMP.268"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:137:

Lys Ser Lys Val Gly Val Ala Ile Gln Leu Phe His Lys Lys
1               5                   10

( 2 ) INFORMATION FOR SEQ ID NO:138:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.269"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:138:

Lys Ser Lys Val Lys Val Ala Ile Gln Leu Phe His Lys Lys
1               5                   10

( 2 ) INFORMATION FOR SEQ ID NO:139:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.270"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:139:

Lys Ser Lys Val Gly Trp Leu Ile Leu Leu Phe His Lys Lys Ser
1               5                   10                  15

Lys Val Gly Trp Leu Ile Gln Leu Phe His Lys Lys
            20                  25

( 2 ) INFORMATION FOR SEQ ID NO:140:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature (D) OTHER INFORMATION: "XMP.271"

(ix) FEATURE:
 (A) NAME/KEY: Modified-site
 (B) LOCATION: C-Terminus
 (D) OTHER INFORMATION: /label=Amidation
  / note= "The C-Terminus is Amidated."

(xi) SEQUENCE DESCRIPTION: SEQ ID NO:140:

```
Lys Ser Lys Val Gly Trp Leu Ile Gln Leu Phe His Lys Lys Lys Ser
 1               5                  10                  15

Lys Val Gly Trp Leu Ile Leu Leu Phe His Lys Lys
            20                  25
```

(2) INFORMATION FOR SEQ ID NO:141:

(i) SEQUENCE CHARACTERISTICS:
  (A) LENGTH: 28 amino acids
  (B) TYPE: amino acid
  (D) TOPOLOGY: linear (ii) MOLECULE TYPE: peptide (ix) FEATURE:
  (A) NAME/KEY: misc_feature
  (D) OTHER INFORMATION: "XMP.272"

(ix) FEATURE:
  (A) NAME/KEY: Modified-site
  (B) LOCATION: C-Terminus
  (D) OTHER INFORMATION: /label=Amidation
   / note= "The C-Terminus is Amidated."

(xi) SEQUENCE DESCRIPTION: SEQ ID NO:141:

```
Lys Ser Lys Val Gly Trp Leu Ile Leu Leu Phe His Lys Lys Lys Ser
 1               5                  10                  15

Lys Val Gly Trp Leu Ile Leu Leu Phe His Lys Lys
            20                  25
```

(2) INFORMATION FOR SEQ ID NO:142:

(i) SEQUENCE CHARACTERISTICS:
  (A) LENGTH: 28 amino acids
  (B) TYPE: amino acid
  (D) TOPOLOGY: linear (ii) MOLECULE TYPE: peptide (ix) FEATURE:
  (A) NAME/KEY: misc_feature
  (D) OTHER INFORMATION: "XMP.273"

(ix) FEATURE:
  (A) NAME/KEY: Modified-site
  (B) LOCATION: C-Terminus
  (D) OTHER INFORMATION: /label=Amidation
   / note= "The C-Terminus is Amidated."

(xi) SEQUENCE DESCRIPTION: SEQ ID NO:142:

```
Lys Ser Lys Val Gly Trp Leu Ile Phe Leu Phe His Lys Lys Lys Ser
 1               5                  10                  15

Lys Val Gly Trp Leu Ile Gln Leu Phe His Lys Lys
            20                  25
```

(2) INFORMATION FOR SEQ ID NO:143:

(i) SEQUENCE CHARACTERISTICS:
  (A) LENGTH: 28 amino acids
  (B) TYPE: amino acid
  (D) TOPOLOGY: linear ( i i ) MOLECULE TYPE: peptide ( i x ) FEATURE:
    ( A ) NAME/KEY: misc_feature
    ( D ) OTHER INFORMATION: "XMP.274"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:143:

```
Lys  Ser  Lys  Val  Gly  Trp  Leu  Ile  Gln  Leu  Phe  His  Lys  Lys  Lys  Ser
 1                  5                        10                       15
Lys  Val  Gly  Trp  Leu  Ile  Phe  Leu  Phe  His  Lys  Lys
               20                        25
```

( 2 ) INFORMATION FOR SEQ ID NO:144:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.275"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:144:

```
Lys  Ser  Lys  Val  Gly  Trp  Leu  Ile  Phe  Leu  Phe  His  Lys  Lys  Lys  Ser
 1                  5                        10                       15
Lys  Val  Gly  Trp  Leu  Ile  Phe  Leu  Phe  His  Lys  Lys
               20                        25
```

( 2 ) INFORMATION FOR SEQ ID NO:145:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.276"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:145:

```
Lys  Trp  Lys  Ala  Gln  Phe  Arg  Phe  Leu  Lys  Lys  Ser  Lys  Val  Gly  Trp
 1                  5                        10                       15
Leu  Ile  Phe  Leu  Phe  His  Lys  Lys
               20
```

( 2 ) INFORMATION FOR SEQ ID NO:146:

( i ) SEQUENCE CHARACTERISTICS:

( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.278"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:146:

Ile Lys Ile Ser Gly Lys Trp Lys Ala Ala Trp Arg Phe Leu Lys
1               5                   10                  15

( 2 ) INFORMATION FOR SEQ ID NO:147:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.280"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:147:

Ile Lys Ile Ser Gly Lys Trp Lys Ala Ala Phe Arg Phe Leu Lys
1               5                   10                  15

( 2 ) INFORMATION FOR SEQ ID NO:148:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.282"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:148:

Lys Trp Lys Ala Phe Phe Arg Phe Leu Lys Lys Trp Lys Ala Phe Phe
1               5                   10                  15

Arg Phe Leu Lys
        20

( 2 ) INFORMATION FOR SEQ ID NO:149:

( i ) SEQUENCE CHARACTERISTICS:
( A ) LENGTH: 14 amino acids
( B ) TYPE: amino acid ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.283"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:149:

Lys Ser Lys Val Lys Phe Leu Ile Lys Leu Phe His Lys Lys
 1             5             10

( 2 ) INFORMATION FOR SEQ ID NO:150:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.284"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:150:

Ser Lys Val Lys Trp Leu Ile Gln Leu Phe His Lys Lys
 1             5             10

( 2 ) INFORMATION FOR SEQ ID NO:151:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.285"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:151:

Ser Lys Val Lys Trp Leu Ile Gln Leu Phe His Lys
 1             5             10

( 2 ) INFORMATION FOR SEQ ID NO:152:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:

( A ) NAME/KEY: misc_feature
( D ) OTHER INFORMATION: "XMP.286"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:152:

Lys Val Lys Trp Leu Ile Gln Leu Phe His Lys Lys
 1               5                   1 0

( 2 ) INFORMATION FOR SEQ ID NO:153:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.287"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:153:

Ser Lys Val Lys Trp Leu Ile Gln Leu Phe His
 1               5                   1 0

( 2 ) INFORMATION FOR SEQ ID NO:154:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.288"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:154:

Lys Val Lys Trp Leu Ile Gln Leu Phe His Lys
 1               5                   1 0

( 2 ) INFORMATION FOR SEQ ID NO:155:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.289"

( i x ) FEATURE:
( A ) NAME/KEY: Modified-site ( B ) LOCATION: C-Terminus
( D ) OTHER INFORMATION: /label=Amidation
/ note= "The C-Terminus is Amidated."

( x i ) SEQUENCE DESCRIPTION: SEQ ID NO:155:

Val Lys Trp Leu Ile Gln Leu Phe His Lys Lys
1               5                   1 0

( 2 ) INFORMATION FOR SEQ ID NO:156:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.290"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:156:

Ser Lys Val Lys Trp Leu Ile Gln Leu Phe
1               5                   1 0

( 2 ) INFORMATION FOR SEQ ID NO:157:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.291"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:157:

Lys Val Lys Trp Leu Ile Gln Leu Phe His
1               5                   1 0

( 2 ) INFORMATION FOR SEQ ID NO:158:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.292"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:158:

```
Val  Lys  Trp  Leu  Ile  Gln  Leu  Phe  His  Lys
 1              5                        10
```

(2) INFORMATION FOR SEQ ID NO:159:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.293"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:159:

```
Lys  Trp  Leu  Ile  Gln  Leu  Phe  His  Lys  Lys
 1              5                        10
```

(2) INFORMATION FOR SEQ ID NO:160:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.294"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:160:

```
Ser  Lys  Val  Lys  Trp  Leu  Ile  Gln  Leu
 1              5
```

(2) INFORMATION FOR SEQ ID NO:161:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.295"

(ix) FEATURE:
        (A) NAME/KEY: Modified-site
        (B) LOCATION: C-Terminus
        (D) OTHER INFORMATION: /label=Amidation
            / note= "The C-Terminus is Amidated."

(xi) SEQUENCE DESCRIPTION: SEQ ID NO:161:

```
Lys  Val  Lys  Trp  Leu  Ile  Gln  Leu  Phe
 1              5
```

( 2 ) INFORMATION FOR SEQ ID NO:162:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.296"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:162:

Val  Lys  Trp  Leu  Ile  Gln  Leu  Phe  His
     1                         5

( 2 ) INFORMATION FOR SEQ ID NO:163:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.297"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:163:

Lys  Trp  Leu  Ile  Gln  Leu  Phe  His  Lys
     1                         5

( 2 ) INFORMATION FOR SEQ ID NO:164:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.298"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:164:

Trp  Leu  Ile  Gln  Leu  Phe  His  Lys  Lys
     1                         5

( 2 ) INFORMATION FOR SEQ ID NO:165:

( i ) SEQUENCE CHARACTERISTICS:
        ( A ) LENGTH: 8 amino acids
        ( B ) TYPE: amino acid (D) TOPOLOGY: linear (ii) MOLECULE TYPE: peptide (ix) FEATURE:
- (A) NAME/KEY: misc_feature
- (D) OTHER INFORMATION: "XMP.299"

(ix) FEATURE:
- (A) NAME/KEY: Modified-site
- (B) LOCATION: C-Terminus
- (D) OTHER INFORMATION: /label=Amidation
  / note= "The C-Terminus is Amidated."

(xi) SEQUENCE DESCRIPTION: SEQ ID NO:165:

Ser Lys Val Lys Trp Leu Ile Gln
 1               5

(2) INFORMATION FOR SEQ ID NO:166:

(i) SEQUENCE CHARACTERISTICS:
- (A) LENGTH: 8 amino acids
- (B) TYPE: amino acid
- (D) TOPOLOGY: linear (ii) MOLECULE TYPE: peptide (ix) FEATURE:
- (A) NAME/KEY: misc_feature
- (D) OTHER INFORMATION: "XMP.300"

(ix) FEATURE:
- (A) NAME/KEY: Modified-site
- (B) LOCATION: C-Terminus
- (D) OTHER INFORMATION: /label=Amidation
  / note= "The C-Terminus is Amidated."

(xi) SEQUENCE DESCRIPTION: SEQ ID NO:166:

Lys Val Lys Trp Leu Ile Gln Leu
 1               5

(2) INFORMATION FOR SEQ ID NO:167:

(i) SEQUENCE CHARACTERISTICS:
- (A) LENGTH: 8 amino acids
- (B) TYPE: amino acid
- (D) TOPOLOGY: linear (ii) MOLECULE TYPE: peptide (ix) FEATURE:
- (A) NAME/KEY: misc_feature
- (D) OTHER INFORMATION: "XMP.301"

(ix) FEATURE:
- (A) NAME/KEY: Modified-site
- (B) LOCATION: C-Terminus
- (D) OTHER INFORMATION: /label=Amidation
  / note= "The C-Terminus is Amidated."

(xi) SEQUENCE DESCRIPTION: SEQ ID NO:167:

Val Lys Trp Leu Ile Gln Leu Phe
 1               5

(2) INFORMATION FOR SEQ ID NO:168:

(i) SEQUENCE CHARACTERISTICS:
- (A) LENGTH: 8 amino acids
- (B) TYPE: amino acid
- (D) TOPOLOGY: linear (ii) MOLECULE TYPE: peptide (ix) FEATURE:

(A) NAME/KEY: misc_feature
                (D) OTHER INFORMATION: "XMP.302"

(ix) FEATURE:
                (A) NAME/KEY: Modified-site
                (B) LOCATION: C-Terminus
                (D) OTHER INFORMATION: /label=Amidation
                    / note= "The C-Terminus is Amidated."

(xi) SEQUENCE DESCRIPTION: SEQ ID NO:168:

Lys  Trp  Leu  Ile  Gln  Leu  Phe  His
         1                    5

(2) INFORMATION FOR SEQ ID NO:169:

(i) SEQUENCE CHARACTERISTICS:
                (A) LENGTH: 8 amino acids
                (B) TYPE: amino acid
                (D) TOPOLOGY: linear (ii) MOLECULE TYPE: peptide (ix) FEATURE:
                (A) NAME/KEY: misc_feature
                (D) OTHER INFORMATION: "XMP.303"

(ix) FEATURE:
                (A) NAME/KEY: Modified-site
                (B) LOCATION: C-Terminus
                (D) OTHER INFORMATION: /label=Amidation
                    / note= "The C-Terminus is Amidated."

(xi) SEQUENCE DESCRIPTION: SEQ ID NO:169:

Trp  Leu  Ile  Gln  Leu  Phe  His  Lys
         1                    5

(2) INFORMATION FOR SEQ ID NO:170:

(i) SEQUENCE CHARACTERISTICS:
                (A) LENGTH: 8 amino acids
                (B) TYPE: amino acid
                (D) TOPOLOGY: linear (ii) MOLECULE TYPE: peptide (ix) FEATURE:
                (A) NAME/KEY: misc_feature
                (D) OTHER INFORMATION: "XMP.304"

(ix) FEATURE:
                (A) NAME/KEY: Modified-site
                (B) LOCATION: C-Terminus
                (D) OTHER INFORMATION: /label=Amidation
                    / note= "The C-Terminus is Amidated."

(xi) SEQUENCE DESCRIPTION: SEQ ID NO:170:

Leu  Ile  Gln  Leu  Phe  His  Lys  Lys
         1                    5

(2) INFORMATION FOR SEQ ID NO:171:

(i) SEQUENCE CHARACTERISTICS:
                (A) LENGTH: 8 amino acids
                (B) TYPE: amino acid
                (D) TOPOLOGY: linear (ii) MOLECULE TYPE: peptide (ix) FEATURE:
                (A) NAME/KEY: misc_feature
                (D) OTHER INFORMATION: "XMP.305"

(ix) FEATURE:
                (A) NAME/KEY: Modified-site ( B ) LOCATION: C-Terminus
( D ) OTHER INFORMATION: /label=Amidation
/ note= "The C-Terminus is Amidated."

( x i ) SEQUENCE DESCRIPTION: SEQ ID NO:171:

Ser Lys Val Lys Trp Leu Ile Gln
1               5

( 2 ) INFORMATION FOR SEQ ID NO:172:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.306"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:172:

Ser Lys Val Lys Trp Leu Ile
1               5

( 2 ) INFORMATION FOR SEQ ID NO:173:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.307"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:173:

Val Lys Trp Leu Ile Gln Leu
1               5

( 2 ) INFORMATION FOR SEQ ID NO:174:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.308"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:174:

```
Lys  Trp  Leu  Ile  Gln  Leu  Phe
 1                    5
```

( 2 ) INFORMATION FOR SEQ ID NO:175:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.309"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:175:

```
Trp  Leu  Ile  Gln  Leu  Phe  His
 1                    5
```

( 2 ) INFORMATION FOR SEQ ID NO:176:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.310"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:176:

```
Leu  Ile  Gln  Leu  Phe  His  Lys
 1                    5
```

( 2 ) INFORMATION FOR SEQ ID NO:177:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.311"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:177:

```
Ile  Gln  Leu  Phe  His  Lys  Lys
 1                    5
```

( 2 ) INFORMATION FOR SEQ ID NO:178:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.312"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:178:

Ser  Lys  Val  Lys  Trp  Leu
     1                       5

( 2 ) INFORMATION FOR SEQ ID NO:179:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.313"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:179:

Lys  Val  Lys  Trp  Leu  Ile
     1                       5

( 2 ) INFORMATION FOR SEQ ID NO:180:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.314"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:180:

Val  Lys  Trp  Leu  Ile  Gln
     1                       5

( 2 ) INFORMATION FOR SEQ ID NO:181:

( i ) SEQUENCE CHARACTERISTICS:
        ( A ) LENGTH: 6 amino acids
        ( B ) TYPE: amino acid ( D ) TOPOLOGY: linear ( i i ) MOLECULE TYPE: peptide ( i x ) FEATURE:
              ( A ) NAME/KEY: misc_feature
              ( D ) OTHER INFORMATION: "XMP.315"

( i x ) FEATURE:
              ( A ) NAME/KEY: Modified-site
              ( B ) LOCATION: C-Terminus
              ( D ) OTHER INFORMATION: /label=Amidation
                         / note= "The C-Terminus is Amidated."

( x i ) SEQUENCE DESCRIPTION: SEQ ID NO:181:

Lys  Trp  Leu  Ile  Gln  Leu
     1                    5

( 2 ) INFORMATION FOR SEQ ID NO:182:

( i ) SEQUENCE CHARACTERISTICS:
              ( A ) LENGTH: 6 amino acids
              ( B ) TYPE: amino acid
              ( D ) TOPOLOGY: linear ( i i ) MOLECULE TYPE: peptide ( i x ) FEATURE:
              ( A ) NAME/KEY: misc_feature
              ( D ) OTHER INFORMATION: "XMP.316"

( i x ) FEATURE:
              ( A ) NAME/KEY: Modified-site
              ( B ) LOCATION: C-Terminus
              ( D ) OTHER INFORMATION: /label=Amidation
                         / note= "The C-Terminus is Amidated."

( x i ) SEQUENCE DESCRIPTION: SEQ ID NO:182:

Trp  Leu  Ile  Gln  Leu  Phe
     1                    5

( 2 ) INFORMATION FOR SEQ ID NO:183:

( i ) SEQUENCE CHARACTERISTICS:
              ( A ) LENGTH: 6 amino acids
              ( B ) TYPE: amino acid
              ( D ) TOPOLOGY: linear ( i i ) MOLECULE TYPE: peptide ( i x ) FEATURE:
              ( A ) NAME/KEY: misc_feature
              ( D ) OTHER INFORMATION: "XMP.317"

( i x ) FEATURE:
              ( A ) NAME/KEY: Modified-site
              ( B ) LOCATION: C-Terminus
              ( D ) OTHER INFORMATION: /label=Amidation
                         / note= "The C-Terminus is Amidated."

( x i ) SEQUENCE DESCRIPTION: SEQ ID NO:183:

Trp  Leu  Ile  Gln  Leu  Phe
     1                    5

( 2 ) INFORMATION FOR SEQ ID NO:184:

( i ) SEQUENCE CHARACTERISTICS:
              ( A ) LENGTH: 6 amino acids
              ( B ) TYPE: amino acid
              ( D ) TOPOLOGY: linear ( i i ) MOLECULE TYPE: peptide ( i x ) FEATURE:

( A ) NAME/KEY: misc_feature
( D ) OTHER INFORMATION: "XMP.318"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:184:

Ile Gln Leu Phe His Lys
1               5

( 2 ) INFORMATION FOR SEQ ID NO:185:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.319"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:185:

Gln Leu Phe His Lys Lys
1               5

( 2 ) INFORMATION FOR SEQ ID NO:186:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.320"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:186:

Trp Leu Ile Gln Leu
1               5

( 2 ) INFORMATION FOR SEQ ID NO:187:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.321"

( i x ) FEATURE:
( A ) NAME/KEY: Modified-site (B) LOCATION: C-Terminus
(D) OTHER INFORMATION: /label=Amidation
/ note= "The C-Terminus is Amidated."

(xi) SEQUENCE DESCRIPTION: SEQ ID NO:187:

Trp Leu Ile Gln Leu Lys
1               5

(2) INFORMATION FOR SEQ ID NO:188:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.322"

(ix) FEATURE:
(A) NAME/KEY: Modified-site
(B) LOCATION: C-Terminus
(D) OTHER INFORMATION: /label=Amidation
/ note= "The C-Terminus is Amidated."

(xi) SEQUENCE DESCRIPTION: SEQ ID NO:188:

Trp Leu Ile Gln Leu Lys Lys
1               5

(2) INFORMATION FOR SEQ ID NO:189:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.323"

(ix) FEATURE:
(A) NAME/KEY: Modified-site
(B) LOCATION: C-Terminus
(D) OTHER INFORMATION: /label=Amidation
/ note= "The C-Terminus is Amidated."

(xi) SEQUENCE DESCRIPTION: SEQ ID NO:189:

Lys Trp Leu Ile Gln Leu Lys
1               5

(2) INFORMATION FOR SEQ ID NO:190:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.324"

(ix) FEATURE:
(A) NAME/KEY: Modified-site
(B) LOCATION: C-Terminus
(D) OTHER INFORMATION: /label=Amidation
/ note= "The C-Terminus is Amidated."

(xi) SEQUENCE DESCRIPTION: SEQ ID NO:190:

Lys  Trp  Leu  Ile  Gln  Leu  Lys
         1                 5

( 2 ) INFORMATION FOR SEQ ID NO:191:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.325"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:191:

Lys  Lys  Trp  Leu  Ile  Gln  Leu
         1                 5

( 2 ) INFORMATION FOR SEQ ID NO:192:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.326"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:192:

Lys  Lys  Trp  Leu  Ile  Gln  Leu  Lys
         1                 5

( 2 ) INFORMATION FOR SEQ ID NO:193:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.327"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:193:

Lys  Lys  Trp  Leu  Ile  Gln  Leu  Lys  Lys
         1                 5

( 2 ) INFORMATION FOR SEQ ID NO:194:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.328"

( x i ) SEQUENCE DESCRIPTION: SEQ ID NO:194:

```
Pro Ile Lys Ile Ser Gly Lys Trp Lys Ala Gln Lys Arg Phe Leu Lys
 1               5                  10                  15

Lys Ser Lys Val Gly Trp Leu Ile Gln Leu Phe His Lys Lys Ile
                20                  25                  30
```

( 2 ) INFORMATION FOR SEQ ID NO:195:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.329"

( i x ) FEATURE:
        ( A ) NAME/KEY: Modified-site
        ( B ) LOCATION: C-Terminus
        ( D ) OTHER INFORMATION: /label=Amidation
             / note= "The C-Terminus is Amidated."

( x i ) SEQUENCE DESCRIPTION: SEQ ID NO:195:

```
Lys Lys Val Val Gln Val Val Lys Lys
 1               5
```

( 2 ) INFORMATION FOR SEQ ID NO:196:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.330"

( i x ) FEATURE:
        ( A ) NAME/KEY: Modified-site
        ( B ) LOCATION: C-Terminus
        ( D ) OTHER INFORMATION: /label=Amidation
             / note= "The C-Terminus is Amidated."

( x i ) SEQUENCE DESCRIPTION: SEQ ID NO:196:

```
Trp Leu Ile Gln
 1
```

( 2 ) INFORMATION FOR SEQ ID NO:197:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.331"

( i x ) FEATURE:
  ( A ) NAME/KEY: Modified-site
  ( B ) LOCATION: 1
  ( D ) OTHER INFORMATION: /label=Acetylated
   / note= "Position 1 is acetylated."

( i x ) FEATURE:
  ( A ) NAME/KEY: Modified-site
  ( B ) LOCATION: C-Terminus
  ( D ) OTHER INFORMATION: /label=Amidation
   / note= "The C-Terminus is Amidated."

( x i ) SEQUENCE DESCRIPTION: SEQ ID NO:197:

Lys Lys Trp Leu Ile Gln Leu Lys Lys
 1      5

( 2 ) INFORMATION FOR SEQ ID NO:198:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.335"

( i x ) FEATURE:
  ( A ) NAME/KEY: Modified-site
  ( B ) LOCATION: C-Terminus
  ( D ) OTHER INFORMATION: /label=Amidation
   / note= "The C-Terminus is Amidated."

( x i ) SEQUENCE DESCRIPTION: SEQ ID NO:198:

Pro Lys Trp Leu Ile Gln Leu Lys Lys
 1      5

( 2 ) INFORMATION FOR SEQ ID NO:199:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.336"

( i x ) FEATURE:
  ( A ) NAME/KEY: Modified-site
  ( B ) LOCATION: C-Terminus
  ( D ) OTHER INFORMATION: /label=Amidation
   / note= "The C-Terminus is Amidated."

( x i ) SEQUENCE DESCRIPTION: SEQ ID NO:199:

Arg Arg Trp Leu Ile Gln Leu Arg Arg
 1      5

( 2 ) INFORMATION FOR SEQ ID NO:200:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.337"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:200:

His His Trp Leu Ile Gln Leu His His
 1               5

( 2 ) INFORMATION FOR SEQ ID NO:201:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.343"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:201:

Lys Lys Val Leu Ile Gln Leu Lys Lys
 1               5

( 2 ) INFORMATION FOR SEQ ID NO:202:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.344"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:202:

Lys Lys Trp Ala Ile Gln Leu Lys Lys
 1               5

( 2 ) INFORMATION FOR SEQ ID NO:203:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.345"

( i x ) FEATURE:
   ( A ) NAME/KEY: Modified-site
   ( B ) LOCATION: C-Terminus
   ( D ) OTHER INFORMATION: /label=Amidation
      / note= "The C-Terminus is Amidated."

( x i ) SEQUENCE DESCRIPTION: SEQ ID NO:203:

Lys Lys Trp Leu Ile Gln Ala Lys Lys
 1               5

( 2 ) INFORMATION FOR SEQ ID NO:204:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.348"

( i x ) FEATURE:
      ( A ) NAME/KEY: Modified-site
      ( B ) LOCATION: C-Terminus
      ( D ) OTHER INFORMATION: /label=Amidation
         / note= "The C-Terminus is Amidated."

( x i ) SEQUENCE DESCRIPTION: SEQ ID NO:204:

Lys Lys Lys Trp Leu Ile Gln Leu Lys Lys
 1               5                   1 0

( 2 ) INFORMATION FOR SEQ ID NO:205:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.349"

( i x ) FEATURE:
      ( A ) NAME/KEY: Modified-site
      ( B ) LOCATION: C-Terminus
      ( D ) OTHER INFORMATION: /label=Amidation
         / note= "The C-Terminus is Amidated."

( x i ) SEQUENCE DESCRIPTION: SEQ ID NO:205:

Lys Lys Trp Leu Ile Gln Leu Lys Lys Lys
 1               5                   1 0

( 2 ) INFORMATION FOR SEQ ID NO:206:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.350"

( i x ) FEATURE:
      ( A ) NAME/KEY: Modified-site
      ( B ) LOCATION: C-Terminus
      ( D ) OTHER INFORMATION: /label=Amidation / note= "The C-Terminus is Amidated."

( x i ) SEQUENCE DESCRIPTION: SEQ ID NO:206:

```
Lys  Lys  Lys  Trp  Leu  Ile  Gln  Leu  Lys  Lys  Lys
 1                     5                      10
```

( 2 ) INFORMATION FOR SEQ ID NO:207:

( i ) SEQUENCE CHARACTERISTICS:
       ( A ) LENGTH: 10 amino acids
       ( B ) TYPE: amino acid
       ( D ) TOPOLOGY: linear ( i i ) MOLECULE TYPE: peptide ( i x ) FEATURE:
       ( A ) NAME/KEY: misc_feature
       ( D ) OTHER INFORMATION: "XMP.351"

( i x ) FEATURE:
       ( A ) NAME/KEY: Modified-site
       ( B ) LOCATION: C-Terminus
       ( D ) OTHER INFORMATION: /label=Amidation
           / note= "The C-Terminus is Amidated."

( x i ) SEQUENCE DESCRIPTION: SEQ ID NO:207:

```
Lys  Lys  Trp  Leu  Ile  Gln  Leu  Phe  Lys  Lys
 1                5                      10
```

( 2 ) INFORMATION FOR SEQ ID NO:208:

( i ) SEQUENCE CHARACTERISTICS:
       ( A ) LENGTH: 11 amino acids
       ( B ) TYPE: amino acid
       ( D ) TOPOLOGY: linear ( i i ) MOLECULE TYPE: peptide ( i x ) FEATURE:
       ( A ) NAME/KEY: misc_feature
       ( D ) OTHER INFORMATION: "XMP.352"

( i x ) FEATURE:
       ( A ) NAME/KEY: Modified-site
       ( B ) LOCATION: C-Terminus
       ( D ) OTHER INFORMATION: /label=Amidation
           / note= "The C-Terminus is Amidated."

( x i ) SEQUENCE DESCRIPTION: SEQ ID NO:208:

```
Lys  Lys  Trp  Leu  Ile  Gln  Leu  Phe  His  Lys  Lys
 1                5                       10
```

( 2 ) INFORMATION FOR SEQ ID NO:209:

( i ) SEQUENCE CHARACTERISTICS:
       ( A ) LENGTH: 10 amino acids
       ( B ) TYPE: amino acid
       ( D ) TOPOLOGY: linear ( i i ) MOLECULE TYPE: peptide ( i x ) FEATURE:
       ( A ) NAME/KEY: misc_feature
       ( D ) OTHER INFORMATION: "XMP.353"

( x i ) SEQUENCE DESCRIPTION: SEQ ID NO:209:

```
Pro  Trp  Leu  Ile  Gln  Leu  Phe  His  Lys  Lys
 1                5                      10
```

( 2 ) INFORMATION FOR SEQ ID NO:210:

( i ) SEQUENCE CHARACTERISTICS:

( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.354"

( i x ) FEATURE:
( A ) NAME/KEY: Modified-site
( B ) LOCATION: 1
( D ) OTHER INFORMATION: /label=Acetylated
/ note= "Position 1 is acetylated."

( x i ) SEQUENCE DESCRIPTION: SEQ ID NO:210:

Pro Trp Leu Ile Gln Leu Phe His Lys Lys
1               5                   10

( 2 ) INFORMATION FOR SEQ ID NO:211:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.355"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( x i ) SEQUENCE DESCRIPTION: SEQ ID NO:211:

Pro Trp Leu Ile Gln Leu Phe His Lys Lys
1               5                   10

( 2 ) INFORMATION FOR SEQ ID NO:212:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.356"

( i x ) FEATURE:
( A ) NAME/KEY: Modified-site
( B ) LOCATION: C-Terminus
( D ) OTHER INFORMATION: /label=Amidation
/ note= "The C-Terminus is Amidated."

( i x ) FEATURE:
( A ) NAME/KEY: Modified-site
( B ) LOCATION: 1
( D ) OTHER INFORMATION: /label=Acetylated
/ note= "Position 1 is acetylated."

( x i ) SEQUENCE DESCRIPTION: SEQ ID NO:212:

Pro Trp Leu Ile Gln Leu Phe His Lys Lys
1               5                   10

( 2 ) INFORMATION FOR SEQ ID NO:213:

( i ) SEQUENCE CHARACTERISTICS:
   ( A ) LENGTH: 10 amino acids
   ( B ) TYPE: amino acid
   ( D ) TOPOLOGY: linear ( i i ) MOLECULE TYPE: peptide ( i x ) FEATURE:
   ( A ) NAME/KEY: misc_feature
   ( D ) OTHER INFORMATION: "XMP.357"

( i x ) FEATURE:
   ( A ) NAME/KEY: Modified-site
   ( B ) LOCATION: C-Terminus
   ( D ) OTHER INFORMATION: /label=Amidation
       / note= "The C-Terminus is Amidated."

( x i ) SEQUENCE DESCRIPTION: SEQ ID NO:213:

Lys Trp Leu Ile Gln Leu Phe His Lys Pro
 1               5                  10

( 2 ) INFORMATION FOR SEQ ID NO:214:

( i ) SEQUENCE CHARACTERISTICS:
       ( A ) LENGTH: 10 amino acids
       ( B ) TYPE: amino acid
       ( D ) TOPOLOGY: linear ( i i ) MOLECULE TYPE: peptide ( i x ) FEATURE:
   ( A ) NAME/KEY: misc_feature
   ( D ) OTHER INFORMATION: "XMP.358"

( i x ) FEATURE:
   ( A ) NAME/KEY: Modified-site
   ( B ) LOCATION: C-Terminus
   ( D ) OTHER INFORMATION: /label=Amidation
       / note= "The C-Terminus is Amidated."

( x i ) SEQUENCE DESCRIPTION: SEQ ID NO:214:

Lys Lys Trp Leu Ile Gln Leu Phe His Pro
 1               5                  10

( 2 ) INFORMATION FOR SEQ ID NO:215:

( i ) SEQUENCE CHARACTERISTICS:
       ( A ) LENGTH: 10 amino acids
       ( B ) TYPE: amino acid
       ( D ) TOPOLOGY: linear ( i i ) MOLECULE TYPE: peptide ( i x ) FEATURE:
   ( A ) NAME/KEY: misc_feature
   ( D ) OTHER INFORMATION: "XMP.373"

( i x ) FEATURE:
   ( A ) NAME/KEY: Modified-site
   ( B ) LOCATION: 1
   ( D ) OTHER INFORMATION: /label=Acetylated
       / note= "Position 1 is acetylated."

( i x ) FEATURE:
   ( A ) NAME/KEY: Modified-site
   ( B ) LOCATION: C-Terminus
   ( D ) OTHER INFORMATION: /label=Amidation
       / note= "The C-Terminus is Amidated."

( x i ) SEQUENCE DESCRIPTION: SEQ ID NO:215:

Lys Trp Leu Ile Gln Leu Phe His Lys Lys
 1               5                  10

( 2 ) INFORMATION FOR SEQ ID NO:216:

(  i  ) SEQUENCE CHARACTERISTICS:
   ( A ) LENGTH: 10 amino acids
   ( B ) TYPE: amino acid
   ( D ) TOPOLOGY: linear (  i i  ) MOLECULE TYPE: peptide (  i x  ) FEATURE:
   ( A ) NAME/KEY: misc_feature
   ( D ) OTHER INFORMATION: "XMP.377"

(  i x  ) FEATURE:
   ( A ) NAME/KEY: Modified-site
   ( B ) LOCATION: C-Terminus
   ( D ) OTHER INFORMATION: /label=Amidation
       / note= "The C-Terminus is Amidated."

(  x i  ) SEQUENCE DESCRIPTION: SEQ ID NO:216:

Lys Lys Lys Trp Ala Ile Gln Leu Lys Lys
 1               5                  10

( 2 ) INFORMATION FOR SEQ ID NO:217:

(  i  ) SEQUENCE CHARACTERISTICS:
   ( A ) LENGTH: 8 amino acids
   ( B ) TYPE: amino acid
   ( D ) TOPOLOGY: linear (  i i  ) MOLECULE TYPE: peptide (  i x  ) FEATURE:
   ( A ) NAME/KEY: misc_feature
   ( D ) OTHER INFORMATION: "XMP.378"

(  i x  ) FEATURE:
   ( A ) NAME/KEY: Modified-site
   ( B ) LOCATION: C-Terminus
   ( D ) OTHER INFORMATION: /label=Amidation
       / note= "The C-Terminus is Amidated."

(  x i  ) SEQUENCE DESCRIPTION: SEQ ID NO:217:

Pro Trp Ala Ile Gln Leu Lys Lys
 1               5

( 2 ) INFORMATION FOR SEQ ID NO:218:

(  i  ) SEQUENCE CHARACTERISTICS:
   ( A ) LENGTH: 10 amino acids
   ( B ) TYPE: amino acid
   ( D ) TOPOLOGY: linear (  i i  ) MOLECULE TYPE: peptide (  i x  ) FEATURE:
   ( A ) NAME/KEY: misc_feature
   ( D ) OTHER INFORMATION: "XMP.379"

(  i x  ) FEATURE:
   ( A ) NAME/KEY: Modified-site
   ( B ) LOCATION: C-Terminus
   ( D ) OTHER INFORMATION: /label=Amidation
       / note= "The C-Terminus is Amidated."

(  x i  ) SEQUENCE DESCRIPTION: SEQ ID NO:218:

Lys Lys Pro Trp Ala Ile Gln Leu Lys Lys
 1               5                  10

( 2 ) INFORMATION FOR SEQ ID NO:219:

(  i  ) SEQUENCE CHARACTERISTICS:
   ( A ) LENGTH: 9 amino acids
   ( B ) TYPE: amino acid
   ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.380"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:219:

Lys Lys Gln Leu Leu Leu Leu Lys Lys
 1            5

( 2 ) INFORMATION FOR SEQ ID NO:220:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.381"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:220:

Lys Lys Leu Gln Leu Leu Leu Lys Lys
 1            5

( 2 ) INFORMATION FOR SEQ ID NO:221:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.382:

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:221:

Lys Lys Leu Leu Gln Leu Leu Lys Lys
 1            5

( 2 ) INFORMATION FOR SEQ ID NO:222:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature (D) OTHER INFORMATION: "XMP.383"

(ix) FEATURE:
    (A) NAME/KEY: Modified-site
    (B) LOCATION: C-Terminus
    (D) OTHER INFORMATION: /label=Amidation
        / note= "The C-Terminus is Amidated."

(xi) SEQUENCE DESCRIPTION: SEQ ID NO:222:

Lys Lys Leu Leu Leu Gln Leu Lys Lys
 1                5

(2) INFORMATION FOR SEQ ID NO:223:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (ix) FEATURE:
    (A) NAME/KEY: misc_feature
    (D) OTHER INFORMATION: "XMP.384"

(ix) FEATURE:
    (A) NAME/KEY: Modified-site
    (B) LOCATION: C-Terminus
    (D) OTHER INFORMATION: /label=Amidation
        / note= "The C-Terminus is Amidated."

(xi) SEQUENCE DESCRIPTION: SEQ ID NO:223:

Lys Lys Leu Leu Leu Leu Gln Lys Lys
 1                5

(2) INFORMATION FOR SEQ ID NO:224:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (ix) FEATURE:
    (A) NAME/KEY: misc_feature
    (D) OTHER INFORMATION: "XMP.385"

(ix) FEATURE:
    (A) NAME/KEY: Modified-site
    (B) LOCATION: C-Terminus
    (D) OTHER INFORMATION: /label=Amidation
        / note= "The C-Terminus is Amidated."

(xi) SEQUENCE DESCRIPTION: SEQ ID NO:224:

Lys Lys Leu Leu Leu Leu Leu Lys Lys
 1                5

(2) INFORMATION FOR SEQ ID NO:225:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (ix) FEATURE:
    (A) NAME/KEY: misc_feature
    (D) OTHER INFORMATION: "XMP.386"

(ix) FEATURE:
    (A) NAME/KEY: Modified-site
    (B) LOCATION: C-Terminus ( D ) OTHER INFORMATION: /label=Amidation
/ note= "The C-Terminus is Amidated."

( x i ) SEQUENCE DESCRIPTION: SEQ ID NO:225:

Lys Trp Ala Ile Gln Leu Phe His Lys Lys Ile
1               5                    10

( 2 ) INFORMATION FOR SEQ ID NO:226:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.387"

( i x ) FEATURE:
      ( A ) NAME/KEY: Modified-site
      ( B ) LOCATION: C-Terminus
      ( D ) OTHER INFORMATION: /label=Amidation
/ note= "The C-Terminus is Amidated."

( x i ) SEQUENCE DESCRIPTION: SEQ ID NO:226:

Pro Trp Ala Ile Gln Leu Phe His Lys Lys
1               5                    10

( 2 ) INFORMATION FOR SEQ ID NO:227:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.388"

( i x ) FEATURE:
      ( A ) NAME/KEY: Modified-site
      ( B ) LOCATION: C-Terminus
      ( D ) OTHER INFORMATION: /label=Amidation
/ note= "The C-Terminus is Amidated."

( x i ) SEQUENCE DESCRIPTION: SEQ ID NO:227:

Gly Trp Leu Ile Gln Leu Phe His Lys Lys
1               5                    10

( 2 ) INFORMATION FOR SEQ ID NO:228:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.389"

( i x ) FEATURE:
      ( A ) NAME/KEY: Modified-site
      ( B ) LOCATION: C-Terminus
      ( D ) OTHER INFORMATION: /label=Amidation
/ note= "The C-Terminus is Amidated."

( x i ) SEQUENCE DESCRIPTION: SEQ ID NO:228:

```
        Lys  Gly  Trp  Leu  Ile  Gln  Leu  Phe  His  Lys  Lys
         1              5                        10
```

( 2 ) INFORMATION FOR SEQ ID NO:229:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.390"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:229:

```
        Lys  Pro  Trp  Leu  Ile  Gln  Leu  Phe  His  Lys  Lys
         1              5                        10
```

( 2 ) INFORMATION FOR SEQ ID NO:230:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.391"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:230:

```
        Lys  Val  Gly  Trp  Leu  Ile  Gln  Leu  Phe  His  Lys  Lys
         1              5                        10
```

( 2 ) INFORMATION FOR SEQ ID NO:231:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.392"

( i x ) FEATURE:
        ( A ) NAME/KEY: Modified-site
        ( B ) LOCATION: C-Terminus
        ( D ) OTHER INFORMATION: /label=Amidation
            / note= "The C-Terminus is Amidated."

( x i ) SEQUENCE DESCRIPTION: SEQ ID NO:231:

```
        Lys  Val  Pro  Trp  Leu  Ile  Gln  Leu  Phe  His  Lys  Lys
         1              5                        10
```

( 2 ) INFORMATION FOR SEQ ID NO:232:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.393"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:232:

Lys Ser Lys Val Pro Trp Leu Ile Gln Leu Phe His Lys Lys
1               5                   10

( 2 ) INFORMATION FOR SEQ ID NO:233:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.399"

( i x ) FEATURE:
    ( A ) NAME/KEY: Modified-site
    ( B ) LOCATION: C-Terminus
    ( D ) OTHER INFORMATION: /label=Amidation
        / note= "The C-Terminus is Amidated."

( x i ) SEQUENCE DESCRIPTION: SEQ ID NO:233:

Lys Ser Lys Val Gly Trp Leu Ile Phe Leu Trp His Lys Lys
1               5                   10

( 2 ) INFORMATION FOR SEQ ID NO:234:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.406"

( x i ) SEQUENCE DESCRIPTION: SEQ ID NO:234:

Pro Lys Ser Lys Val Gly Ala Leu Ile Gln Leu Phe His Lys Lys
1               5                   10                  15

( 2 ) INFORMATION FOR SEQ ID NO:235:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.407"

(x i) SEQUENCE DESCRIPTION: SEQ ID NO:235:

Pro Lys Ser Lys Val Gly Ala Leu Ile Gln Leu Phe His Lys Lys Asp
1               5                   10                  15

(2) INFORMATION FOR SEQ ID NO:236:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.409"

(i x) FEATURE:
        (A) NAME/KEY: Modified-site
        (B) LOCATION: C-Terminus
        (D) OTHER INFORMATION: /label=Amidation
            / note= "The C-Terminus is Amidated."

(x i) SEQUENCE DESCRIPTION: SEQ ID NO:236:

Ser Lys Trp Ala Ile Gln Leu Lys Lys
1               5

(2) INFORMATION FOR SEQ ID NO:237:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.412"

(x i) SEQUENCE DESCRIPTION: SEQ ID NO:237:

Leu Lys Lys Lys Trp Ala Ile Gln
1               5

(2) INFORMATION FOR SEQ ID NO:238:

(i) SEQUENCE CHARACTERISTICS:
        (A) LENGTH: 19 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.413"

(x i) SEQUENCE DESCRIPTION: SEQ ID NO:238:

Lys Trp Lys Ala Gln Lys Arg Leu Lys Lys Trp Lys Ala Ala Ala Arg
1               5                   10                  15
Phe Leu Lys (2) INFORMATION FOR SEQ ID NO:239:

(i) SEQUENCE CHARACTERISTICS:
        (A) LENGTH: 14 amino acids
        (B) TYPE: amino acid
        (D) TOPOLOGY: linear (i i) MOLECULE TYPE: peptide ( i x ) FEATURE:
  ( A ) NAME/KEY: misc_feature
  ( D ) OTHER INFORMATION: "XMP.418"

( i x ) FEATURE:
  ( A ) NAME/KEY: Modified-site
  ( B ) LOCATION: C-Terminus
  ( D ) OTHER INFORMATION: /label=Amidation
    / note= "The C-Terminus is Amidated."

( x i ) SEQUENCE DESCRIPTION: SEQ ID NO:239:

```
Lys  Ser  Lys  Val  Pro  Trp  Leu  Ile  Gln  Leu  Phe  His  Lys  Lys
 1                    5                   10
```

( 2 ) INFORMATION FOR SEQ ID NO:240:

( i ) SEQUENCE CHARACTERISTICS:
  ( A ) LENGTH: 78 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:240:

```
GCTATCTGCG  CATTGGATCC  GATCAAAATC  TCGGGTAAAT  GGAAGGCCCA  GAAACGCTTT          60

CTGAAAAAGT  CGAAAGTG                                                            78
```

( 2 ) INFORMATION FOR SEQ ID NO:241:

( i ) SEQUENCE CHARACTERISTICS:
  ( A ) LENGTH: 75 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:241:

```
GCGGGCTCTC  GAGCTTTAAA  TCTTTTTATG  AAACAGCTGG  ATCAGCCAAC  CCACTTTCGA          60

CTTTTTCAGA  AAGCG                                                               75
```

( 2 ) INFORMATION FOR SEQ ID NO:242:

( i ) SEQUENCE CHARACTERISTICS:
  ( A ) LENGTH: 54 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:242:

```
GATCCGAAGT  CTAAAGTGGG  GKYCCTGATC  CAGCTGTTCC  ACAAAAGTA  AAGC                 54
```

( 2 ) INFORMATION FOR SEQ ID NO:243:

( i ) SEQUENCE CHARACTERISTICS:
  ( A ) LENGTH: 54 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:243:

```
TCGAGTCTTA  CTTTTTGTGA  AGCAGCTGGA  TCAGGRMCCC  CACTTTAGAC  TTCG                54
```

( 2 ) INFORMATION FOR SEQ ID NO:244:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:244:

```
ACTTGGGCCC CTACCTTGGA TTTTGGGTCC TTTTTGTGGA ACAGCTG                47
```

( 2 ) INFORMATION FOR SEQ ID NO:245:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:245:

```
TGGAACGATA AATGCCCATG                                              20
```

( 2 ) INFORMATION FOR SEQ ID NO:246:

( i ) SEQUENCE CHARACTERISTICS:
        ( A ) LENGTH: 813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( D ) OTHER INFORMATION: "gelonin"

( x i ) SEQUENCE DESCRIPTION: SEQ ID NO:246:

```
GGGCTAGATA CCGTGTCATT CTCAACCAAA GGTGCCACTT ATATTACCTA CGTGAATTTC   60
TTGAATGAGC TACGAGTTAA ATTGAAACCC GAAGGTAACA GCCATGGAAT CCCATTGCTG  120
CGCAAAAAAT GTGATGATCC TGGAAAGTGT TTCGTTTTGG TAGCGCTTTC AAATGACAAT  180
GGACAGTTGG CGGAAATAGC TATAGATGTT ACAAGTGTTT ATGTGGTGGG CTATCAAGTA  240
AGAAACAGAT CTTACTTCTT TAAAGATGCT CCAGATGCTG CTTACGAAGG CCTCTTCAAA  300
AACACAATTA AAACAAGACT TCATTTTGGC GGCAGCTATC CCTCGCTGGA AGGTGAGAAG  360
GCATATAGAG AGACAACAGA CTTGGGCATT GAACCATTAA GGATTGGCAT CAAGAAACTT  420
GATGAAAATG CGATAGACAA TTATAAACCA ACGGAGATAG CTAGTTCTCT ATTGGTTGTT  480
ATTCAAATGG TGTCTGAAGC AGCTCGATTC ACCTTTATTG AGAACCAAAT TAGAAATAAC  540
TTTCAACAGA GAATTCGCCC GGCGAATAAT ACAATCAGCC TTGAGAATAA ATGGGGTAAA  600
CTCTCGTTCC AGATCCGGAC ATCAGGTGCA AATGGAATGT TTTCGGAGGC AGTTGAATTG  660
GAACGTGCAA ATGGCAAAAA ATACTATGTC ACCGCAGTTG ATCAAGTAAA ACCCAAAATA  720
GCACTCTTGA AGTTCGTCGA TAAAGATCCT AAAACGAGCC TTGCTGCTGA ATTGATAATC  780
CAGAACTATG AGTCATTAGT GGGCTTTGAT TAG                               813
```

( 2 ) INFORMATION FOR SEQ ID NO:247:

( i ) SEQUENCE CHARACTERISTICS:
        ( A ) LENGTH: 251 amino acids ( B ) TYPE: amino acid
( D ) TOPOLOGY: linear ( i i ) MOLECULE TYPE: protein ( x i ) SEQUENCE DESCRIPTION: SEQ ID NO:247:

| Gly | Leu | Asp | Thr | Val | Ser | Phe | Ser | Thr | Lys | Gly | Ala | Thr | Tyr | Ile | Thr |
|---|---|---|---|---|---|---|---|---|---|---|---|---|---|---|---|
| 1 | | | | 5 | | | | | 10 | | | | | 15 | |

| Tyr | Val | Asn | Phe | Leu | Asn | Glu | Leu | Arg | Val | Lys | Leu | Lys | Pro | Glu | Gly |
|---|---|---|---|---|---|---|---|---|---|---|---|---|---|---|---|
| | | | 20 | | | | | 25 | | | | | 30 | | |

| Asn | Ser | His | Gly | Ile | Pro | Leu | Leu | Arg | Lys | Lys | Cys | Asp | Asp | Pro | Gly |
|---|---|---|---|---|---|---|---|---|---|---|---|---|---|---|---|
| | | 35 | | | | | 40 | | | | | 45 | | | |

| Lys | Cys | Phe | Val | Leu | Val | Ala | Leu | Ser | Asn | Asp | Asn | Gly | Gln | Leu | Ala |
|---|---|---|---|---|---|---|---|---|---|---|---|---|---|---|---|
| | 50 | | | | | 55 | | | | | 60 | | | | |

| Glu | Ile | Ala | Ile | Asp | Val | Thr | Ser | Val | Tyr | Val | Val | Gly | Tyr | Gln | Val |
|---|---|---|---|---|---|---|---|---|---|---|---|---|---|---|---|
| 65 | | | | | 70 | | | | | 75 | | | | | 80 |

| Arg | Asn | Arg | Ser | Tyr | Phe | Phe | Lys | Asp | Ala | Pro | Asp | Ala | Ala | Tyr | Glu |
|---|---|---|---|---|---|---|---|---|---|---|---|---|---|---|---|
| | | | | 85 | | | | | 90 | | | | | 95 | |

| Gly | Leu | Phe | Lys | Asn | Thr | Ile | Lys | Thr | Arg | Leu | His | Phe | Gly | Gly | Ser |
|---|---|---|---|---|---|---|---|---|---|---|---|---|---|---|---|
| | | | 100 | | | | | 105 | | | | | 110 | | |

| Tyr | Pro | Ser | Leu | Glu | Gly | Glu | Lys | Ala | Tyr | Arg | Glu | Thr | Thr | Asp | Leu |
|---|---|---|---|---|---|---|---|---|---|---|---|---|---|---|---|
| | | 115 | | | | | 120 | | | | | 125 | | | |

| Gly | Ile | Glu | Pro | Leu | Arg | Ile | Gly | Ile | Lys | Lys | Leu | Asp | Glu | Asn | Ala |
|---|---|---|---|---|---|---|---|---|---|---|---|---|---|---|---|
| | 130 | | | | | 135 | | | | | 140 | | | | |

| Ile | Asp | Asn | Tyr | Lys | Pro | Thr | Glu | Ile | Ala | Ser | Ser | Leu | Leu | Val | Val |
|---|---|---|---|---|---|---|---|---|---|---|---|---|---|---|---|
| 145 | | | | | 150 | | | | | 155 | | | | | 160 |

| Ile | Gln | Met | Val | Ser | Glu | Ala | Ala | Arg | Phe | Thr | Phe | Ile | Glu | Asn | Gln |
|---|---|---|---|---|---|---|---|---|---|---|---|---|---|---|---|
| | | | | 165 | | | | | 170 | | | | | 175 | |

| Ile | Arg | Asn | Asn | Phe | Gln | Gln | Arg | Ile | Arg | Pro | Ala | Asn | Asn | Thr | Ile |
|---|---|---|---|---|---|---|---|---|---|---|---|---|---|---|---|
| | | | 180 | | | | | 185 | | | | | 190 | | |

| Ser | Leu | Glu | Asn | Lys | Trp | Gly | Lys | Leu | Ser | Phe | Gln | Ile | Arg | Thr | Ser |
|---|---|---|---|---|---|---|---|---|---|---|---|---|---|---|---|
| | | 195 | | | | | 200 | | | | | 205 | | | |

| Gly | Ala | Asn | Gly | Met | Phe | Ser | Glu | Ala | Val | Glu | Leu | Glu | Arg | Ala | Asn |
|---|---|---|---|---|---|---|---|---|---|---|---|---|---|---|---|
| | 210 | | | | | 215 | | | | | 220 | | | | |

| Gly | Lys | Lys | Tyr | Tyr | Val | Thr | Ala | Val | Asp | Gln | Val | Lys | Pro | Lys | Ile |
|---|---|---|---|---|---|---|---|---|---|---|---|---|---|---|---|
| 225 | | | | | 230 | | | | | 235 | | | | | 240 |

| Ala | Leu | Leu | Lys | Phe | Val | Asp | Lys | Asp | Pro | Lys |
|---|---|---|---|---|---|---|---|---|---|---|
| | | | | 245 | | | | | 250 | |

( 2 ) INFORMATION FOR SEQ ID NO:248:

( i ) SEQUENCE CHARACTERISTICS:
        ( A ) LENGTH: 557 base pairs
        ( B ) TYPE: nucleic acid
        ( C ) STRANDEDNESS: single
        ( D ) TOPOLOGY: linear ( i i ) MOLECULE TYPE: protein ( v i ) ORIGINAL SOURCE:
        ( A ) ORGANISM:

( i x ) FEATURE:
        ( A ) NAME/KEY: CDS
        ( B ) LOCATION: 66..548

( i x ) FEATURE:
        ( A ) NAME/KEY: misc_feature
        ( B ) LOCATION:residues 1-65
        ( D ) OTHER INFORMATION: /label=EcoRI
                / note="residues 1-65 comprise EcoRI site to begining of
            pel B."

( i x ) FEATURE:
    ( A ) NAME/KEY: misc_feature
    ( B ) LOCATION:AA 1-22
    ( D ) OTHER INFORMATION: /label=pel B
        / note="pel B is the leader sequence from the pectate lyase gene of Erwinia carotovora."

( i x ) FEATURE:
    ( A ) NAME/KEY: misc_feature
    ( B ) LOCATION:AA 23-161
    ( D ) OTHER INFORMATION: /label="Bone D"
        / note="Bone D is the subunit of human osteogenic protein (see, U.S. Patent No. 5,284,756 e.g., Fig. 6, Example 9, Seq ID NOs: 1 and 2."

( i x ) FEATURE:
    ( A ) NAME/KEY: misc_feature
    ( B ) LOCATION:residues 549-557
    ( D ) OTHER INFORMATION: /label=XhoI
        / note="residues 549-557 comprise stop codon and XhoI site."

( x i ) SEQUENCE DESCRIPTION: SEQ ID NO:248:

```
GAATTCCTGC AGGTCTATGG AACGATAAAT GCCCATGAAA ATTCTATTTC AAGGAGACAG                    60

TCATA ATG AAA TAC CTA TTG CCT ACG GCA GCC GCT GGA TTG TTA TTA                       107
      Met Lys Tyr Leu Leu Pro Thr Ala Ala Ala Gly Leu Leu Leu
       1               5                      10

CTC GCT GCC CAA CCA GCG ATG GCG TCC ACG GGG AGC AAA CAG CGC AGC                     155
Leu Ala Ala Gln Pro Ala Met Ala Ser Thr Gly Ser Lys Gln Arg Ser
 15              20                  25                      30

CAG AAC CGC TCC AAG ACG CCC AAG AAC CAG GAA GCC CTG CGG ATG GCC                     203
Gln Asn Arg Ser Lys Thr Pro Lys Asn Gln Glu Ala Leu Arg Met Ala
                 35              40                      45

AAC GTG GCA GAG AAC AGC AGC AGC GAC CAG AGG CAG GCC TGT AAG AAG                     251
Asn Val Ala Glu Asn Ser Ser Ser Asp Gln Arg Gln Ala Cys Lys Lys
             50                  55                  60

CAC GAG CTG TAT GTC AGC TTC CGA GAC CTG GGC TGG CAG GAC TGG ATC                     299
His Glu Leu Tyr Val Ser Phe Arg Asp Leu Gly Trp Gln Asp Trp Ile
         65                  70                  75

ATC GCG CCT GAA GGC TAC GCC GCC TAC TAC TGT GAG GGG GAG TGT GCC                     347
Ile Ala Pro Glu Gly Tyr Ala Ala Tyr Tyr Cys Glu Gly Glu Cys Ala
     80                  85                  90

TTC CCT CTG AAC TCC TAC ATG AAC GCC ACC AAC CAC GCC ATC GTG CAG                     395
Phe Pro Leu Asn Ser Tyr Met Asn Ala Thr Asn His Ala Ile Val Gln
 95                 100                 105                 110

ACG CTG GTC CAC TTC ATC AAC CCG GAA ACG GTG CCC AAG CCC TGC TGT                     443
Thr Leu Val His Phe Ile Asn Pro Glu Thr Val Pro Lys Pro Cys Cys
             115                 120                 125

GCG CCC ACG CAG CTC AAT GCC ATC TCC GTC CTC TAC TTC GAT GAC AGC                     491
Ala Pro Thr Gln Leu Asn Ala Ile Ser Val Leu Tyr Phe Asp Asp Ser
         130                 135                 140

TCC AAC GTC ATC CTG AAG AAA TAC AGA AAC ATG GTG GTC CGG GCC TGT                     539
Ser Asn Val Ile Leu Lys Lys Tyr Arg Asn Met Val Val Arg Ala Cys
     145                 150                 155

GGC TGC CAC TAGCTCGAG                                                               557
Gly Cys His
 160
```

( 2 ) INFORMATION FOR SEQ ID NO:249:

( i ) SEQUENCE CHARACTERISTICS:
        ( A ) LENGTH: 161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:249:

| Met | Lys | Tyr | Leu | Leu | Pro | Thr | Ala | Ala | Ala | Gly | Leu | Leu | Leu | Leu | Ala |
|---|---|---|---|---|---|---|---|---|---|---|---|---|---|---|---|
| 1 | | | | 5 | | | | | 10 | | | | | 15 | |

| Ala | Gln | Pro | Ala | Met | Ala | Ser | Thr | Gly | Ser | Lys | Gln | Arg | Ser | Gln | Asn |
|---|---|---|---|---|---|---|---|---|---|---|---|---|---|---|---|
| | | | 20 | | | | | 25 | | | | | 30 | | |

| Arg | Ser | Lys | Thr | Pro | Lys | Asn | Gln | Glu | Ala | Leu | Arg | Met | Ala | Asn | Val |
|---|---|---|---|---|---|---|---|---|---|---|---|---|---|---|---|
| | | 35 | | | | | 40 | | | | | 45 | | | |

| Ala | Glu | Asn | Ser | Ser | Ser | Asp | Gln | Arg | Gln | Ala | Cys | Lys | Lys | His | Glu |
|---|---|---|---|---|---|---|---|---|---|---|---|---|---|---|---|
| | 50 | | | | | 55 | | | | | 60 | | | | |

| Leu | Tyr | Val | Ser | Phe | Arg | Asp | Leu | Gly | Trp | Gln | Asp | Trp | Ile | Ile | Ala |
|---|---|---|---|---|---|---|---|---|---|---|---|---|---|---|---|
| 65 | | | | | 70 | | | | | 75 | | | | | 80 |

| Pro | Glu | Gly | Tyr | Ala | Ala | Tyr | Tyr | Cys | Glu | Gly | Glu | Cys | Ala | Phe | Pro |
|---|---|---|---|---|---|---|---|---|---|---|---|---|---|---|---|
| | | | | 85 | | | | | 90 | | | | | 95 | |

| Leu | Asn | Ser | Tyr | Met | Asn | Ala | Thr | Asn | His | Ala | Ile | Val | Gln | Thr | Leu |
|---|---|---|---|---|---|---|---|---|---|---|---|---|---|---|---|
| | | | 100 | | | | | 105 | | | | | 110 | | |

| Val | His | Phe | Ile | Asn | Pro | Glu | Thr | Val | Pro | Lys | Pro | Cys | Cys | Ala | Pro |
|---|---|---|---|---|---|---|---|---|---|---|---|---|---|---|---|
| | | 115 | | | | | 120 | | | | | 125 | | | |

| Thr | Gln | Leu | Asn | Ala | Ile | Ser | Val | Leu | Tyr | Phe | Asp | Asp | Ser | Ser | Asn |
|---|---|---|---|---|---|---|---|---|---|---|---|---|---|---|---|
| | 130 | | | | | 135 | | | | | 140 | | | | |

| Val | Ile | Leu | Lys | Lys | Tyr | Arg | Asn | Met | Val | Val | Arg | Ala | Cys | Gly | Cys |
|---|---|---|---|---|---|---|---|---|---|---|---|---|---|---|---|
| 145 | | | | | 150 | | | | | 155 | | | | | 160 |

His ( 2 ) INFORMATION FOR SEQ ID NO:250:

( i ) SEQUENCE CHARACTERISTICS:
        ( A ) LENGTH: 1072 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 66..1061

( i x ) FEATURE:
        ( A ) NAME/KEY: misc_feature
        ( B ) LOCATION:residues 1-65
        ( D ) OTHER INFORMATION: /label=EcoRI
            / note="residues 1-65 comprise EcoRI site to beginning of
            pel B."

( i x ) FEATURE:
        ( A ) NAME/KEY: misc_feature
        ( B ) LOCATION:AA 1-22
        ( D ) OTHER INFORMATION: /label=pel B
            / note="pel B is the leader sequence from the pectate
            lyase gene of Erwinia caratovora."

( i x ) FEATURE:
        ( A ) NAME/KEY: misc_feature
        ( B ) LOCATION:AA 23-273
        ( D ) OTHER INFORMATION: /label="gelonin"
/ note="gelonin (see U.S. Patent No. 5,416,202)."

( i x ) FEATURE:
( A ) NAME/KEY: misc_feature
( B ) LOCATION:AA 274-276
( D ) OTHER INFORMATION: /label=EagI
/ note="EagI cloning site."

( i x ) FEATURE:
( A ) NAME/KEY: misc_feature
( B ) LOCATION:AA 277-296
( D ) OTHER INFORMATION: /label=SLT linker
/ note="SLT from shiga-like-toxin gene."

( i x ) FEATURE:
    ( A ) NAME/KEY: misc_feature
    ( B ) LOCATION:AA 297-298
    ( D ) OTHER INFORMATION: /label=FspI/ScaI
        / note="FspI and ScaI cloning sites."

( i x ) FEATURE:
    ( A ) NAME/KEY: misc_feature
    ( B ) LOCATION:AA 299-302
    ( D ) OTHER INFORMATION: /label=cleavage linker
        / note="Ala-Leu-Asp-Pro linking sequence with Asp-Pro cleavage site."

( i x ) FEATURE:
    ( A ) NAME/KEY: misc_feature
    ( B ) LOCATION:AA 303-332
    ( D ) OTHER INFORMATION: /label=peptide sequence
        / note="BPI-derived peptide."

( i x ) FEATURE:
    ( A ) NAME/KEY: misc_feature
    ( B ) LOCATION:residues 1062- 1072
    ( D ) OTHER INFORMATION: /label=XhoI
        / note="residues 1062-1072 comprise stop codon and XhoI site."

( x i ) SEQUENCE DESCRIPTION: SEQ ID NO:250:

```
GAATTCCTGC AGGTCTATGG AACGATAAAT GCCCATGAAA ATTCTATTTC AAGGAGACAG        60

TCATA ATG AAA TAC CTA TTG CCT ACG GCA GCC GCT GGA TTG TTA TTA          107
      Met Lys Tyr Leu Leu Pro Thr Ala Ala Ala Gly Leu Leu Leu
       1           5                   10

CTC GCT GCC CAA CCA GCG ATG GCG GGC CTG GAC ACC GTG AGC TTT AGC        155
Leu Ala Ala Gln Pro Ala Met Ala Gly Leu Asp Thr Val Ser Phe Ser
 15              20                  25                      30

ACT AAA GGT GCC ACT TAT ATT ACC TAC GTG AAT TTC TTG AAT GAG CTA        203
Thr Lys Gly Ala Thr Tyr Ile Thr Tyr Val Asn Phe Leu Asn Glu Leu
                     35                  40                  45

CGA GTT AAA TTG AAA CCC GAA GGT AAC AGC CAT GGA ATC CCA TTG CTG        251
Arg Val Lys Leu Lys Pro Glu Gly Asn Ser His Gly Ile Pro Leu Leu
             50                  55                  60

CGC AAA AAA TGT GAT GAT CCT GGA AAG TGT TTC GTT TTG GTA GCG CTT        299
Arg Lys Lys Cys Asp Asp Pro Gly Lys Cys Phe Val Leu Val Ala Leu
         65                  70                  75

TCA AAT GAC AAT GGA CAG TTG GCG GAA ATA GCT ATA GAT GTT ACA AGT        347
Ser Asn Asp Asn Gly Gln Leu Ala Glu Ile Ala Ile Asp Val Thr Ser
     80                  85                  90

GTT TAT GTG GTG GGC TAT CAA GTA AGA AAC AGA TCT TAC TTC TTT AAA        395
Val Tyr Val Val Gly Tyr Gln Val Arg Asn Arg Ser Tyr Phe Phe Lys
 95              100                 105                     110

GAT GCT CCA GAT GCT GCT TAC GAA GGC CTC TTC AAA AAC ACA ATT AAA        443
Asp Ala Pro Asp Ala Ala Tyr Glu Gly Leu Phe Lys Asn Thr Ile Lys
                 115                 120                 125

ACA AGA CTT CAT TTT GGC GGC ACG TAT CCC TCG CTG GAA GGT GAG AAG        491
Thr Arg Leu His Phe Gly Gly Thr Tyr Pro Ser Leu Glu Gly Glu Lys
             130                 135                 140

GCA TAT AGA GAG ACA ACA GAC TTG GGC ATT GAA CCA TTA AGG ATT GGC        539
Ala Tyr Arg Glu Thr Thr Asp Leu Gly Ile Glu Pro Leu Arg Ile Gly
         145                 150                 155

ATC AAG AAA CTT GAT GAA AAT GCG ATA GAC AAT TAT AAA CCA ACG GAG        587
Ile Lys Lys Leu Asp Glu Asn Ala Ile Asp Asn Tyr Lys Pro Thr Glu
     160                 165                 170

ATA GCT AGT TCT CTA TTG GTT GTT ATT CAA ATG GTG TCT GAA GCA GCT        635
Ile Ala Ser Ser Leu Leu Val Val Ile Gln Met Val Ser Glu Ala Ala
175              180                 185                     190

CGA TTC ACC TTT ATT GAG AAC CAA ATT AGA AAT AAC TTT CAA CAG AGA        683
```

| | | | | | | | | | | | | | | | |
|---|---|---|---|---|---|---|---|---|---|---|---|---|---|---|---|
| Arg | Phe | Thr | Phe | Ile<br>195 | Glu | Asn | Gln | Ile<br>200 | Arg | Asn | Asn | Phe | Gln<br>205 | Gln | Arg |

| ATT | CGC | CCG | GCG | AAT | AAT | ACA | ATC | AGC | CTT | GAG | AAT | AAA | TGG | GGT | AAA | 731 |
|---|---|---|---|---|---|---|---|---|---|---|---|---|---|---|---|---|
| Ile | Arg | Pro | Ala<br>210 | Asn | Asn | Thr | Ile | Ser<br>215 | Leu | Glu | Asn | Lys | Trp<br>220 | Gly | Lys | |

| CTC | TCG | TTC | CAG | ATC | CGG | ACA | TCA | GGT | GCA | AAT | GGA | ATG | TTT | TCG | GAG | 779 |
|---|---|---|---|---|---|---|---|---|---|---|---|---|---|---|---|---|
| Leu | Ser | Phe<br>225 | Gln | Ile | Arg | Thr | Ser<br>230 | Gly | Ala | Asn | Gly | Met<br>235 | Phe | Ser | Glu | |

| GCA | GTT | GAA | TTG | GAA | CGT | GCA | AAT | GGC | AAA | AAA | TAC | TAT | GTC | ACC | GCA | 827 |
|---|---|---|---|---|---|---|---|---|---|---|---|---|---|---|---|---|
| Ala | Val<br>240 | Glu | Leu | Glu | Arg | Ala<br>245 | Asn | Gly | Lys | Lys | Tyr<br>250 | Tyr | Val | Thr | Ala | |

| GTT | GAT | CAA | GTA | AAA | CCC | AAA | ATA | GCA | CTC | TTG | AAG | TTC | GTC | GAT | AAA | 875 |
|---|---|---|---|---|---|---|---|---|---|---|---|---|---|---|---|---|
| Val<br>255 | Asp | Gln | Val | Lys | Pro<br>260 | Lys | Ile | Ala | Leu | Leu<br>265 | Lys | Phe | Val | Asp | Lys<br>270 | |

| GAT | CCT | AAA | TCG | GCC | GCA | TGT | CAT | CAT | CAT | GCA | TCG | CGA | GTT | GCC | AGA | 923 |
|---|---|---|---|---|---|---|---|---|---|---|---|---|---|---|---|---|
| Asp | Pro | Lys | Ser | Ala<br>275 | Ala | Cys | His | His | His<br>280 | Ala | Ser | Arg | Val | Ala<br>285 | Arg | |

| ATG | GCA | TCT | GAT | GAG | TTT | CCT | TCT | ATG | TGC | GCA | ATG | GCA | TTG | GAT | CCG | 971 |
|---|---|---|---|---|---|---|---|---|---|---|---|---|---|---|---|---|
| Met | Ala | Ser | Asp<br>290 | Glu | Phe | Pro | Ser | Met<br>295 | Cys | Ala | Met | Ala | Leu<br>300 | Asp | Pro | |

| ATC | AAA | ATC | TCG | GGT | AAA | TGG | AAG | GCC | CAG | AAA | CGC | TTT | CTG | AAA | AAG | 1019 |
|---|---|---|---|---|---|---|---|---|---|---|---|---|---|---|---|---|
| Ile | Lys | Ile<br>305 | Ser | Gly | Lys | Trp | Lys<br>310 | Ala | Gln | Lys | Arg | Phe<br>315 | Leu | Lys | Lys | |

| TCG | AAA | GTG | GGT | TGG | CTG | ATC | CAG | CTG | TTT | CAT | AAA | AAG | ATT | | | 1061 |
|---|---|---|---|---|---|---|---|---|---|---|---|---|---|---|---|---|
| Ser | Lys<br>320 | Val | Gly | Trp | Leu | Ile<br>325 | Gln | Leu | Phe | His | Lys<br>330 | Lys | Ile | | | |

| TAAAGCTCGA G | | | | | | | | | | | | | | | | 1072 |
|---|---|---|---|---|---|---|---|---|---|---|---|---|---|---|---|---|

( 2 ) INFORMATION FOR SEQ ID NO:251:

( i ) SEQUENCE CHARACTERISTICS:
  ( A ) LENGTH: 332 amino acids
  ( B ) TYPE: amino acid
  ( D ) TOPOLOGY: linear ( i i ) MOLECULE TYPE: protein ( x i ) SEQUENCE DESCRIPTION: SEQ ID NO:251:

| | | | | | | | | | | | | | | | |
|---|---|---|---|---|---|---|---|---|---|---|---|---|---|---|---|
| Met<br>1 | Lys | Tyr | Leu | Leu<br>5 | Pro | Thr | Ala | Ala | Ala<br>10 | Gly | Leu | Leu | Leu | Leu<br>15 | Ala |
| Ala | Gln | Pro | Ala<br>20 | Met | Ala | Gly | Leu | Asp<br>25 | Thr | Val | Ser | Phe | Ser<br>30 | Thr | Lys |
| Gly | Ala | Thr<br>35 | Tyr | Ile | Thr | Tyr | Val<br>40 | Asn | Phe | Leu | Asn | Glu<br>45 | Leu | Arg | Val |
| Lys | Leu<br>50 | Lys | Pro | Glu | Gly | Asn<br>55 | Ser | His | Gly | Ile | Pro<br>60 | Leu | Leu | Arg | Lys |
| Lys<br>65 | Cys | Asp | Asp | Pro | Gly<br>70 | Lys | Cys | Phe | Val | Leu<br>75 | Val | Ala | Leu | Ser | Asn<br>80 |
| Asp | Asn | Gly | Gln | Leu<br>85 | Ala | Glu | Ile | Ala<br>90 | Ile | Asp | Val | Thr | Ser | Val<br>95 | Tyr |
| Val | Val | Gly | Tyr<br>100 | Gln | Val | Arg | Asn | Arg<br>105 | Ser | Tyr | Phe | Phe | Lys<br>110 | Asp | Ala |
| Pro | Asp | Ala<br>115 | Ala | Tyr | Glu | Gly | Leu<br>120 | Phe | Lys | Asn | Thr | Ile<br>125 | Lys | Thr | Arg |
| Leu | His<br>130 | Phe | Gly | Gly | Thr | Tyr<br>135 | Pro | Ser | Leu | Glu | Gly<br>140 | Glu | Lys | Ala | Tyr |
| Arg<br>145 | Glu | Thr | Thr | Asp | Leu<br>150 | Gly | Ile | Glu | Pro | Leu<br>155 | Arg | Ile | Gly | Ile | Lys<br>160 |
| Lys | Leu | Asp | Glu | Asn | Ala | Ile | Asp | Asn | Tyr | Lys | Pro | Thr | Glu | Ile | Ala |

|     |     |     |     |     |     |     | 165 |     |     |     | 170 |     |     |     | 175 |
|-----|-----|-----|-----|-----|-----|-----|-----|-----|-----|-----|-----|-----|-----|-----|-----|

Ser Ser Leu Leu Val Val Ile Gln Met Val Ser Glu Ala Ala Arg Phe
            180             185                 190

Thr Phe Ile Glu Asn Gln Ile Arg Asn Asn Phe Gln Gln Arg Ile Arg
        195                 200                 205

Pro Ala Asn Asn Thr Ile Ser Leu Glu Asn Lys Trp Gly Lys Leu Ser
    210                 215                 220

Phe Gln Ile Arg Thr Ser Gly Ala Asn Gly Met Phe Ser Glu Ala Val
225                     230                 235                     240

Glu Leu Glu Arg Ala Asn Gly Lys Lys Tyr Tyr Val Thr Ala Val Asp
                245                 250                     255

Gln Val Lys Pro Lys Ile Ala Leu Leu Lys Phe Val Asp Lys Asp Pro
            260                 265                 270

Lys Ser Ala Ala Cys His His His Ala Ser Arg Val Ala Arg Met Ala
            275                 280                 285

Ser Asp Glu Phe Pro Ser Met Cys Ala Met Ala Leu Asp Pro Ile Lys
    290                 295                 300

Ile Ser Gly Lys Trp Lys Ala Gln Lys Arg Phe Leu Lys Lys Ser Lys
305                 310                 315                     320

Val Gly Trp Leu Ile Gln Leu Phe His Lys Lys Ile
                325                 330

( 2 ) INFORMATION FOR SEQ ID NO:252:

( i ) SEQUENCE CHARACTERISTICS:
        ( A ) LENGTH: 1003 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 66..992

( i x ) FEATURE:
        ( A ) NAME/KEY: misc_feature
        ( B ) LOCATION:residues 1-65
        ( D ) OTHER INFORMATION: /label=EcoRI
            / note="residues 1-65 comprise EcoRI site to beginning of
            pel B."

( i x ) FEATURE:
        ( A ) NAME/KEY: misc_feature
        ( B ) LOCATION:AA 1-22
        ( D ) OTHER INFORMATION: /label=pel B
            / note="pel B is the leader sequence from the pectate
            lyase gene of Erwinia caratovora."

( i x ) FEATURE:
        ( A ) NAME/KEY: misc_feature
        ( B ) LOCATION:AA 23-273
        ( D ) OTHER INFORMATION: /label="gelonin"
            / note="gelonin (see U.S. Patent No. 5,416,202)."

( i x ) FEATURE:
        ( A ) NAME/KEY: misc_feature
        ( B ) LOCATION:AA 274-275
        ( D ) OTHER INFORMATION: /label=EagI
            / note="EagI cloning site."

( i x ) FEATURE:
        ( A ) NAME/KEY: misc_feature
        ( B ) LOCATION:AA 276-279
        ( D ) OTHER INFORMATION: /label=cleavage linker
            / note="Ala-Leu-Asp-Pro linking sequence with Asp-Pro
            cleavage site."

( i x ) FEATURE:
    ( A ) NAME/KEY: misc_feature
    ( B ) LOCATION:AA 280-309
    ( D ) OTHER INFORMATION: /label=peptide sequence
        / note="BPI-derived peptide."

( i x ) FEATURE:
    ( A ) NAME/KEY: misc_feature
    ( B ) LOCATION:residues 993-1011
    ( D ) OTHER INFORMATION: /label=XhoI
        / note="residues 993-1003 comprise stop codon and XhoI site."

( x i ) SEQUENCE DESCRIPTION: SEQ ID NO:252:

```
GAATTCCTGC  AGGTCTATGG  AACGATAAAT  GCCCATGAAA  ATTCTATTTC  AAGGAGACAG                60

TCATA ATG AAA TAC CTA TTG CCT ACG GCA GCC GCT GGA TTG TTA TTA                         107
      Met Lys Tyr Leu Leu Pro Thr Ala Ala Ala Gly Leu Leu Leu
       1               5                          10

CTC GCT GCC CAA CCA GCG ATG GCG GGC CTG GAC ACC GTG AGC TTT AGC                       155
Leu Ala Ala Gln Pro Ala Met Ala Gly Leu Asp Thr Val Ser Phe Ser
 15              20                  25                      30

ACT AAA GGT GCC ACT TAT ATT ACC TAC GTG AAT TTC TTG AAT GAG CTA                       203
Thr Lys Gly Ala Thr Tyr Ile Thr Tyr Val Asn Phe Leu Asn Glu Leu
                 35                  40                      45

CGA GTT AAA TTG AAA CCC GAA GGT AAC AGC CAT GGA ATC CCA TTG CTG                       251
Arg Val Lys Leu Lys Pro Glu Gly Asn Ser His Gly Ile Pro Leu Leu
             50                  55                  60

CGC AAA AAA TGT GAT GAT CCT GGA AAG TGT TTC GTT TTG GTA GCG CTT                       299
Arg Lys Lys Cys Asp Asp Pro Gly Lys Cys Phe Val Leu Val Ala Leu
             65                  70                  75

TCA AAT GAC AAT GGA CAG TTG GCG GAA ATA GCT ATA GAT GTT ACA AGT                       347
Ser Asn Asp Asn Gly Gln Leu Ala Glu Ile Ala Ile Asp Val Thr Ser
         80              85                  90

GTT TAT GTG GTG GGC TAT CAA GTA AGA AAC AGA TCT TAC TTC TTT AAA                       395
Val Tyr Val Val Gly Tyr Gln Val Arg Asn Arg Ser Tyr Phe Phe Lys
 95              100                 105                     110

GAT GCT CCA GAT GCT GCT TAC GAA GGC CTC TTC AAA AAC ACA ATT AAA                       443
Asp Ala Pro Asp Ala Ala Tyr Glu Gly Leu Phe Lys Asn Thr Ile Lys
                 115                 120                 125

ACA AGA CTT CAT TTT GGC GGC ACG TAT CCC TCG CTG GAA GGT GAG AAG                       491
Thr Arg Leu His Phe Gly Gly Thr Tyr Pro Ser Leu Glu Gly Glu Lys
             130                 135                 140

GCA TAT AGA GAG ACA ACA GAC TTG GGC ATT GAA CCA TTA AGG ATT GGC                       539
Ala Tyr Arg Glu Thr Thr Asp Leu Gly Ile Glu Pro Leu Arg Ile Gly
         145                 150                 155

ATC AAG AAA CTT GAT GAA AAT GCG ATA GAC AAT TAT AAA CCA ACG GAG                       587
Ile Lys Lys Leu Asp Glu Asn Ala Ile Asp Asn Tyr Lys Pro Thr Glu
     160                 165                 170

ATA GCT AGT TCT CTA TTG GTT GTT ATT CAA ATG GTG TCT GAA GCA GCT                       635
Ile Ala Ser Ser Leu Leu Val Val Ile Gln Met Val Ser Glu Ala Ala
175                 180                 185                 190

CGA TTC ACC TTT ATT GAG AAC CAA ATT AGA AAT AAC TTT CAA CAG AGA                       683
Arg Phe Thr Phe Ile Glu Asn Gln Ile Arg Asn Asn Phe Gln Gln Arg
             195                 200                 205

ATT CGC CCG GCG AAT AAT ACA ATC AGC CTT GAG AAT AAA TGG GGT AAA                       731
Ile Arg Pro Ala Asn Asn Thr Ile Ser Leu Glu Asn Lys Trp Gly Lys
             210                 215                 220

CTC TCG TTC CAG ATC CGG ACA TCA GGT GCA AAT GGA ATG TTT TCG GAG                       779
Leu Ser Phe Gln Ile Arg Thr Ser Gly Ala Asn Gly Met Phe Ser Glu
         225                 230                 235

GCA GTT GAA TTG GAA CGT GCA AAT GGC AAA AAA TAC TAT GTC ACC GCA                       827
Ala Val Glu Leu Glu Arg Ala Asn Gly Lys Lys Tyr Tyr Val Thr Ala
240                 245                 250
```

```
GTT  GAT  CAA  GTA  AAA  CCC  AAA  ATA  GCA  CTC  TTG  AAG  TTC  GTC  GAT  AAA          875
Val  Asp  Gln  Val  Lys  Pro  Lys  Ile  Ala  Leu  Leu  Lys  Phe  Val  Asp  Lys
255                      260                      265                      270

GAT  CCT  AAA  TCG  GCC  GCA  TTG  GAT  CCG  ATC  AAA  ATC  TCG  GGT  AAA  TGG          923
Asp  Pro  Lys  Ser  Ala  Ala  Leu  Asp  Pro  Ile  Lys  Ile  Ser  Gly  Lys  Trp
                         275                      280                      285

AAG  GCC  CAG  AAA  CGC  TTT  CTG  AAA  AAG  TCG  AAA  GTG  GGT  TGG  CTG  ATC          971
Lys  Ala  Gln  Lys  Arg  Phe  Leu  Lys  Lys  Ser  Lys  Val  Gly  Trp  Leu  Ile
               290                      295                      300

CAG  CTG  TTT  CAT  AAA  AAG  ATT  TAAAGCTCGA G                                         1003
Gln  Leu  Phe  His  Lys  Lys  Ile
               305
```

( 2 ) INFORMATION FOR SEQ ID NO:253:

( i ) SEQUENCE CHARACTERISTICS:
        ( A ) LENGTH: 309 amino acids
        ( B ) TYPE: amino acid
        ( D ) TOPOLOGY: linear ( i i ) MOLECULE TYPE: protein ( x i ) SEQUENCE DESCRIPTION: SEQ ID NO:253:

```
Met  Lys  Tyr  Leu  Leu  Pro  Thr  Ala  Ala  Ala  Gly  Leu  Leu  Leu  Leu  Ala
 1                   5                        10                       15

Ala  Gln  Pro  Ala  Met  Ala  Gly  Leu  Asp  Thr  Val  Ser  Phe  Ser  Thr  Lys
               20                   25                       30

Gly  Ala  Thr  Tyr  Ile  Thr  Tyr  Val  Asn  Phe  Leu  Asn  Glu  Leu  Arg  Val
               35                   40                       45

Lys  Leu  Lys  Pro  Glu  Gly  Asn  Ser  His  Gly  Ile  Pro  Leu  Leu  Arg  Lys
      50                   55                        60

Lys  Cys  Asp  Asp  Pro  Gly  Lys  Cys  Phe  Val  Leu  Val  Ala  Leu  Ser  Asn
 65                       70                        75                       80

Asp  Asn  Gly  Gln  Leu  Ala  Glu  Ile  Ala  Ile  Asp  Val  Thr  Ser  Val  Tyr
                    85                        90                       95

Val  Val  Gly  Tyr  Gln  Val  Arg  Asn  Arg  Ser  Tyr  Phe  Phe  Lys  Asp  Ala
               100                  105                       110

Pro  Asp  Ala  Ala  Tyr  Glu  Gly  Leu  Phe  Lys  Asn  Thr  Ile  Lys  Thr  Arg
          115                       120                      125

Leu  His  Phe  Gly  Gly  Thr  Tyr  Pro  Ser  Leu  Glu  Gly  Glu  Lys  Ala  Tyr
      130                       135                      140

Arg  Glu  Thr  Thr  Asp  Leu  Gly  Ile  Glu  Pro  Leu  Arg  Ile  Gly  Ile  Lys
145                       150                      155                      160

Lys  Leu  Asp  Glu  Asn  Ala  Ile  Asp  Asn  Tyr  Lys  Pro  Thr  Glu  Ile  Ala
                    165                       170                      175

Ser  Ser  Leu  Leu  Val  Val  Ile  Gln  Met  Val  Ser  Glu  Ala  Ala  Arg  Phe
               180                       185                      190

Thr  Phe  Ile  Glu  Asn  Gln  Ile  Arg  Asn  Asn  Phe  Gln  Gln  Arg  Ile  Arg
          195                       200                      205

Pro  Ala  Asn  Asn  Thr  Ile  Ser  Leu  Glu  Asn  Lys  Trp  Gly  Lys  Leu  Ser
     210                       215                      220

Phe  Gln  Ile  Arg  Thr  Ser  Gly  Ala  Asn  Gly  Met  Phe  Ser  Glu  Ala  Val
225                       230                      235                      240

Glu  Leu  Glu  Arg  Ala  Asn  Gly  Lys  Lys  Tyr  Tyr  Val  Thr  Ala  Val  Asp
               245                      250                       255

Gln  Val  Lys  Pro  Lys  Ile  Ala  Leu  Leu  Lys  Phe  Val  Asp  Lys  Asp  Pro
               260                      265                       270
```

| Lys | Ser | Ala | Ala | Leu | Asp | Pro | Ile | Lys | Ile | Ser | Gly | Lys | Trp | Lys | Ala |
| | | 275 | | | | 280 | | | | | | 285 | | | |

| Gln | Lys | Arg | Phe | Leu | Lys | Lys | Ser | Lys | Val | Gly | Trp | Leu | Ile | Gln | Leu |
| | 290 | | | | | 295 | | | | | 300 | | | | |

| Phe | His | Lys | Lys | Ile |
| 305 | | | | |

( 2 ) INFORMATION FOR SEQ ID NO:254:

( i ) SEQUENCE CHARACTERISTICS:
        ( A ) LENGTH: 658 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 66..647

( i x ) FEATURE:
        ( A ) NAME/KEY: misc_feature
        ( B ) LOCATION:residues 1-65
        ( D ) OTHER INFORMATION: /label=EcoRI
            / note="residues 1-65 comprise EcoRI site to beginning of
            pel B."

( i x ) FEATURE:
        ( A ) NAME/KEY: misc_feature
        ( B ) LOCATION:AA 1-22
        ( D ) OTHER INFORMATION: /label=pel B
            / note="pel B is the leader sequence from the pectate
            lyase gene of Erwinia caratovora."

( i x ) FEATURE:
        ( A ) NAME/KEY: misc_feature
        ( B ) LOCATION:AA 23-161
        ( D ) OTHER INFORMATION: /label="Bone D"
            / note="Bone D is the subunit of human osteogenic protein
            (see, U.S. Patent No. 5,284,756 e.g., Fig. 6, Example 9,
            Seq ID NOs: 1 and 2."

( i x ) FEATURE:
        ( A ) NAME/KEY: misc_feature
        ( B ) LOCATION:AA 162-165
        ( D ) OTHER INFORMATION: /label=cleavage linker
            / note="Ala-Leu-Asp-Pro linking sequence with Asp-Pro
            cleavage site."

( i x ) FEATURE:
        ( A ) NAME/KEY: misc_feature
        ( B ) LOCATION:AA 166-194
        ( D ) OTHER INFORMATION: /label=peptide sequence
            / note="BPI-derived peptide."

( i x ) FEATURE:
        ( A ) NAME/KEY: misc_feature
        ( B ) LOCATION:residues 648-658
        ( D ) OTHER INFORMATION: /label=XhoI
            / note="residues 648-658 comprise stop codon and XhoI
            site."

( x i ) SEQUENCE DESCRIPTION: SEQ ID NO:254:

```
GAATTCCTGC AGGTCTATGG AACGATAAAT GCCCATGAAA ATTCTATTTC AAGGAGACAG        60

TCATA ATG AAA TAC CTA TTG CCT ACG GCA GCC GCT GGA TTG TTA TTA          107
      Met Lys Tyr Leu Leu Pro Thr Ala Ala Ala Gly Leu Leu Leu
        1               5                   10

CTC GCT GCC CAA CCA GCG ATG GCG TCC ACG GGG AGC AAA CAG CGC AGC        155
Leu Ala Ala Gln Pro Ala Met Ala Ser Thr Gly Ser Lys Gln Arg Ser
 15              20                  25                      30

CAG AAC CGC TCC AAG ACG CCC AAG AAC CAG GAA GCC CTG CGG ATG GCC       203
Gln Asn Arg Ser Lys Thr Pro Lys Asn Gln Glu Ala Leu Arg Met Ala
```

|  |  |  |  |  | 35 |  |  |  |  | 40 |  |  |  |  | 45 |  |  |
|---|---|---|---|---|---|---|---|---|---|---|---|---|---|---|---|---|---|
| AAC | GTG | GCA | GAG | AAC | AGC | AGC | AGC | GAC | CAG | AGG | CAG | GCC | TGT | AAG | AAG | | 251 |
| Asn | Val | Ala | Glu | Asn | Ser | Ser | Ser | Asp | Gln | Arg | Gln | Ala | Cys | Lys | Lys | | |
|  |  |  | 50 |  |  |  |  | 55 |  |  |  | 60 |  |  |  | | |
| CAC | GAG | CTG | TAT | GTC | AGC | TTC | CGA | GAC | CTG | GGC | TGG | CAG | GAC | TGG | ATC | | 299 |
| His | Glu | Leu | Tyr | Val | Ser | Phe | Arg | Asp | Leu | Gly | Trp | Gln | Asp | Trp | Ile | | |
|  |  | 65 |  |  |  |  | 70 |  |  |  |  | 75 |  |  |  | | |
| ATC | GCG | CCT | GAA | GGC | TAC | GCC | GCC | TAC | TAC | TGT | GAG | GGG | GAG | TGT | GCC | | 347 |
| Ile | Ala | Pro | Glu | Gly | Tyr | Ala | Ala | Tyr | Tyr | Cys | Glu | Gly | Glu | Cys | Ala | | |
|  | 80 |  |  |  |  | 85 |  |  |  |  |  | 90 |  |  |  | | |
| TTC | CCT | CTG | AAC | TCC | TAC | ATG | AAC | GCC | ACC | AAC | CAC | GCC | ATC | GTG | CAG | | 395 |
| Phe | Pro | Leu | Asn | Ser | Tyr | Met | Asn | Ala | Thr | Asn | His | Ala | Ile | Val | Gln | | |
| 95 |  |  |  |  |  | 100 |  |  |  |  | 105 |  |  |  | 110 | | |
| ACG | CTG | GTC | CAC | TTC | ATC | AAC | CCG | GAA | ACG | GTG | CCC | AAG | CCC | TGC | TGT | | 443 |
| Thr | Leu | Val | His | Phe | Ile | Asn | Pro | Glu | Thr | Val | Pro | Lys | Pro | Cys | Cys | | |
|  |  |  |  | 115 |  |  |  |  | 120 |  |  |  |  | 125 |  | | |
| GCG | CCC | ACG | CAG | CTC | AAT | GCC | ATC | TCC | GTC | CTC | TAC | TTC | GAT | GAC | AGC | | 491 |
| Ala | Pro | Thr | Gln | Leu | Asn | Ala | Ile | Ser | Val | Leu | Tyr | Phe | Asp | Asp | Ser | | |
|  |  |  | 130 |  |  |  |  | 135 |  |  |  |  | 140 |  |  | | |
| TCC | AAC | GTC | ATC | CTG | AAG | AAA | TAC | AGA | AAC | ATG | GTG | GTC | CGG | GCC | TGT | | 539 |
| Ser | Asn | Val | Ile | Leu | Lys | Lys | Tyr | Arg | Asn | Met | Val | Val | Arg | Ala | Cys | | |
|  |  | 145 |  |  |  |  | 150 |  |  |  |  | 155 |  |  |  | | |
| GGC | TGC | CAC | GCA | TTG | GAT | CCG | ATC | AAA | ATC | TCG | GGT | AAA | TGG | AAG | GCC | | 587 |
| Gly | Cys | His | Ala | Leu | Asp | Pro | Ile | Lys | Ile | Ser | Gly | Lys | Trp | Lys | Ala | | |
| 160 |  |  |  |  |  | 165 |  |  |  |  | 170 |  |  |  |  | | |
| CAG | AAA | CGC | TTT | CTG | AAA | AAG | TCG | AAA | GTG | GGT | TGG | CTG | ATC | CAG | CTG | | 635 |
| Gln | Lys | Arg | Phe | Leu | Lys | Lys | Ser | Lys | Val | Gly | Trp | Leu | Ile | Gln | Leu | | |
| 175 |  |  |  |  | 180 |  |  |  |  | 185 |  |  |  |  | 190 | | |
| TTT | CAT | AAA | AAG | ATTAGCTCGA | G |  |  |  |  |  |  |  |  |  |  | | 658 |
| Phe | His | Lys | Lys |  |  |  |  |  |  |  |  |  |  |  |  | | |

(2) INFORMATION FOR SEQ ID NO:255:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO:255:

| Met | Lys | Tyr | Leu | Leu | Pro | Thr | Ala | Ala | Ala | Gly | Leu | Leu | Leu | Leu | Ala |
|---|---|---|---|---|---|---|---|---|---|---|---|---|---|---|---|
| 1 |  |  |  | 5 |  |  |  |  | 10 |  |  |  |  | 15 |  |
| Ala | Gln | Pro | Ala | Met | Ala | Ser | Thr | Gly | Ser | Lys | Gln | Arg | Ser | Gln | Asn |
|  |  |  | 20 |  |  |  |  | 25 |  |  |  |  | 30 |  |  |
| Arg | Ser | Lys | Thr | Pro | Lys | Asn | Gln | Glu | Ala | Leu | Arg | Met | Ala | Asn | Val |
|  |  | 35 |  |  |  |  | 40 |  |  |  |  | 45 |  |  |  |
| Ala | Glu | Asn | Ser | Ser | Ser | Asp | Gln | Arg | Gln | Ala | Cys | Lys | Lys | His | Glu |
|  | 50 |  |  |  |  | 55 |  |  |  |  | 60 |  |  |  |  |
| Leu | Tyr | Val | Ser | Phe | Arg | Asp | Leu | Gly | Trp | Gln | Asp | Trp | Ile | Ile | Ala |
| 65 |  |  |  |  | 70 |  |  |  |  | 75 |  |  |  |  | 80 |
| Pro | Glu | Gly | Tyr | Ala | Ala | Tyr | Tyr | Cys | Glu | Gly | Glu | Cys | Ala | Phe | Pro |
|  |  |  |  | 85 |  |  |  |  | 90 |  |  |  |  | 95 |  |
| Leu | Asn | Ser | Tyr | Met | Asn | Ala | Thr | Asn | His | Ala | Ile | Val | Gln | Thr | Leu |
|  |  |  | 100 |  |  |  |  | 105 |  |  |  |  | 110 |  |  |
| Val | His | Phe | Ile | Asn | Pro | Glu | Thr | Val | Pro | Lys | Pro | Cys | Cys | Ala | Pro |
|  |  | 115 |  |  |  |  | 120 |  |  |  |  | 125 |  |  |  |
| Thr | Gln | Leu | Asn | Ala | Ile | Ser | Val | Leu | Tyr | Phe | Asp | Asp | Ser | Ser | Asn |
|  | 130 |  |  |  |  | 135 |  |  |  |  | 140 |  |  |  |  |

-continued

```
Val Ile Leu Lys Lys Tyr Arg Asn Met Val Val Arg Ala Cys Gly Cys
145                 150                 155                 160

His Ala Leu Asp Pro Ile Lys Ile Ser Gly Lys Trp Lys Ala Gln Lys
                165             170                 175

Arg Phe Leu Lys Lys Ser Lys Val Gly Trp Leu Ile Gln Leu Phe His
            180                 185                 190

Lys Lys
```

( 2 ) INFORMATION FOR SEQ ID NO:256:

( i ) SEQUENCE CHARACTERISTICS:
        ( A ) LENGTH: 613 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 66..602

( i x ) FEATURE:
        ( A ) NAME/KEY: misc_feature
        ( B ) LOCATION:residues 1-65
        ( D ) OTHER INFORMATION: /label=EcoRI
            / note="residues 1-65 comprise EcoRI site to beginning of
            pel B."

( i x ) FEATURE:
        ( A ) NAME/KEY: misc_feature
        ( B ) LOCATION:AA 1-22
        ( D ) OTHER INFORMATION: /label=pel B
            / note="pel B is the leader sequence from the pectate
            lyase gene of Erwinia caratovora."

( i x ) FEATURE:
        ( A ) NAME/KEY: misc_feature
        ( B ) LOCATION:AA 23-161
        ( D ) OTHER INFORMATION: /label="Bone D"
            / note="Bone D is the subunit of human osteogenic protein
            (see, U.S. Patent No. 5,284,756 e.g., Fig. 6, Example 9,
            Seq ID NOs: 1 and 2."

( i x ) FEATURE:
        ( A ) NAME/KEY: misc_feature
        ( B ) LOCATION:AA 162-165
        ( D ) OTHER INFORMATION: /label=cleavage linker
            / note="Ala-Leu-Asp-Pro linking sequence with Asp-Pro
            cleavage site."

( i x ) FEATURE:
        ( A ) NAME/KEY: misc_feature
        ( B ) LOCATION:AA 166-179
        ( D ) OTHER INFORMATION: /label=peptide sequence
            / note="BPI-derived peptide."

( i x ) FEATURE:
        ( A ) NAME/KEY: misc_feature
        ( B ) LOCATION:residues 603-613
        ( D ) OTHER INFORMATION: /label=XhoI
            / note="residues 603-613 comprise stop codon and XhoI
            site."

( x i ) SEQUENCE DESCRIPTION: SEQ ID NO:256:

```
GAATTCCTGC AGGTCTATGG AACGATAAAT GCCCATGAAA ATTCTATTTC AAGGAGACAG         60

TCATA ATG AAA TAC CTA TTG CCT ACG GCA GCC GCT GGA TTG TTA TTA           107
      Met Lys Tyr Leu Leu Pro Thr Ala Ala Ala Gly Leu Leu Leu
        1           5                  10

CTC GCT GCC CAA CCA GCG ATG GCG TCC ACG GGG AGC AAA CAG CGC AGC         155
Leu Ala Ala Gln Pro Ala Met Ala Ser Thr Gly Ser Lys Gln Arg Ser
 15              20              25                  30
```

| | | | | | | | | | | | | | | | | |
|---|---|---|---|---|---|---|---|---|---|---|---|---|---|---|---|---|
| CAG | AAC | CGC | TCC | AAG | ACG | CCC | AAG | AAC | CAG | GAA | GCC | CTG | CGG | ATG | GCC | 203 |
| Gln | Asn | Arg | Ser | Lys | Thr | Pro | Lys | Asn | Gln | Glu | Ala | Leu | Arg | Met | Ala | |
| | | | | 35 | | | | | 40 | | | | | 45 | | |
| AAC | GTG | GCA | GAG | AAC | AGC | AGC | AGC | GAC | CAG | AGG | CAG | GCC | TGT | AAG | AAG | 251 |
| Asn | Val | Ala | Glu | Asn | Ser | Ser | Ser | Asp | Gln | Arg | Gln | Ala | Cys | Lys | Lys | |
| | | | 50 | | | | | 55 | | | | | 60 | | | |
| CAC | GAG | CTG | TAT | GTC | AGC | TTC | CGA | GAC | CTG | GGC | TGG | CAG | GAC | TGG | ATC | 299 |
| His | Glu | Leu | Tyr | Val | Ser | Phe | Arg | Asp | Leu | Gly | Trp | Gln | Asp | Trp | Ile | |
| | | | 65 | | | | | 70 | | | | | 75 | | | |
| ATC | GCG | CCT | GAA | GGC | TAC | GCC | GCC | TAC | TAC | TGT | GAG | GGG | GAG | TGT | GCC | 347 |
| Ile | Ala | Pro | Glu | Gly | Tyr | Ala | Ala | Tyr | Tyr | Cys | Glu | Gly | Glu | Cys | Ala | |
| | | 80 | | | | | 85 | | | | | 90 | | | | |
| TTC | CCT | CTG | AAC | TCC | TAC | ATG | AAC | GCC | ACC | AAC | CAC | GCC | ATC | GTG | CAG | 395 |
| Phe | Pro | Leu | Asn | Ser | Tyr | Met | Asn | Ala | Thr | Asn | His | Ala | Ile | Val | Gln | |
| | 95 | | | | | 100 | | | | | 105 | | | | 110 | |
| ACG | CTG | GTC | CAC | TTC | ATC | AAC | CCG | GAA | ACG | GTG | CCC | AAG | CCC | TGC | TGT | 443 |
| Thr | Leu | Val | His | Phe | Ile | Asn | Pro | Glu | Thr | Val | Pro | Lys | Pro | Cys | Cys | |
| | | | | 115 | | | | | 120 | | | | | 125 | | |
| GCG | CCC | ACG | CAG | CTC | AAT | GCC | ATC | TCC | GTC | CTC | TAC | TTC | GAT | GAC | AGC | 491 |
| Ala | Pro | Thr | Gln | Leu | Asn | Ala | Ile | Ser | Val | Leu | Tyr | Phe | Asp | Asp | Ser | |
| | | | 130 | | | | | 135 | | | | | 140 | | | |
| TCC | AAC | GTC | ATC | CTG | AAG | AAA | TAC | AGA | AAC | ATG | GTG | GTC | CGG | GCC | TGT | 539 |
| Ser | Asn | Val | Ile | Leu | Lys | Lys | Tyr | Arg | Asn | Met | Val | Val | Arg | Ala | Cys | |
| | | | 145 | | | | | 150 | | | | | 155 | | | |
| GGC | TGC | CAC | GCA | TTG | GAT | CCG | AAG | TCT | AAA | GTG | GGG | GCC | CTG | ATC | CAG | 587 |
| Gly | Cys | His | Ala | Leu | Asp | Pro | Lys | Ser | Lys | Val | Gly | Ala | Leu | Ile | Gln | |
| | | 160 | | | | | 165 | | | | | 170 | | | | |
| CTG | TTC | CAC | AAA | AAG | TAAAGCTCGA G | | | | | | | | | | | 613 |
| Leu | Phe | His | Lys | Lys | | | | | | | | | | | | |
| 175 | | | | | | | | | | | | | | | | |

( 2 ) INFORMATION FOR SEQ ID NO:257:

( i ) SEQUENCE CHARACTERISTICS:
        ( A ) LENGTH: 179 amino acids
        ( B ) TYPE: amino acid
        ( D ) TOPOLOGY: linear ( i i ) MOLECULE TYPE: protein ( x i ) SEQUENCE DESCRIPTION: SEQ ID NO:257:

| | | | | | | | | | | | | | | | |
|---|---|---|---|---|---|---|---|---|---|---|---|---|---|---|---|
| Met | Lys | Tyr | Leu | Leu | Pro | Thr | Ala | Ala | Ala | Gly | Leu | Leu | Leu | Leu | Ala |
| 1 | | | | 5 | | | | | 10 | | | | | 15 | |
| Ala | Gln | Pro | Ala | Met | Ala | Ser | Thr | Gly | Ser | Lys | Gln | Arg | Ser | Gln | Asn |
| | | | 20 | | | | | 25 | | | | | 30 | | |
| Arg | Ser | Lys | Thr | Pro | Lys | Asn | Gln | Glu | Ala | Leu | Arg | Met | Ala | Asn | Val |
| | | | 35 | | | | | 40 | | | | | 45 | | |
| Ala | Glu | Asn | Ser | Ser | Ser | Asp | Gln | Arg | Gln | Ala | Cys | Lys | Lys | His | Glu |
| | 50 | | | | | 55 | | | | | 60 | | | | |
| Leu | Tyr | Val | Ser | Phe | Arg | Asp | Leu | Gly | Trp | Gln | Asp | Trp | Ile | Ile | Ala |
| 65 | | | | | 70 | | | | | 75 | | | | | 80 |
| Pro | Glu | Gly | Tyr | Ala | Ala | Tyr | Tyr | Cys | Glu | Gly | Glu | Cys | Ala | Phe | Pro |
| | | | | 85 | | | | | 90 | | | | | 95 | |
| Leu | Asn | Ser | Tyr | Met | Asn | Ala | Thr | Asn | His | Ala | Ile | Val | Gln | Thr | Leu |
| | | | 100 | | | | | 105 | | | | | 110 | | |
| Val | His | Phe | Ile | Asn | Pro | Glu | Thr | Val | Pro | Lys | Pro | Cys | Cys | Ala | Pro |
| | | 115 | | | | | 120 | | | | | 125 | | | |
| Thr | Gln | Leu | Asn | Ala | Ile | Ser | Val | Leu | Tyr | Phe | Asp | Asp | Ser | Ser | Asn |
| | 130 | | | | | 135 | | | | | 140 | | | | |
| Val | Ile | Leu | Lys | Lys | Tyr | Arg | Asn | Met | Val | Val | Arg | Ala | Cys | Gly | Cys |

|   |   |   |   |   | 145 |   |   |   |   | 150 |   |   |   |   | 155 |   |   |   |   | 160 |
|---|---|---|---|---|---|---|---|---|---|---|---|---|---|---|---|---|---|---|---|---|

His Ala Leu Asp Pro Lys Ser Lys Val Gly Ala Leu Ile Gln Leu Phe
165 170 175

His Lys Lys (2) INFORMATION FOR SEQ ID NO:258:

(i) SEQUENCE CHARACTERISTICS:
        (A) LENGTH: 955 base pairs
        (B) TYPE: nucleic acid
        (C) STRANDEDNESS: single
        (D) TOPOLOGY: linear (ii) MOLECULE TYPE: protein (ix) FEATURE:
        (A) NAME/KEY: CDS
        (B) LOCATION: 66..944

(ix) FEATURE:
        (A) NAME/KEY: misc_feature
        (B) LOCATION:residues 1-65
        (D) OTHER INFORMATION: /label=EcoRI
            / note="residues 1-65 comprise EcoRI site to beginning of pel B."

(ix) FEATURE:
        (A) NAME/KEY: misc_feature
        (B) LOCATION:AA 1-22
        (D) OTHER INFORMATION: /label=pel B
            / note="pel B is the leader sequence from the pectate lyase gene of Erwinia caratovora."

(ix) FEATURE:
        (A) NAME/KEY: misc_feature
        (B) LOCATION:AA 23-273
        (D) OTHER INFORMATION: /label="gelonin"
            / note="gelonin (see U.S. Patent No. 5,416,202)."

(ix) FEATURE:
        (A) NAME/KEY: misc_feature
        (B) LOCATION:AA 274-275
        (D) OTHER INFORMATION: /label=EagI
            / note="EagI cloning site."

(ix) FEATURE:
        (A) NAME/KEY: misc_feature
        (B) LOCATION:AA 276-279
        (D) OTHER INFORMATION: /label=cleavage linker
            / note="Ala-Leu-Asp-Pro linking sequence with Asp-Pro cleavage site."

(ix) FEATURE:
        (A) NAME/KEY: misc_feature
        (B) LOCATION:AA 280-293
        (D) OTHER INFORMATION: /label=peptide sequence
            / note="BPI-derived peptide."

(ix) FEATURE:
        (A) NAME/KEY: misc_feature
        (B) LOCATION:residues 945-954
        (D) OTHER INFORMATION: /label=XhoI
            / note="residues 945-955 comprise stop codon and XhoI site."

(xi) SEQUENCE DESCRIPTION: SEQ ID NO:258:

GAATTCCTGC AGGTCTATGG AACGATAAAT GCCCATGAAA ATTCTATTTC AAGGAGACAG     60

TCATA ATG AAA TAC CTA TTG CCT ACG GCA GCC GCT GGA TTG TTA TTA     107
     Met Lys Tyr Leu Leu Pro Thr Ala Ala Ala Gly Leu Leu Leu
      1              5                    10

CTC GCT GCC CAA CCA GCG ATG GCG GGC CTG GAC ACC GTG AGC TTT AGC     155
Leu Ala Ala Gln Pro Ala Met Ala Gly Leu Asp Thr Val Ser Phe Ser
 15            20              25              30

| | | | | | | | | | | | | | | | | |
|---|---|---|---|---|---|---|---|---|---|---|---|---|---|---|---|---|
| ACT | AAA | GGT | GCC | ACT | TAT | ATT | ACC | TAC | GTG | AAT | TTC | TTG | AAT | GAG | CTA | 203 |
| Thr | Lys | Gly | Ala | Thr | Tyr | Ile | Thr | Tyr | Val | Asn | Phe | Leu | Asn | Glu | Leu | |
| | | | | 35 | | | | 40 | | | | | | 45 | | |
| CGA | GTT | AAA | TTG | AAA | CCC | GAA | GGT | AAC | AGC | CAT | GGA | ATC | CCA | TTG | CTG | 251 |
| Arg | Val | Lys | Leu | Lys | Pro | Glu | Gly | Asn | Ser | His | Gly | Ile | Pro | Leu | Leu | |
| | | | 50 | | | | | 55 | | | | | 60 | | | |
| CGC | AAA | AAA | TGT | GAT | GAT | CCT | GGA | AAG | TGT | TTC | GTT | TTG | GTA | GCG | CTT | 299 |
| Arg | Lys | Lys | Cys | Asp | Asp | Pro | Gly | Lys | Cys | Phe | Val | Leu | Val | Ala | Leu | |
| | | 65 | | | | | 70 | | | | | 75 | | | | |
| TCA | AAT | GAC | AAT | GGA | CAG | TTG | GCG | GAA | ATA | GCT | ATA | GAT | GTT | ACA | AGT | 347 |
| Ser | Asn | Asp | Asn | Gly | Gln | Leu | Ala | Glu | Ile | Ala | Ile | Asp | Val | Thr | Ser | |
| | 80 | | | | | 85 | | | | | 90 | | | | | |
| GTT | TAT | GTG | GTG | GGC | TAT | CAA | GTA | AGA | AAC | AGA | TCT | TAC | TTC | TTT | AAA | 395 |
| Val | Tyr | Val | Val | Gly | Tyr | Gln | Val | Arg | Asn | Arg | Ser | Tyr | Phe | Phe | Lys | |
| 95 | | | | | 100 | | | | | 105 | | | | | 110 | |
| GAT | GCT | CCA | GAT | GCT | GCT | TAC | GAA | GGC | CTC | TTC | AAA | AAC | ACA | ATT | AAA | 443 |
| Asp | Ala | Pro | Asp | Ala | Ala | Tyr | Glu | Gly | Leu | Phe | Lys | Asn | Thr | Ile | Lys | |
| | | | | 115 | | | | | 120 | | | | | 125 | | |
| ACA | AGA | CTT | CAT | TTT | GGC | GGC | ACG | TAT | CCC | TCG | CTG | GAA | GGT | GAG | AAG | 491 |
| Thr | Arg | Leu | His | Phe | Gly | Gly | Thr | Tyr | Pro | Ser | Leu | Glu | Gly | Glu | Lys | |
| | | | 130 | | | | | 135 | | | | | 140 | | | |
| GCA | TAT | AGA | GAG | ACA | ACA | GAC | TTG | GGC | ATT | GAA | CCA | TTA | AGG | ATT | GGC | 539 |
| Ala | Tyr | Arg | Glu | Thr | Thr | Asp | Leu | Gly | Ile | Glu | Pro | Leu | Arg | Ile | Gly | |
| | | 145 | | | | | 150 | | | | | 155 | | | | |
| ATC | AAG | AAA | CTT | GAT | GAA | AAT | GCG | ATA | GAC | AAT | TAT | AAA | CCA | ACG | GAG | 587 |
| Ile | Lys | Lys | Leu | Asp | Glu | Asn | Ala | Ile | Asp | Asn | Tyr | Lys | Pro | Thr | Glu | |
| | 160 | | | | | 165 | | | | | 170 | | | | | |
| ATA | GCT | AGT | TCT | CTA | TTG | GTT | GTT | ATT | CAA | ATG | GTG | TCT | GAA | GCA | GCT | 635 |
| Ile | Ala | Ser | Ser | Leu | Leu | Val | Val | Ile | Gln | Met | Val | Ser | Glu | Ala | Ala | |
| 175 | | | | | 180 | | | | | 185 | | | | | 190 | |
| CGA | TTC | ACC | TTT | ATT | GAG | AAC | CAA | ATT | AGA | AAT | AAC | TTT | CAA | CAG | AGA | 683 |
| Arg | Phe | Thr | Phe | Ile | Glu | Asn | Gln | Ile | Arg | Asn | Asn | Phe | Gln | Gln | Arg | |
| | | | | 195 | | | | | 200 | | | | | 205 | | |
| ATT | CGC | CCG | GCG | AAT | AAT | ACA | ATC | AGC | CTT | GAG | AAT | AAA | TGG | GGT | AAA | 731 |
| Ile | Arg | Pro | Ala | Asn | Asn | Thr | Ile | Ser | Leu | Glu | Asn | Lys | Trp | Gly | Lys | |
| | | | 210 | | | | | 215 | | | | | 220 | | | |
| CTC | TCG | TTC | CAG | ATC | CGG | ACA | TCA | GGT | GCA | AAT | GGA | ATG | TTT | TCG | GAG | 779 |
| Leu | Ser | Phe | Gln | Ile | Arg | Thr | Ser | Gly | Ala | Asn | Gly | Met | Phe | Ser | Glu | |
| | | 225 | | | | | 230 | | | | | 235 | | | | |
| GCA | GTT | GAA | TTG | GAA | CGT | GCA | AAT | GGC | AAA | AAA | TAC | TAT | GTC | ACC | GCA | 827 |
| Ala | Val | Glu | Leu | Glu | Arg | Ala | Asn | Gly | Lys | Lys | Tyr | Tyr | Val | Thr | Ala | |
| | 240 | | | | | 245 | | | | | 250 | | | | | |
| GTT | GAT | CAA | GTA | AAA | CCC | AAA | ATA | GCA | CTC | TTG | AAG | TTC | GTC | GAT | AAA | 875 |
| Val | Asp | Gln | Val | Lys | Pro | Lys | Ile | Ala | Leu | Leu | Lys | Phe | Val | Asp | Lys | |
| 255 | | | | | 260 | | | | | 265 | | | | | 270 | |
| GAT | CCT | AAA | TCG | GCC | GCA | TTG | GAT | CCG | AAG | TCT | AAA | GTG | GGG | GCC | CTG | 923 |
| Asp | Pro | Lys | Ser | Ala | Ala | Leu | Asp | Pro | Lys | Ser | Lys | Val | Gly | Ala | Leu | |
| | | | | 275 | | | | | 280 | | | | | 285 | | |
| ATC | CAG | CTG | TTC | CAC | AAA | AAG | TAAAGCTCGA | G | | | | | | | | 955 |
| Ile | Gln | Leu | Phe | His | Lys | Lys | | | | | | | | | | |
| | | | 290 | | | | | | | | | | | | | |

( 2 ) INFORMATION FOR SEQ ID NO:259:

( i ) SEQUENCE CHARACTERISTICS:
        ( A ) LENGTH: 293 amino acids
        ( B ) TYPE: amino acid
        ( D ) TOPOLOGY: linear ( i i ) MOLECULE TYPE: protein ( x i ) SEQUENCE DESCRIPTION: SEQ ID NO:259:

| | | | | | | | | | | | | | | |
|---|---|---|---|---|---|---|---|---|---|---|---|---|---|---|
| Met | Lys | Tyr | Leu | Leu | Pro | Thr | Ala | Ala | Ala | Gly | Leu | Leu | Leu | Leu | Ala |
| 1 | | | | 5 | | | | | 10 | | | | | 15 | |
| Ala | Gln | Pro | Ala | Met | Ala | Gly | Leu | Asp | Thr | Val | Ser | Phe | Ser | Thr | Lys |
| | | | 20 | | | | | 25 | | | | | 30 | | |
| Gly | Ala | Thr | Tyr | Ile | Thr | Tyr | Val | Asn | Phe | Leu | Asn | Glu | Leu | Arg | Val |
| | | 35 | | | | | 40 | | | | | 45 | | | |
| Lys | Leu | Lys | Pro | Glu | Gly | Asn | Ser | His | Gly | Ile | Pro | Leu | Leu | Arg | Lys |
| | 50 | | | | | 55 | | | | | 60 | | | | |
| Lys | Cys | Asp | Asp | Pro | Gly | Lys | Cys | Phe | Val | Leu | Val | Ala | Leu | Ser | Asn |
| 65 | | | | | 70 | | | | | 75 | | | | | 80 |
| Asp | Asn | Gly | Gln | Leu | Ala | Glu | Ile | Ala | Ile | Asp | Val | Thr | Ser | Val | Tyr |
| | | | | 85 | | | | | 90 | | | | | 95 | |
| Val | Val | Gly | Tyr | Gln | Val | Arg | Asn | Arg | Ser | Tyr | Phe | Phe | Lys | Asp | Ala |
| | | | 100 | | | | | 105 | | | | | 110 | | |
| Pro | Asp | Ala | Ala | Tyr | Glu | Gly | Leu | Phe | Lys | Asn | Thr | Ile | Lys | Thr | Arg |
| | | 115 | | | | | 120 | | | | | 125 | | | |
| Leu | His | Phe | Gly | Gly | Thr | Tyr | Pro | Ser | Leu | Glu | Gly | Glu | Lys | Ala | Tyr |
| | 130 | | | | | 135 | | | | | 140 | | | | |
| Arg | Glu | Thr | Thr | Asp | Leu | Gly | Ile | Glu | Pro | Leu | Arg | Ile | Gly | Ile | Lys |
| 145 | | | | | 150 | | | | | 155 | | | | | 160 |
| Lys | Leu | Asp | Glu | Asn | Ala | Ile | Asp | Asn | Tyr | Lys | Pro | Thr | Glu | Ile | Ala |
| | | | | 165 | | | | | 170 | | | | | 175 | |
| Ser | Ser | Leu | Leu | Val | Val | Ile | Gln | Met | Val | Ser | Glu | Ala | Ala | Arg | Phe |
| | | | 180 | | | | | 185 | | | | | 190 | | |
| Thr | Phe | Ile | Glu | Asn | Gln | Ile | Arg | Asn | Asn | Phe | Gln | Gln | Arg | Ile | Arg |
| | | 195 | | | | | 200 | | | | | 205 | | | |
| Pro | Ala | Asn | Asn | Thr | Ile | Ser | Leu | Glu | Asn | Lys | Trp | Gly | Lys | Leu | Ser |
| | 210 | | | | | 215 | | | | | 220 | | | | |
| Phe | Gln | Ile | Arg | Thr | Ser | Gly | Ala | Asn | Gly | Met | Phe | Ser | Glu | Ala | Val |
| 225 | | | | | 230 | | | | | 235 | | | | | 240 |
| Glu | Leu | Glu | Arg | Ala | Asn | Gly | Lys | Lys | Tyr | Tyr | Val | Thr | Ala | Val | Asp |
| | | | | 245 | | | | | 250 | | | | | 255 | |
| Gln | Val | Lys | Pro | Lys | Ile | Ala | Leu | Leu | Lys | Phe | Val | Asp | Lys | Asp | Pro |
| | | | 260 | | | | | 265 | | | | | 270 | | |
| Lys | Ser | Ala | Ala | Leu | Asp | Pro | Lys | Ser | Lys | Val | Gly | Ala | Leu | Ile | Gln |
| | | 275 | | | | | 280 | | | | | 285 | | | |
| Leu | Phe | His | Lys | Lys | | | | | | | | | | | |
| | | | | 290 | | | | | | | | | | | |

( 2 ) INFORMATION FOR SEQ ID NO:260:

( i ) SEQUENCE CHARACTERISTICS:
        ( A ) LENGTH: 613 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 66..602

( i x ) FEATURE:
        ( A ) NAME/KEY: misc_feature
        ( B ) LOCATION:residues 1-65
        ( D ) OTHER INFORMATION: /label=EcoRI
            / note="residues 1-65 comprise EcoRI site to beginning of pel B."

( i x ) FEATURE:

(A) NAME/KEY: misc_feature
(B) LOCATION:AA 1-22
(D) OTHER INFORMATION: /label=pel B
    /note="pel B is the leader sequence from the pectate
    lyase gene of Erwinia caratovora."

(ix) FEATURE:
(A) NAME/KEY: misc_feature
(B) LOCATION:AA 23-161
(D) OTHER INFORMATION: /label="Bone D"
    /note="Bone D is the subunit of human osteogenic protein
    (see, U.S. Patent No. 5,284,756 e.g., Fig. 6, Example 9,
    Seq ID NOs: 1 and 2."

(ix) FEATURE:
(A) NAME/KEY: misc_feature
(B) LOCATION:AA 162-165
(D) OTHER INFORMATION: /label=cleavage linker
    /note="Ala-Leu-Asp-Pro linking sequence with Asp-Pro
    cleavage site."

(ix) FEATURE:
(A) NAME/KEY: misc_feature
(B) LOCATION:AA 166-179
(D) OTHER INFORMATION: /label=peptide sequence
    /note="BPI-derived peptide."

(ix) FEATURE:
(A) NAME/KEY: misc_feature
(B) LOCATION:residues 603-613
(D) OTHER INFORMATION: /label=XhoI
    /note="residues 603-613 comprise stop codon and XhoI
    site."

(xi) SEQUENCE DESCRIPTION: SEQ ID NO:260:

```
GAATTCCTGC AGGTCTATGG AACGATAAAT GCCCATGAAA ATTCTATTTC AAGGAGACAG                60

TCATA ATG AAA TAC CTA TTG CCT ACG GCA GCC GCT GGA TTG TTA TTA                    107
      Met Lys Tyr Leu Leu Pro Thr Ala Ala Ala Gly Leu Leu Leu
       1               5                         10

CTC GCT GCC CAA CCA GCG ATG GCG TCC ACG GGG AGC AAA CAG CGC AGC                  155
Leu Ala Ala Gln Pro Ala Met Ala Ser Thr Gly Ser Lys Gln Arg Ser
 15              20                  25                      30

CAG AAC CGC TCC AAG ACG CCC AAG AAC CAG GAA GCC CTG CGG ATG GCC                  203
Gln Asn Arg Ser Lys Thr Pro Lys Asn Gln Glu Ala Leu Arg Met Ala
                  35              40                      45

AAC GTG GCA GAG AAC AGC AGC AGC GAC CAG AGG CAG GCC TGT AAG AAG                  251
Asn Val Ala Glu Asn Ser Ser Ser Asp Gln Arg Gln Ala Cys Lys Lys
              50                  55                  60

CAC GAG CTG TAT GTC AGC TTC CGA GAC CTG GGC TGG CAG GAC TGG ATC                  299
His Glu Leu Tyr Val Ser Phe Arg Asp Leu Gly Trp Gln Asp Trp Ile
          65                  70                  75

ATC GCG CCT GAA GGC TAC GCC GCC TAC TAC TGT GAG GGG GAG TGT GCC                  347
Ile Ala Pro Glu Gly Tyr Ala Ala Tyr Tyr Cys Glu Gly Glu Cys Ala
      80                  85                  90

TTC CCT CTG AAC TCC TAC ATG AAC GCC ACC AAC CAC GCC ATC GTG CAG                  395
Phe Pro Leu Asn Ser Tyr Met Asn Ala Thr Asn His Ala Ile Val Gln
 95                 100                 105                 110

ACG CTG GTC CAC TTC ATC AAC CCG GAA ACG GTG CCC AAG CCC TGC TGT                  443
Thr Leu Val His Phe Ile Asn Pro Glu Thr Val Pro Lys Pro Cys Cys
                115                 120                 125

GCG CCC ACG CAG CTC AAT GCC ATC TCC GTC CTC TAC TTC GAT GAC AGC                  491
Ala Pro Thr Gln Leu Asn Ala Ile Ser Val Leu Tyr Phe Asp Asp Ser
            130                 135                 140

TCC AAC GTC ATC CTG AAG AAA TAC AGA AAC ATG GTG GTC CGG GCC TGT                  539
Ser Asn Val Ile Leu Lys Lys Tyr Arg Asn Met Val Val Arg Ala Cys
        145                 150                 155

GGC TGC CAC GCA TTG GAT CCG AAG TCT AAA GTG GGG GCC CTG ATC CAG                  587
Gly Cys His Ala Leu Asp Pro Lys Ser Lys Val Gly Ala Leu Ile Gln
```

```
                    160                          165                           170
CTG  TTC  CAC  AAA  AAG  TAAAGCTCGA  G                                                              613
Leu  Phe  His  Lys  Lys
175
```

( 2 ) INFORMATION FOR SEQ ID NO:261:

( i ) SEQUENCE CHARACTERISTICS:
        ( A ) LENGTH: 179 amino acids
        ( B ) TYPE: amino acid
        ( D ) TOPOLOGY: linear ( i i ) MOLECULE TYPE: protein ( x i ) SEQUENCE DESCRIPTION: SEQ ID NO:261:

```
Met  Lys  Tyr  Leu  Leu  Pro  Thr  Ala  Ala  Ala  Gly  Leu  Leu  Leu  Leu  Ala
 1                    5                      10                        15

Ala  Gln  Pro  Ala  Met  Ala  Ser  Thr  Gly  Ser  Lys  Gln  Arg  Ser  Gln  Asn
                20                    25                        30

Arg  Ser  Lys  Thr  Pro  Lys  Asn  Gln  Glu  Ala  Leu  Arg  Met  Ala  Asn  Val
           35                      40                    45

Ala  Glu  Asn  Ser  Ser  Ser  Asp  Gln  Arg  Gln  Ala  Cys  Lys  Lys  His  Glu
     50                      55                         60

Leu  Tyr  Val  Ser  Phe  Arg  Asp  Leu  Gly  Trp  Gln  Asp  Trp  Ile  Ile  Ala
65                      70                      75                           80

Pro  Glu  Gly  Tyr  Ala  Ala  Tyr  Tyr  Cys  Glu  Gly  Glu  Cys  Ala  Phe  Pro
                     85                      90                         95

Leu  Asn  Ser  Tyr  Met  Asn  Ala  Thr  Asn  His  Ala  Ile  Val  Gln  Thr  Leu
               100                     105                       110

Val  His  Phe  Ile  Asn  Pro  Glu  Thr  Val  Pro  Lys  Pro  Cys  Cys  Ala  Pro
          115                     120                    125

Thr  Gln  Leu  Asn  Ala  Ile  Ser  Val  Leu  Tyr  Phe  Asp  Asp  Ser  Ser  Asn
     130                     135                    140

Val  Ile  Leu  Lys  Lys  Tyr  Arg  Asn  Met  Val  Val  Arg  Ala  Cys  Gly  Cys
145                     150                    155                         160

His  Ala  Leu  Asp  Pro  Lys  Ser  Lys  Val  Gly  Ala  Leu  Ile  Gln  Leu  Phe
               165                    170                         175

His  Lys  Lys
```

( 2 ) INFORMATION FOR SEQ ID NO:262:

( i ) SEQUENCE CHARACTERISTICS:
        ( A ) LENGTH: 661 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 66..650

( i x ) FEATURE:
        ( A ) NAME/KEY: misc_feature
        ( B ) LOCATION:residues 1-65
        ( D ) OTHER INFORMATION: /label=EcoRI
            / note="residues 1-65 comprise EcoRI site to beginning of
            pel B."

( i x ) FEATURE:
        ( A ) NAME/KEY: misc_feature
        ( B ) LOCATION:AA 1-22
        ( D ) OTHER INFORMATION: /label=pel B
            / note="pel B is the leader sequence from the pectate lyase gene of Erwinia caratovora."

( i x ) FEATURE:
    ( A ) NAME/KEY: misc_feature
    ( B ) LOCATION:AA 23-161
    ( D ) OTHER INFORMATION: /label="Bone D"
        / note="Bone D is the subunit of human osteogenic protein
        (see, U.S. Patent No. 5,284,756 e.g., Fig. 6, Example 9,
        Seq ID NOs: 1 and 2."

( i x ) FEATURE:
    ( A ) NAME/KEY: misc_feature
    ( B ) LOCATION:AA 162-165
    ( D ) OTHER INFORMATION: /label=cleavage linker
        / note="Ala-Leu-Asp-Pro linking sequence with Asp-Pro
        cleavage site."

( i x ) FEATURE:
    ( A ) NAME/KEY: misc_feature
    ( B ) LOCATION:AA 166-195
    ( D ) OTHER INFORMATION: /label=peptide sequence
        / note="BPI-derived peptide."

( i x ) FEATURE:
    ( A ) NAME/KEY: misc_feature
    ( B ) LOCATION:residues 651-661
    ( D ) OTHER INFORMATION: /label=XhoI
        / note="residues 651-661 comprise stop codon and XhoI
        site."

( x i ) SEQUENCE DESCRIPTION: SEQ ID NO:262:

```
GAATTCCTGC AGGTCTATGG AACGATAAAT GCCCATGAAA ATTCTATTTC AAGGAGACAG            60

TCATA ATG AAA TAC CTA TTG CCT ACG GCA GCC GCT GGA TTG TTA TTA              107
      Met Lys Tyr Leu Leu Pro Thr Ala Ala Ala Gly Leu Leu Leu
       1               5                        10

CTC GCT GCC CAA CCA GCG ATG GCG TCC ACG GGG AGC AAA CAG CGC AGC            155
Leu Ala Ala Gln Pro Ala Met Ala Ser Thr Gly Ser Lys Gln Arg Ser
 15              20                  25                      30

CAG AAC CGC TCC AAG ACG CCC AAG AAC CAG GAA GCC CTG CGG ATG GCC            203
Gln Asn Arg Ser Lys Thr Pro Lys Asn Gln Glu Ala Leu Arg Met Ala
                 35              40                      45

AAC GTG GCA GAG AAC AGC AGC AGC GAC CAG AGG CAG GCC TGT AAG AAG            251
Asn Val Ala Glu Asn Ser Ser Ser Asp Gln Arg Gln Ala Cys Lys Lys
             50                  55                  60

CAC GAG CTG TAT GTC AGC TTC CGA GAC CTG GGC TGG CAG GAC TGG ATC            299
His Glu Leu Tyr Val Ser Phe Arg Asp Leu Gly Trp Gln Asp Trp Ile
         65                  70                  75

ATC GCG CCT GAA GGC TAC GCC GCC TAC TAC TGT GAG GGG GAG TGT GCC            347
Ile Ala Pro Glu Gly Tyr Ala Ala Tyr Tyr Cys Glu Gly Glu Cys Ala
     80                  85                  90

TTC CCT CTG AAC TCC TAC ATG AAC GCC ACC AAC CAC GCC ATC GTG CAG            395
Phe Pro Leu Asn Ser Tyr Met Asn Ala Thr Asn His Ala Ile Val Gln
 95                 100                 105                 110

ACG CTG GTC CAC TTC ATC AAC CCG GAA ACG GTG CCC AAG CCC TGC TGT            443
Thr Leu Val His Phe Ile Asn Pro Glu Thr Val Pro Lys Pro Cys Cys
                 115                 120                 125

GCG CCC ACG CAG CTC AAT GCC ATC TCC GTC CTC TAC TTC GAT GAC AGC            491
Ala Pro Thr Gln Leu Asn Ala Ile Ser Val Leu Tyr Phe Asp Asp Ser
             130                 135                 140

TCC AAC GTC ATC CTG AAG AAA TAC AGA AAC ATG GTG GTC CGG GCC TGT            539
Ser Asn Val Ile Leu Lys Lys Tyr Arg Asn Met Val Val Arg Ala Cys
         145                 150                 155

GGC TGC CAC GCA TTG GAT CCG AAG TCT AAA GTG GGG GCC CTG ATC CAG            587
Gly Cys His Ala Leu Asp Pro Lys Ser Lys Val Gly Ala Leu Ile Gln
 160                 165                 170

CTG TTC CAC AAA AAG GAC CCA AAA TCC AAG GTA GGG GCC CTG ATC CAG            635
Leu Phe His Lys Lys Asp Pro Lys Ser Lys Val Gly Ala Leu Ile Gln
```

```
                175                 180                 185                 190
CTG  TTC  CAC  AAA  AAG  TAAAGCTCGA G                                              661
Leu  Phe  His  Lys  Lys
                    195
```

( 2 ) INFORMATION FOR SEQ ID NO:263:

( i ) SEQUENCE CHARACTERISTICS:
        ( A ) LENGTH: 195 amino acids
        ( B ) TYPE: amino acid
        ( D ) TOPOLOGY: linear ( i i ) MOLECULE TYPE: protein ( x i ) SEQUENCE DESCRIPTION: SEQ ID NO:263:

```
Met  Lys  Tyr  Leu  Leu  Pro  Thr  Ala  Ala  Ala  Gly  Leu  Leu  Leu  Leu  Ala
 1                   5                        10                       15

Ala  Gln  Pro  Ala  Met  Ala  Ser  Thr  Gly  Ser  Lys  Gln  Arg  Ser  Gln  Asn
               20                       25                  30

Arg  Ser  Lys  Thr  Pro  Lys  Asn  Gln  Glu  Ala  Leu  Arg  Met  Ala  Asn  Val
          35                       40                       45

Ala  Glu  Asn  Ser  Ser  Ser  Asp  Gln  Arg  Gln  Ala  Cys  Lys  Lys  His  Glu
     50                       55                       60

Leu  Tyr  Val  Ser  Phe  Arg  Asp  Leu  Gly  Trp  Gln  Asp  Trp  Ile  Ile  Ala
65                       70                       75                       80

Pro  Glu  Gly  Tyr  Ala  Ala  Tyr  Tyr  Cys  Glu  Gly  Glu  Cys  Ala  Phe  Pro
               85                       90                       95

Leu  Asn  Ser  Tyr  Met  Asn  Ala  Thr  Asn  His  Ala  Ile  Val  Gln  Thr  Leu
               100                      105                      110

Val  His  Phe  Ile  Asn  Pro  Glu  Thr  Val  Pro  Lys  Pro  Cys  Cys  Ala  Pro
          115                      120                      125

Thr  Gln  Leu  Asn  Ala  Ile  Ser  Val  Leu  Tyr  Phe  Asp  Asp  Ser  Ser  Asn
     130                      135                      140

Val  Ile  Leu  Lys  Lys  Tyr  Arg  Asn  Met  Val  Val  Arg  Ala  Cys  Gly  Cys
145                      150                      155                      160

His  Ala  Leu  Asp  Pro  Lys  Ser  Lys  Val  Gly  Ala  Leu  Ile  Gln  Leu  Phe
               165                      170                      175

His  Lys  Lys  Asp  Pro  Lys  Ser  Lys  Val  Gly  Ala  Leu  Ile  Gln  Leu  Phe
               180                      185                      190

His  Lys  Lys
          195
```

( 2 ) INFORMATION FOR SEQ ID NO:264:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( i x ) FEATURE:
        ( A ) NAME/KEY: misc_feature
        ( D ) OTHER INFORMATION: "rBPI"

( x i ) SEQUENCE DESCRIPTION: SEQ ID NO:264:

| | | | | | | | | | | | | | | | | |
|---|---|---|---|---|---|---|---|---|---|---|---|---|---|---|---|---|
| CAGGCCTTGA | | | GGTTTTGGCA | | | GCTCTGGAGG | | | ATG | AGA | GAG | AAC | ATG | GCC | AGG | GGC | 54 |
| | | | | | | | | | Met | Arg | Glu | Asn | Met | Ala | Arg | Gly | |
| | | | | | | | | | -31 | -30 | | | | | -25 | | |
| CCT | TGC | AAC | GCG | CCG | AGA | TGG | GTG | TCC | CTG | ATG | GTG | CTC | GTC | GCC | ATA | 102 |
| Pro | Cys | Asn | Ala | Pro | Arg | Trp | Val | Ser | Leu | Met | Val | Leu | Val | Ala | Ile | |
| | | | -20 | | | | | -15 | | | | | | -10 | | |
| GGC | ACC | GCC | GTG | ACA | GCG | GCC | GTC | AAC | CCT | GGC | GTG | GTG | GTC | AGG | ATC | 150 |
| Gly | Thr | Ala | Val | Thr | Ala | Ala | Val | Asn | Pro | Gly | Val | Val | Val | Arg | Ile | |
| | | -5 | | | | | | 1 | | | | 5 | | | | |
| TCC | CAG | AAG | GGC | CTG | GAC | TAC | GCC | AGC | CAG | CAG | GGG | ACG | GCC | GCT | CTG | 198 |
| Ser | Gln | Lys | Gly | Leu | Asp | Tyr | Ala | Ser | Gln | Gln | Gly | Thr | Ala | Ala | Leu | |
| 10 | | | | | 15 | | | | | 20 | | | | | 25 | |
| CAG | AAG | GAG | CTG | AAG | AGG | ATC | AAG | ATT | CCT | GAC | TAC | TCA | GAC | AGC | TTT | 246 |
| Gln | Lys | Glu | Leu | Lys | Arg | Ile | Lys | Ile | Pro | Asp | Tyr | Ser | Asp | Ser | Phe | |
| | | | | 30 | | | | | 35 | | | | | 40 | | |
| AAG | ATC | AAG | CAT | CTT | GGG | AAG | GGG | CAT | TAT | AGC | TTC | TAC | AGC | ATG | GAC | 294 |
| Lys | Ile | Lys | His | Leu | Gly | Lys | Gly | His | Tyr | Ser | Phe | Tyr | Ser | Met | Asp | |
| | | | 45 | | | | | 50 | | | | | 55 | | | |
| ATC | CGT | GAA | TTC | CAG | CTT | CCC | AGT | TCC | CAG | ATA | AGC | ATG | GTG | CCC | AAT | 342 |
| Ile | Arg | Glu | Phe | Gln | Leu | Pro | Ser | Ser | Gln | Ile | Ser | Met | Val | Pro | Asn | |
| | | 60 | | | | | 65 | | | | | 70 | | | | |
| GTG | GGC | CTT | AAG | TTC | TCC | ATC | AGC | AAC | GCC | AAT | ATC | AAG | ATC | AGC | GGG | 390 |
| Val | Gly | Leu | Lys | Phe | Ser | Ile | Ser | Asn | Ala | Asn | Ile | Lys | Ile | Ser | Gly | |
| | 75 | | | | | 80 | | | | | 85 | | | | | |
| AAA | TGG | AAG | GCA | CAA | AAG | AGA | TTC | TTA | AAA | ATG | AGC | GGC | AAT | TTT | GAC | 438 |
| Lys | Trp | Lys | Ala | Gln | Lys | Arg | Phe | Leu | Lys | Met | Ser | Gly | Asn | Phe | Asp | |
| 90 | | | | | 95 | | | | | 100 | | | | | 105 | |
| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly | Met | Ser | Ile | Ser | Ala | Asp | Leu | Lys | Leu | Gly | Ser | |
| | | | | 110 | | | | | 115 | | | | | 120 | | |
| AAC | CCC | ACG | TCA | GGC | AAG | CCC | ACC | ATC | ACC | TGC | TCC | AGC | TGC | AGC | AGC | 534 |
| Asn | Pro | Thr | Ser | Gly | Lys | Pro | Thr | Ile | Thr | Cys | Ser | Ser | Cys | Ser | Ser | |
| | | | 125 | | | | | 130 | | | | | 135 | | | |
| CAC | ATC | AAC | AGT | GTC | CAC | GTG | CAC | ATC | TCA | AAG | AGC | AAA | GTC | GGG | TGG | 582 |
| His | Ile | Asn | Ser | Val | His | Val | His | Ile | Ser | Lys | Ser | Lys | Val | Gly | Trp | |
| | | 140 | | | | | 145 | | | | | 150 | | | | |
| CTG | ATC | CAA | CTC | TTT | CAC | AAA | AAA | ATT | GAG | TCT | GCG | CTT | CGA | AAC | AAG | 630 |
| Leu | Ile | Gln | Leu | Phe | His | Lys | Lys | Ile | Glu | Ser | Ala | Leu | Arg | Asn | Lys | |
| | 155 | | | | | 160 | | | | | 165 | | | | | |
| ATG | AAC | AGC | CAG | GTC | TGC | GAG | AAA | GTG | ACC | AAT | TCT | GTA | TCC | TCC | AAG | 678 |
| Met | Asn | Ser | Gln | Val | Cys | Glu | Lys | Val | Thr | Asn | Ser | Val | Ser | Ser | Lys | |
| 170 | | | | | 175 | | | | | 180 | | | | | 185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe | Gln | Thr | Leu | Pro | Val | Met | Thr | Lys | Ile | Asp | Ser | |
| | | | | 190 | | | | | 195 | | | | | 200 | | |
| GTG | GCT | GGA | ATC | AAC | TAT | GGT | CTG | GTG | GCA | CCT | CCA | GCA | ACC | ACG | GCT | 774 |
| Val | Ala | Gly | Ile | Asn | Tyr | Gly | Leu | Val | Ala | Pro | Pro | Ala | Thr | Thr | Ala | |
| | | | 205 | | | | | 210 | | | | | 215 | | | |
| GAG | ACC | CTG | GAT | GTA | CAG | ATG | AAG | GGG | GAG | TTT | TAC | AGT | GAG | AAC | CAC | 822 |
| Glu | Thr | Leu | Asp | Val | Gln | Met | Lys | Gly | Glu | Phe | Tyr | Ser | Glu | Asn | His | |
| | | 220 | | | | | 225 | | | | | 230 | | | | |
| CAC | AAT | CCA | CCT | CCC | TTT | GCT | CCA | CCA | GTG | ATG | GAG | TTT | CCC | GCT | GCC | 870 |
| His | Asn | Pro | Pro | Pro | Phe | Ala | Pro | Pro | Val | Met | Glu | Phe | Pro | Ala | Ala | |
| | 235 | | | | | 240 | | | | | 245 | | | | | |
| CAT | GAC | CGC | ATG | GTA | TAC | CTG | GGC | CTC | TCA | GAC | TAC | TTC | TTC | AAC | ACA | 918 |
| His | Asp | Arg | Met | Val | Tyr | Leu | Gly | Leu | Ser | Asp | Tyr | Phe | Phe | Asn | Thr | |
| 250 | | | | | 255 | | | | | 260 | | | | | 265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr | Gln | Glu | Ala | Gly | Val | Leu | Lys | Met | Thr | Leu | Arg | |

|  |  |  | 270 |  |  |  | 275 |  |  |  | 280 |  |  |  |  |
|---|---|---|---|---|---|---|---|---|---|---|---|---|---|---|---|
| GAT | GAC | ATG | ATT | CCA | AAG | GAG | TCC | AAA | TTT | CGA | CTG | ACA | ACC | AAG | TTC | 1014 |
| Asp | Asp | Met | Ile 285 | Pro | Lys | Glu | Ser 290 | Lys | Phe | Arg | Leu | Thr | Thr 295 | Lys | Phe |  |
| TTT | GGA | ACC | TTC | CTA | CCT | GAG | GTG | GCC | AAG | AAG | TTT | CCC | AAC | ATG | AAG | 1062 |
| Phe | Gly | Thr 300 | Phe | Leu | Pro | Glu | Val 305 | Ala | Lys | Lys | Phe | Pro 310 | Asn | Met | Lys |  |
| ATA | CAG | ATC | CAT | GTC | TCA | GCC | TCC | ACC | CCG | CCA | CAC | CTG | TCT | GTG | CAG | 1110 |
| Ile | Gln 315 | Ile | His | Val | Ser | Ala 320 | Ser | Thr | Pro | Pro | His 325 | Leu | Ser | Val | Gln |  |
| CCC | ACC | GGC | CTT | ACC | TTC | TAC | CCT | GCC | GTG | GAT | GTC | CAG | GCC | TTT | GCC | 1158 |
| Pro 330 | Thr | Gly | Leu | Thr | Phe 335 | Tyr | Pro | Ala | Val | Asp 340 | Val | Gln | Ala | Phe | Ala 345 |  |
| GTC | CTC | CCC | AAC | TCC | TCC | CTG | GCT | TCC | CTC | TTC | CTG | ATT | GGC | ATG | CAC | 1206 |
| Val | Leu | Pro | Asn | Ser 350 | Ser | Leu | Ala | Ser | Leu 355 | Phe | Leu | Ile | Gly | Met 360 | His |  |
| ACA | ACT | GGT | TCC | ATG | GAG | GTC | AGC | GCC | GAG | TCC | AAC | AGG | CTT | GTT | GGA | 1254 |
| Thr | Thr | Gly | Ser 365 | Met | Glu | Val | Ser | Ala 370 | Glu | Ser | Asn | Arg | Leu 375 | Val | Gly |  |
| GAG | CTC | AAG | CTG | GAT | AGG | CTG | CTC | CTG | GAA | CTG | AAG | CAC | TCA | AAT | ATT | 1302 |
| Glu | Leu | Lys 380 | Leu | Asp | Arg | Leu | Leu 385 | Leu | Glu | Leu | Lys | His 390 | Ser | Asn | Ile |  |
| GGC | CCC | TTC | CCG | GTT | GAA | TTG | CTG | CAG | GAT | ATC | ATG | AAC | TAC | ATT | GTA | 1350 |
| Gly | Pro | Phe 395 | Pro | Val | Glu | Leu | Leu 400 | Gln | Asp | Ile | Met | Asn 405 | Tyr | Ile | Val |  |
| CCC | ATT | CTT | GTG | CTG | CCC | AGG | GTT | AAC | GAG | AAA | CTA | CAG | AAA | GGC | TTC | 1398 |
| Pro 410 | Ile | Leu | Val | Leu | Pro 415 | Arg | Val | Asn | Glu | Lys 420 | Leu | Gln | Lys | Gly | Phe 425 |  |
| CCT | CTC | CCG | ACG | CCG | GCC | AGA | GTC | CAG | CTC | TAC | AAC | GTA | GTG | CTT | CAG | 1446 |
| Pro | Leu | Pro | Thr | Pro 430 | Ala | Arg | Val | Gln | Leu 435 | Tyr | Asn | Val | Val | Leu 440 | Gln |  |
| CCT | CAC | CAG | AAC | TTC | CTG | CTG | TTC | GGT | GCA | GAC | GTT | GTC | TAT | AAA |  | 1491 |
| Pro | His | Gln | Asn 445 | Phe | Leu | Leu | Phe | Gly 450 | Ala | Asp | Val | Val | Tyr 455 | Lys |  |  |

| TGAAGGCACC | AGGGGTGCCG | GGGGCTGTCA | GCCGCACCTG | TTCCTGATGG | GCTGTGGGGC | 1551 |
|---|---|---|---|---|---|---|
| ACCGGCTGCC | TTTCCCCAGG | GAATCCTCTC | CAGATCTTAA | CCAAGAGCCC | CTTGCAAACT | 1611 |
| TCTTCGACTC | AGATTCAGAA | ATGATCTAAA | CACGAGGAAA | CATTATTCAT | TGGAAAAGTG | 1671 |
| CATGGTGTGT | ATTTTAGGGA | TTATGAGCTT | CTTTCAAGGG | CTAAGGCTGC | AGAGATATTT | 1731 |
| CCTCCAGGAA | TCGTGTTTCA | ATTGTAACCA | AGAAATTTCC | ATTTGTGCTT | CATGAAAAAA | 1791 |
| AACTTCTGGT | TTTTTTCATG | TG |  |  |  | 1813 |

( 2 ) INFORMATION FOR SEQ ID NO:265:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:265:

| Met -31 | Arg -30 | Glu | Asn | Met | Ala -25 | Arg | Gly | Pro | Cys | Asn -20 | Ala | Pro | Arg | Trp | Val |
|---|---|---|---|---|---|---|---|---|---|---|---|---|---|---|---|
| Ser -15 | Leu | Met | Val | Leu | Val -10 | Ala | Ile | Gly | Thr | Ala -5 | Val | Thr | Ala | Ala | Val 1 |
| Asn | Pro | Gly | Val | Val 5 | Val | Arg | Ile | Ser | Gln 10 | Lys | Gly | Leu | Asp | Tyr 15 | Ala |
| Ser | Gln | Gln | Gly | Thr | Ala | Ala | Leu | Gln | Lys | Glu | Leu | Lys | Arg | Ile | Lys |

|  |  |  | 20 |  |  |  | 25 |  |  |  | 30 |  |  |
|---|---|---|---|---|---|---|---|---|---|---|---|---|---|
| Ile | Pro | Asp | Tyr | Ser | Asp | Ser | Phe | Lys | Ile | Lys | His | Leu | Gly | Lys | Gly |
|  | 35 |  |  |  | 40 |  |  |  |  | 45 |  |  |  |  |
| His | Tyr | Ser | Phe | Tyr | Ser | Met | Asp | Ile | Arg | Glu | Phe | Gln | Leu | Pro | Ser |
| 50 |  |  |  |  | 55 |  |  |  |  | 60 |  |  |  |  | 65 |
| Ser | Gln | Ile | Ser | Met | Val | Pro | Asn | Val | Gly | Leu | Lys | Phe | Ser | Ile | Ser |
|  |  |  |  | 70 |  |  |  |  | 75 |  |  |  |  | 80 |  |
| Asn | Ala | Asn | Ile | Lys | Ile | Ser | Gly | Lys | Trp | Lys | Ala | Gln | Lys | Arg | Phe |
|  |  |  | 85 |  |  |  |  | 90 |  |  |  |  | 95 |  |  |
| Leu | Lys | Met | Ser | Gly | Asn | Phe | Asp | Leu | Ser | Ile | Glu | Gly | Met | Ser | Ile |
|  |  | 100 |  |  |  |  | 105 |  |  |  |  | 110 |  |  |  |
| Ser | Ala | Asp | Leu | Lys | Leu | Gly | Ser | Asn | Pro | Thr | Ser | Gly | Lys | Pro | Thr |
|  | 115 |  |  |  |  | 120 |  |  |  |  |  | 125 |  |  |  |
| Ile | Thr | Cys | Ser | Ser | Cys | Ser | Ser | His | Ile | Asn | Ser | Val | His | Val | His |
| 130 |  |  |  |  | 135 |  |  |  |  | 140 |  |  |  |  | 145 |
| Ile | Ser | Lys | Ser | Lys | Val | Gly | Trp | Leu | Ile | Gln | Leu | Phe | His | Lys | Lys |
|  |  |  |  | 150 |  |  |  |  | 155 |  |  |  |  | 160 |  |
| Ile | Glu | Ser | Ala | Leu | Arg | Asn | Lys | Met | Asn | Ser | Gln | Val | Cys | Glu | Lys |
|  |  |  | 165 |  |  |  |  | 170 |  |  |  |  | 175 |  |  |
| Val | Thr | Asn | Ser | Val | Ser | Ser | Lys | Leu | Gln | Pro | Tyr | Phe | Gln | Thr | Leu |
|  |  | 180 |  |  |  |  | 185 |  |  |  |  | 190 |  |  |  |
| Pro | Val | Met | Thr | Lys | Ile | Asp | Ser | Val | Ala | Gly | Ile | Asn | Tyr | Gly | Leu |
|  | 195 |  |  |  |  | 200 |  |  |  |  |  | 205 |  |  |  |
| Val | Ala | Pro | Pro | Ala | Thr | Thr | Ala | Glu | Thr | Leu | Asp | Val | Gln | Met | Lys |
| 210 |  |  |  |  | 215 |  |  |  |  | 220 |  |  |  |  | 225 |
| Gly | Glu | Phe | Tyr | Ser | Glu | Asn | His | His | Asn | Pro | Pro | Phe | Ala | Pro |  |
|  |  |  |  | 230 |  |  |  |  | 235 |  |  |  |  | 240 |  |
| Pro | Val | Met | Glu | Phe | Pro | Ala | Ala | His | Asp | Arg | Met | Val | Tyr | Leu | Gly |
|  |  |  | 245 |  |  |  |  | 250 |  |  |  |  | 255 |  |  |
| Leu | Ser | Asp | Tyr | Phe | Phe | Asn | Thr | Ala | Gly | Leu | Val | Tyr | Gln | Glu | Ala |
|  |  | 260 |  |  |  |  | 265 |  |  |  |  | 270 |  |  |  |
| Gly | Val | Leu | Lys | Met | Thr | Leu | Arg | Asp | Asp | Met | Ile | Pro | Lys | Glu | Ser |
|  | 275 |  |  |  |  | 280 |  |  |  |  |  | 285 |  |  |  |
| Lys | Phe | Arg | Leu | Thr | Thr | Lys | Phe | Phe | Gly | Thr | Phe | Leu | Pro | Glu | Val |
| 290 |  |  |  |  | 295 |  |  |  |  | 300 |  |  |  |  | 305 |
| Ala | Lys | Lys | Phe | Pro | Asn | Met | Lys | Ile | Gln | Ile | His | Val | Ser | Ala | Ser |
|  |  |  |  | 310 |  |  |  |  | 315 |  |  |  |  | 320 |  |
| Thr | Pro | Pro | His | Leu | Ser | Val | Gln | Pro | Thr | Gly | Leu | Thr | Phe | Tyr | Pro |
|  |  |  | 325 |  |  |  |  | 330 |  |  |  |  | 335 |  |  |
| Ala | Val | Asp | Val | Gln | Ala | Phe | Ala | Val | Leu | Pro | Asn | Ser | Ser | Leu | Ala |
|  |  | 340 |  |  |  |  | 345 |  |  |  |  | 350 |  |  |  |
| Ser | Leu | Phe | Leu | Ile | Gly | Met | His | Thr | Thr | Gly | Ser | Met | Glu | Val | Ser |
|  | 355 |  |  |  |  | 360 |  |  |  |  |  | 365 |  |  |  |
| Ala | Glu | Ser | Asn | Arg | Leu | Val | Gly | Glu | Leu | Lys | Leu | Asp | Arg | Leu | Leu |
| 370 |  |  |  |  | 375 |  |  |  |  | 380 |  |  |  |  | 385 |
| Leu | Glu | Leu | Lys | His | Ser | Asn | Ile | Gly | Pro | Phe | Pro | Val | Glu | Leu | Leu |
|  |  |  |  | 390 |  |  |  |  | 395 |  |  |  |  | 400 |  |
| Gln | Asp | Ile | Met | Asn | Tyr | Ile | Val | Pro | Ile | Leu | Val | Leu | Pro | Arg | Val |
|  |  |  | 405 |  |  |  |  | 410 |  |  |  |  | 415 |  |  |
| Asn | Glu | Lys | Leu | Gln | Lys | Gly | Phe | Pro | Leu | Pro | Thr | Pro | Ala | Arg | Val |
|  |  | 420 |  |  |  |  | 425 |  |  |  |  | 430 |  |  |  |
| Gln | Leu | Tyr | Asn | Val | Val | Leu | Gln | Pro | His | Gln | Asn | Phe | Leu | Leu | Phe |
|  | 435 |  |  |  |  | 440 |  |  |  |  |  | 445 |  |  |  |

```
Gly  Ala  Asp  Val  Val  Tyr  Lys
450                      455
```